United States Patent
Soula et al.

(10) Patent No.: US 9,795,678 B2
(45) Date of Patent: Oct. 24, 2017

(54) FAST-ACTING INSULIN COMPOSITION COMPRISING A SUBSTITUTED ANIONIC COMPOUND AND A POLYANIONIC COMPOUND

(71) Applicant: ADOCIA, Lyons (FR)

(72) Inventors: Olivier Soula, Meyzieu (FR); Richard Charvet, Rillieux la Pape (FR); Bertrand Alluis, Genas (FR)

(73) Assignee: ADOCIA, Lyons (FR)

( * ) Notice: Subject to any disclaimer, the term of this patent is extended or adjusted under 35 U.S.C. 154(b) by 0 days.

(21) Appl. No.: 14/712,696

(22) Filed: May 14, 2015

(65) Prior Publication Data

US 2016/0082106 A1     Mar. 24, 2016

(30) Foreign Application Priority Data

May 14, 2014    (FR) ..................... 14 54313

(51) Int. Cl.

| A61K 38/28 | (2006.01) |
| A61K 47/18 | (2017.01) |
| C07C 235/74 | (2006.01) |
| C07C 271/22 | (2006.01) |
| C07K 5/068 | (2006.01) |
| A61K 9/00 | (2006.01) |
| A61K 47/32 | (2006.01) |
| A61K 47/34 | (2017.01) |
| A61K 9/19 | (2006.01) |
| A61K 47/12 | (2006.01) |
| A61K 9/08 | (2006.01) |

(52) U.S. Cl.
CPC .......... *A61K 47/183* (2013.01); *A61K 9/0019* (2013.01); *A61K 9/08* (2013.01); *A61K 9/19* (2013.01); *A61K 38/28* (2013.01); *A61K 47/12* (2013.01); *A61K 47/32* (2013.01); *A61K 47/34* (2013.01); *C07C 235/74* (2013.01); *C07C 271/22* (2013.01); *C07K 5/06086* (2013.01)

(58) Field of Classification Search
CPC ............................. A61K 38/28; A61K 47/183
USPC .................................................. 514/6.5, 5.9
See application file for complete search history.

(56) References Cited

U.S. PATENT DOCUMENTS

| 2,387,201 A | 10/1945 | Weiner |
| 2,847,385 A | 8/1958 | Hiler |
| 4,006,059 A | 2/1977 | Butler |
| 4,011,137 A | 3/1977 | Thompson et al. |
| 4,126,628 A | 11/1978 | Paquet |
| 4,438,029 A | 3/1984 | Erickson et al. |
| 4,472,385 A | 9/1984 | Brange et al. |
| 4,826,818 A | 5/1989 | Mori et al. |
| 5,204,366 A | 4/1993 | Lavanish et al. |
| 5,310,937 A | 5/1994 | Lavanish et al. |
| 5,929,027 A | 7/1999 | Takama et al. |
| 6,991,798 B1 | 1/2006 | Gschneidner et al. |
| 8,241,620 B2 | 8/2012 | Dahri-Correia et al. |
| 9,089,476 B2 | 7/2015 | Soule et al. |
| 2004/0131583 A1 | 7/2004 | Barritault et al. |
| 2004/0234616 A1 | 11/2004 | Sabetsky |
| 2005/0175611 A1 | 8/2005 | Mahler et al. |
| 2007/0191757 A1 | 8/2007 | Steiner et al. |
| 2007/0235365 A1 | 10/2007 | Pohl et al. |
| 2008/0014250 A1 | 1/2008 | Soula et al. |
| 2008/0039365 A1 | 2/2008 | Steiner et al. |
| 2008/0039368 A1 | 2/2008 | Steiner et al. |
| 2008/0096800 A1 | 4/2008 | Pohl et al. |
| 2008/0234227 A1 | 9/2008 | Soula et al. |
| 2009/0048412 A1 | 2/2009 | Soula et al. |
| 2009/0221805 A1 | 9/2009 | Dahri-Correia et al. |
| 2009/0291114 A1 | 11/2009 | Soula et al. |
| 2010/0137456 A1 | 6/2010 | Soule et al. |
| 2010/0166867 A1 | 7/2010 | Soula et al. |
| 2010/0167991 A1 | 7/2010 | Soule et al. |
| 2010/0184965 A1 | 7/2010 | Soule et al. |
| 2010/0227795 A1 | 9/2010 | Steiner et al. |
| 2010/0249020 A1 | 9/2010 | Soula et al. |
| 2011/0014189 A1 | 1/2011 | Soula et al. |
| 2011/0159068 A1 | 6/2011 | Soula et al. |
| 2011/0172166 A1 | 7/2011 | Charvet et al. |
| 2011/0195025 A1 | 8/2011 | Kett et al. |
| 2011/0195913 A1 | 8/2011 | Charvet et al. |
| 2011/0212901 A1 | 9/2011 | Akiyoshi et al. |
| 2011/0244530 A1 | 10/2011 | Toda et al. |
| 2011/0250653 A1 | 10/2011 | Toda et al. |
| 2011/0318429 A1 | 12/2011 | Ko |
| 2012/0041079 A1 | 2/2012 | Soula et al. |
| 2012/0094902 A1 | 4/2012 | Soula et al. |
| 2012/0178675 A1 | 7/2012 | Pohl et al. |

(Continued)

FOREIGN PATENT DOCUMENTS

| CN | 1613862 A | 5/2005 |
| CN | 101835493 A | 9/2010 |

(Continued)

OTHER PUBLICATIONS

Tse et al, "Translation of DNA into a Library of 13 000 Synthetic Small-Molecule Macrocycles Suitable for in Vitro Selection", Journal of the American Chemical Society, 2008, 130(46), 15611-15626.

(Continued)

*Primary Examiner* — David Lukton

(74) *Attorney, Agent, or Firm* — Oliff PLC

(57) ABSTRACT

A composition, in the form of an aqueous solution, including insulin in hexameric form, at least one substituted anionic compound of non-saccharide structure and at least one polyanionic compound other than the substituted anionic compound.

27 Claims, 8 Drawing Sheets

(56) References Cited

U.S. PATENT DOCUMENTS

| | | |
|---|---|---|
| 2012/0295833 A1 | 11/2012 | Charvet et al. |
| 2012/0309680 A1 | 12/2012 | Charvet et al. |
| 2013/0231281 A1 | 9/2013 | Soula et al. |
| 2014/0142034 A1 | 5/2014 | Soula et al. |
| 2014/0378373 A2 | 12/2014 | Soula et al. |

FOREIGN PATENT DOCUMENTS

| | | |
|---|---|---|
| CN | 101920019 A | 12/2010 |
| CN | 102300586 A | 12/2011 |
| DE | 103 55 251 A1 | 6/2005 |
| EP | 0 093 551 A2 | 11/1983 |
| EP | 0 190 041 A2 | 8/1986 |
| EP | 0 214 826 A2 | 3/1987 |
| EP | 0 441 563 A2 | 8/1991 |
| EP | 0 608 445 A1 | 8/1994 |
| EP | 0 648 495 A2 | 4/1995 |
| EP | 0 681 833 A2 | 11/1995 |
| EP | 0 700 683 A1 | 3/1996 |
| EP | 0 787 497 A2 | 8/1997 |
| EP | 1 623 979 A1 | 2/2006 |
| EP | 2 319 500 A1 | 5/2011 |
| EP | 2 711 077 A1 | 3/2014 |
| FR | 2 224 164 A1 | 10/1974 |
| FR | 2 914 305 A1 | 10/2008 |
| FR | 2 936 800 A1 | 4/2010 |
| FR | 2 943 538 A1 | 10/2010 |
| FR | 2 980 796 A1 | 4/2013 |
| JP | S47-22571 B | 6/1972 |
| JP | S61-12899 B2 | 10/1986 |
| JP | H03-153653 A | 7/1991 |
| JP | H07-82225 A | 3/1995 |
| JP | 2007/177182 A | 7/2007 |
| JP | 2007/177185 A | 7/2007 |
| JP | 2015-010075 A | 1/2015 |
| PL | 149145 B1 | 1/1990 |
| PT | 103003 A | 2/2005 |
| RU | 94026279 A | 6/1996 |
| WO | 88/06599 A1 | 9/1988 |
| WO | 90/10645 A1 | 9/1990 |
| WO | 91/009617 A1 | 7/1991 |
| WO | 96/33699 A1 | 10/1996 |
| WO | 97/49386 A1 | 12/1997 |
| WO | 99/34821 A1 | 7/1999 |
| WO | 00/064845 A1 | 11/2000 |
| WO | 02/20466 A1 | 3/2002 |
| WO | 02/053190 A2 | 7/2002 |
| WO | 03/000202 A2 | 1/2003 |
| WO | 03/014371 A1 | 2/2003 |
| WO | 03/057650 A2 | 7/2003 |
| WO | 2004/050620 A2 | 6/2004 |
| WO | 2004/093833 A2 | 11/2004 |
| WO | 2005/072803 A1 | 8/2005 |
| WO | 2005/089722 A1 | 9/2005 |
| WO | 2007/038773 A1 | 4/2007 |
| WO | 2007/041481 A1 | 4/2007 |
| WO | 2007/074456 A2 | 7/2007 |
| WO | 2007/116143 A1 | 10/2007 |
| WO | 2007/121256 A2 | 10/2007 |
| WO | 2008/038111 A1 | 4/2008 |
| WO | 2008/062466 A2 | 5/2008 |
| WO | 2008/084237 A2 | 7/2008 |
| WO | 2008/124522 A2 | 10/2008 |
| WO | 2008/152106 A1 | 12/2008 |
| WO | 2009/048945 A1 | 4/2009 |
| WO | 2009/048959 A1 | 4/2009 |
| WO | 2009/106386 A1 | 9/2009 |
| WO | 2009/127940 A1 | 10/2009 |
| WO | 2009/136500 A1 | 11/2009 |
| WO | 2010/018324 A1 | 2/2010 |
| WO | 2010/028055 A1 | 3/2010 |
| WO | 2010/041119 A1 | 4/2010 |
| WO | 2010/041138 A2 | 4/2010 |
| WO | 2010/053140 A1 | 5/2010 |
| WO | 2010/058106 A1 | 5/2010 |
| WO | 2010/067613 A1 | 6/2010 |
| WO | 2010/102020 A1 | 9/2010 |
| WO | 2010/122385 A1 | 10/2010 |
| WO | 2010/149772 A1 | 12/2010 |
| WO | 2011/077405 A1 | 6/2011 |
| WO | 2011/098962 A2 | 8/2011 |
| WO | 2012/002450 A1 | 1/2012 |
| WO | 2012/078760 A1 | 6/2012 |
| WO | 2012/124513 A1 | 9/2012 |
| WO | 2012/153070 A1 | 11/2012 |
| WO | 2012/153071 A2 | 11/2012 |
| WO | 2012/157656 A1 | 11/2012 |
| WO | 2013/021143 A1 | 2/2013 |
| WO | 2013/064787 A1 | 5/2013 |
| WO | 2014/076423 A1 | 5/2014 |

OTHER PUBLICATIONS

Liu et al, "Ring Opening Polymerization of Aliphatic Cyclic Carbonates in the Presence of Natural Amino Acids", Journal of Applied Polymer Science, 2008, 107, 3275-3279.

Ramesh & Chandrasekaran, "But-2-ynylbisoxycarbonyl Chloride: A Novel C2-Symmetric Reagent for the Protection of Amines and Amino Acids", Organic Letters, 2005, 7(22), 4947-4950.

Gartner et al, "Multistep small-molecule synthesis programmed by DNA templates", Journal of the American Chemical Society, 2002, 124(35), 10304-10306 and supporting information 1-4.

Kartvelishvili et al, "Amino acid based bioanalogous polymers. Synthesis of novel poly(urethane amide)s based on N, N'-(trimethylenedioxy-dicarbonyl)bis(phenylalanine)", Macromolecular Chemistry and Physics, 1996, 197, 249-257.

Siddique & Duhamel, "Effect of Polypeptide Sequence on Polypeptide Self-Assembly", Langmuir, 2011, 27, 5639-6650.

Coker et al, "Pathways for the Decay of Organic Dichloramines and Liberation of Antimicrobial Chloramine Gases", Chemical Research in Toxicology, 2008, 21(12), 2334-2343.

Sun et al, "Homo-cysteinyl peptide inhibitors of the L1 metallo-R-lactamase, and SAR as determined by combinatorial library synthesis", Bioorganic Medicinal Chemistry Letters, 2006, 16, 5169-5175.

Hong et al, "Determination of inhibitory constants for CPA by competitive spectrophotometry," pp. 247-248.

Schuster et al, "Chymotrypsin-Catalyzed Peptide Synthesis in Ice: Use of Unprotected Amino Acids as Acyl Acceptors", Tetrahedron Letters, 1993, 34(36), 5701-5702.

Votano et al, "Inhibition of Deoxyhemoglobin S Polymerization by Biaromatic Peptides Found to Associate with the Hemoglobin Molecule at a Preferred Site", Biochemistry, 1985, 24(8), 1966-1970.

Gorecki et al, "Peptide Inhibitors of Sickle Hemoglobin Aggregation: Effect of Hydrophobicity", Biochemistry, 1980, 19 (8), 1564-1568.

Behe et al, "Quantitative Assessment of the Noncovalent Inhibition of Sickle Hemoglobin Gelation by Phenyl Derivatives and Other Known Agents", Biochemistry, 1979, 18(19), 4196-4201.

Humme, "Amino acid derivatives hydrolyzable by an enzyme of rennet. III. Peptides", Neth. Milk Dayry J., 1971, 25, 3-14.

Khosla et al, "Synthesis of Mixed N(alpha), N(epsilon)-Peptides of Lysine through direct N(epsilon)-Peptidation", Journal of Scientific and Industrial Research, 1962, 21B, 318-321.

Liwschitz et al, "The Reaction of N-Maleoylamino-acids with Benzylamine", Journal of the Chemical Society, 1962, 3726-3729.

Huffman et al, "Substrate Specificity of Isopenicillin N Synthase", Journal of Medicinal Chemistry, 1992, 35(10), 1897-1914.

Swamy et al, "Synthesis of Iron (III). Cobalt (II), Nickel (II), Copper (II) and Zinc (II) complexes with new quadridentate N,O-donor ligands", Oriental Journal of Chemistry, 2008, 24(3), 1103-1106.

Bergeron et al, "An Investigation of the Impact of Molecular Geometry upon Microcapsule Self-Assembly", Journal of American Chemical Society, 1995, 117(25), 6658-6665.

(56) References Cited

OTHER PUBLICATIONS

Kalra et al, "Ultra-Fast Acting Insulin Analogues.", Recent Patents on Endocrine, Metabolic & Immune Drug Discovery, 2014, 8, pp. 117-123.

Brange J et al, "Insulin analogs with improved pharmacokinetic profiles," Advanced Drug Delivery Reviews, 35, 1999, 307-335.

Tse et al, "Translation of DNA into a Library of 13,000 Synthetic Small-Molecule Macrocycles Suitable for In Vitro Selection," Supporting information S1-S3.

Ramesh et al, "But-2-ynylbisoxycarbonyl Chloride BbcCl: A Novel C2-Symmetric Reagent for the Protection of Amines and Amino Acids," S1-S54.

Fruchart et al, "A new linker fot the synthesis of C-terminal peptide (alpha)-oxo-aldehydes," Tetrahedron Letters, 1999, 40, 6225-6228.

Siddique & Duhamel, Supporting Information for "Effect of Polypeptide Sequence on Polypeptide Self-Assembly," 1-77.

Coker et al, Supporting Information for "Antimicrobial activity of chlorinated amino acids and peptides," 1-11.

U.S. Statutory Invention Registration No. H645, published Jun. 6, 1989.

Lodi et al, "Chiral aminoaci containing acyclic ligands. I. Syntheses and conformations", Tetrahedron, 1982, vol. 38, N°14, pp. 2055-2060.

Marchelli et al, "Chiral aminoaci containing acyclic ligands. II. Compexation of alkaline earth cations", Tetrahedron, 1982, vol. 38, N°14, pp. 2061-2067.

Menzenski et al, "Self-assembly of supramolecular nanostructures from phenylalanine derived bolaamphiphiles", New Journal of Chemistry, 2007, vol. 31, pp. 1674-1680.

Nov. 15, 2016 Search Report and Written Opinion issued in PCT Patent Application No. PCT/EP2015/060132.

"Chemical Book" (downloaded online on Jan. 17, 2017 from URL: <http://www.chemicalbook.com/ProductChemicalPropertiesCB7932982_EN.htm>).

ChEBI-70976 (downloaded online on Jan. 17, 2017 from URL: <http://www.ebi.ac.uk/chebi/searchld.do;jsessionid=0C306-21862A 25C54A3A6EFBB1CFB84DO?chebild=CHEBI:70978>).

"Sigma-Aldrich L-tryptophan" (downloaded online on Jan. 18, 2017 from URL: <http:///www.sigmaaldrich.com/catalog/substance/ltrytophan204237322311?lang=en&region=US#>).

"Sigma-Aldrich L-tyrosine" (downloaded online on Jan. 18, 2017 from URL: <http://www.sigmaaldrich.com/catalog/substance/ltyrosine181198018411?lang=en&region=US>).

Mar. 7, 2017 Office Action issued in U.S. Appl. No. 14/711,378.

Mar. 1, 2017 Office Action issued in U.S. Appl. No. 14/712,328.

Feb. 8, 2017 Office Action issued in Chinese Application No. 201380059092.4.

Mar. 16, 2017 European Office Action issued in European Patent Application No. 13 801 655.5.

Apr. 21, 2017 Office Action issued in Chinese Patent Application No. 201380059136.3.

Apr. 26, 2017 Office Action issued in Japanese Patent Application No. 2015-542338.

Apr. 27, 2017 Office Action issued in Eurasian Patent Application No. 201590937/28.

Baudys, Miroslav et al., "Extending Insulin Action in Vivo by Conjugation to Carboxymethyl Dextran," Bioconugate Chem. 1998, vol. 9, pp. 176-183.

Qiger, Katie et al., "Suppression of Insulin Aggregation by Heparin," Biomacromolecules, 2008, vol. 9, pp. 2338-2344.

Lou, Xianwen et al., "Simulation of size exclusion chromatography for characterization of supramolecular complex: a theoretical study," Journal of Chromatography A, 2004, vol. 1029, pp. 67-75.

Tschantz, William R. et al., "Substrate Binding Is Required for Release of Product from Mammalian Protein Farnesyltransferase," the Journal of Biological Chemistry, 1997, vol. 272, No. 15, pp. 9989-9993.

Oct. 14, 2009 Search Report issued in French Patent Application No. 723351.

Jul. 12, 2010 Written Opinion issued in International Patent Application No. PCT/IB2010/000711.

Jul. 12, 2010 Search Report issued in International Patent Application No. PCT/IB2010/000711.

Sep. 19, 2012 Office Action issued in U.S. Appl. No. 12/662,036.

Arranz et al., "Water-insoluble dextrans by grafting, 3a) Reaction of dextran with butyl isocyanate. Chemical hydrolysis," Makromol. Chem., vol. 188, pp. 2831-2838, 1987.

Carpino et al., "Efficiency in Peptide Coupling: 1-Hydroxy-7-azabenzotriazole vs 3,4-Dihydro-3-hydroxy-4-oxo-1,2,3-benzotriazine," Journal of Organic Chemistry, vol. 60, pp. 3561-3564, 1995.

Caulfield et al., "The Permeability of Glomerular Capillaries to Graded Dextrans," The Journal of Cell Biology, vol. 63, pp. 883-903, 1974.

Chang et al., "Permselectivity of the glomerular capillary wall: III. Restricted transport of polyanions," Kidney International, vol. 8, pp. 212-218, 1975.

Demitras et al, Inorganic Chemistry, Prentice-Hall International Inc., 1972, enclosed pp. 1-5.

Engelmann et al., "Preparation of Starch Carbamates in Homogeneous Phase using Different Mixing Conditions," Starch/Starke, 2001, pp. 560-569, vol. 53, WILEY-VCH Verlag GmbH.

Larsen, "Dextran prodrugs—structure and stability in relation to therapeutic activity," Advanced Drug Delivery Reviews, 1989, pp. 103-154, vol. 3, Elsevier.

Ouari et al, "Synthesis of a Glycolipidic Amphiphilic Nitrone as a New Spin Trap," J. Org. Chem., 1999, pp. 3554-3556, vol. 64, American Chemical Society (with 10 pages of supporting information).

Shen et al., "Synthesis and Characterization of Cellulose Carbamates Having alpha-Amino Acid Moieties," Polymer Bulletin, 2005, pp. 317-322, vol. 55.

Tsai et al., "Synthesis of Amino Acid Ester Isocyanates: Methyl (S)-2-lsocyanato-3-Phenylpropanoate [Benzenepropanoic acid, ?—isocyanato—, methyl ester, (S)]," Organic Syntheses Coll., vol. 10, p. 544, 2004; vol. 78, p. 220, 2002.

Won, "Synthesis of heterobifunctional poly(ethylene glycol) containing an acryloyl group at one end and an isocyanate group at the other end," Polymer Bulletin, 2004, pp. 109-115, vol. 52.

Definition of Phenylalanine, from Croatian English Chemistry Dictionary & Glossary (http://glossary.periodni.com/glossary.php?en=phenylalanine, enclosed, pp. 1-2, Accessed Jan. 17, 2013.

May 3, 2012 French Search Report issued in French Patent Application No, 1158885.

Feb. 22, 2013 Office Action issued in U.S. Appl. No. 12/662,036.

Feb. 28, 2013 Office Action issued in U.S. Appl. No. 13/468,799.

U.S. Appl. No. 12/662,036 to Soula et al., filed Mar. 29, 2010.

U.S. Appl. No. 13/287,793 to Soula et al., filed Nov. 2, 2011.

U.S. Appl. No. 13/468,799 to Charvet et al., filed May 10, 2012.

U.S. Appl. No. 13/468,849 to Charvet et al., filed Jul. 11, 2012.

Heinze et al.; "Functional Polymers Based on Dextran;" Adv. Polym. Sci.; 2006; pp. 199-291; vol. 205; Springer-Verlag Berlin Heidelberg.

May 28, 2014 Office Action issued in U.S. Appl. No. 13/468,849.

Jul. 24, 2013 Office Action issued in U.S. Appl. No. 12/662,036.

R. Janowski, et al., "Two Polymorphs of a Covalent Complex Between Papain and a Diazomethylketone Inhibitor," J. Peptide Res. 64, 2004, pp. 141-150.

Apr. 2, 2013 International Search Report issued in PCT/FR2012/052543.

Jun. 25, 2014 Office Action issued in U.S. Appl. No. 13/668,000.

Definition of derivative and analog, from http://cancerweb.ncl.ao.uk/omd/about.html, pp. 1-5, accessed Jul. 7, 2005.

Polymer Molecular Weight Distribution and Definitions of MW Averages, from www.agilent.com/chem, pp. 1-4, Jun. 10, 2011.

Dec. 12, 2011 French Search Report issued in French Patent Application No. 1154039.

Rudd, Pauline M, et al., "Glycoforms modify the dynamic stability and functional activity of an enzyme." Biochemistry (1994) 33 pp. 17-22.

Memo, Myriad-Mayo guidance, Mar. 2014.

(56) References Cited

OTHER PUBLICATIONS

Bovine ribonuclease b sequence (protein data bank, accession number 1RBJ_, upload Oct. 10, 2012).
Solomons, T.W. Graham; Organic Chemistry, 4th editon, (1988) ISBN 0-471-83659-1, p751.
Roussel et al., "Monolayer lipid membrane-forming dissymmetrical bolaamphiphiles derived from alginate oligosaccharides;" Chem, Communication; 2006; pp. 3622-3624.
Watanabe et al., "Synthesis of lipid A type carboxymethyl derivatives with ether chains instead of ester chains and their LPS-antagonistic" activities;"Carbohydrate" Research; 2003; pp. 47-54; vol. 338.
Song et al., 6-o-Amino-2-o-carboxymethyl Glucopyranoside as Novel Glycoaminoxy Acid Building Block for the Construction of Oligosaccharide Mimetics; Synthesis; 2011; pp. 2761-2766; No. 17.
Tareq et al., "Ieodoglucomides A and B from a Marine-Derived Bacterium Bacillus lichentiformis;" Organic Letters; 2012; pp. 1464-1467; vol. 14, No. 6.
Smoot et al., "Oligosaccharide Synthesis From Conventional Methods to Modern Expeditious Strategies;" Advances in Carbohydrate Chemistry and Biochemistry; 2009; pp. 161-251: vol. 62.
Pal et al "Molecular mechanism of physical gelation of hydrocarbons by fatty acid amides of natural amino acids, "Tetrahedron; 2007; pp. 7334-7348; vol. 63.
Bhaskar et al., "The Selective Silylation of d-Mannitol Assisted by Phenylboronic Acid and the Solid State and Solution Structures of the Intermediate 1,6-bis(silyl) bis(phenylboronates);" Journal of Carbohydrate Chemistry; 2003; pp. 867-879; vol. 22, 9.
Edwards et al., "Dispiroketals in Synthesis (Part 18): Regioselective and Enantioselective Protection of Symmetric Polyol Substrates Using an Eriantiopure (2S,2S)-Dimethyl-bis-dihydropyran; Synlett"; 1995; pp. 898-900; vol. 9.
Ruiz-Pena et al., "Physico-chemical studies of molecular interactions between non-ionic surfactants and bovine serum albumin; Colloids" and Surfaces B: Biointerfaces: 2010: pp. 282-289; vol. 75.
Sawardeker, Jawahar S. et al., "Quantitative determination of monosaccharides as their alditol acetates by gas liquid chromatography." Anal. Chem. (1965) 37 (12) pp. 1602-1604.
Class notes for physical chemistry form the Univesity of Washington http://www.ocean.washington.edu/courses/oc400/Lecture_Notes/CHPT6.pdf, Oct. 2004.
Granger, Elisabeth et al., "Simplified syntheses of complex multifunctional nanomaterials." Chem. Communication (2008) 4792-4794.
Oct. 15, 2014 Office Action issued in U.S. Appl. No. 14/079,437.
May 21, 2015 Office Action issued in U.S. Appl. No. 14/079,437.
U.S. Appl. No. 14/079,437 filed Nov. 13, 2013 in the name of Soula et al.
U.S. Appl. No. 14/581,239 filed on Dec. 23, 2014 in the name of Soula et al.
U.S. Appl. No. 14/079,516 filed on Nov. 13, 2013 in the name of Soula et al.
Dec. 18, 2015 Office Action issued in U.S. Appl. No. 14/079,437.
Wagner, Herman L., "The Mark-Houwink-Sakurada equation for the viscosity of linear polyethylene." J. Phys. Chem. Ref. Data (1985) 14(2) pp. 611-617.
Wayne, Richard P., Principles and applications of photochemistry (1988) ISBN 0-19-855234-3.
Shirnadzu scientific publication SC-AP-GC-0138, downloaded Dec 1, 2015.
Dec. 21, 2015 Office Action issued in U.S. Appl. No. 14/079,516.
Jan. 22, 2016 Office Action issued in U.S. Appl. No. 14/581,239.
Jun. 10, 2016 Office Action Issued in U.S. Appl. No. 14/079,516.
Huus, Kasper et al., "Thermal Dissociation and Unfolding of Insulin", Biochemistry, 2005, vol. 44, pp. 11171-11177.
Uversky, Vladimir N. et al., "Prediction of the Association State of Insulin Using Spectral Parameters", Journal of Pharmaceutical Sciences, Apr. 2003, vol. 92, No. 4, pp. 847-858.
Lindhorst, Thisbe K., "O-Glycoside synthesis", Essentials of Carbohydrate Chemistry and Biochemistry, 2007, pp. 157-208.
Yalpani, Manssur et al., "Selective Chemical Modifications of Dextran", Journal of Polymer Science, 1985, vol. 23, pp. 1395-1405.
Cho, Byung Tae et al. "Direct and indirect reductive amination of aldehydes and ketones with solid acid-activated sodium borohydride under solvent-free conditions", Tetrahedron, 2005, vol. 61, pp. 5725-5734.
Zhang, Tianhong et al., "Novel Polysaccharide Surfactants: Synthesis of Model Compounds and Dextran-Based Surfactants", Macromolecules, 1994, vol. 27, pp. 7302-7308.
Takeoka, Shinji et al., "Physical properties and packing states of molecular assemblies of synthetic glycolipids in aqueous dispersions", Journal of the Chemical Society, Faraday Transactions, 1998, vol. 94, No. 15, pp. 2151-2158.
Sisu, Ioana et al., "Synthesis and structural characterization of amino-functionalized polysaccharides", Central European Journal of Chemistry, 2009, vol. 7, No. 1, pp. 66-73.
Kalra, Sanjay et al., "Ultra-fast acting insulin analogies", Recent Patents on Endocrine, Metabolic & Immune Drug Discovery, 2014, vol. 8-2, pp. 117-123.
May 17, 2016 Office Action Issued in U.S. Appl. No. 14/711,378.
Nov. 15, 2016 International Preliminary Report on Patentability issued in International Application No. PCT/EP2015/060716.
Adediran, S.A. et al., "Deacylation Transition States of a Bacterial DD-Peptidase" Biochemistry, 45, 13074-13082 (2006).
Wu et al.; Reactive Impurities in Excipients: Profiling, Identification and Mitigation of Drug-Excipient Incompatibility; AAPS PharmSciTech; Dec. 2011; pp. 1249-1263; vol. 12, No. 4.
Gildersleeve et al.; Improved Procedure for Direct Coupling of Carbohydrates to Proteins via Reductive Amination; Bioconjug Chem.; Jul. 2008; pp. 1485-1490; vol. 19, No. 7.
U.S. Appl. No. 15/410,524 filed Jan. 19, 2017 in the name of Soula et al.
U.S. Appl. No. 14/711,378 filed May 13, 2015 in the name of Soula et al.
U.S. Appl. No. 14/712,696 filed May 14, 2015 in the name of Soula et al.
U.S. Appl. No. 14/712,328 filed May 14, 2015 in the name of Soula.
U.S. Appl. No. 15/353,522 filed Nov. 16, 2016 in the name of Soula et al.
Siddique & Duhamel, Supporting Information for "Effect of Polypeptide Sequence on Polypeptide Self-Assembly", Langmuir, 2011, 27(11), 6639-6650.
Apr. 27, 2016 Office Action issued in Chinese Application No. 201380059092.4.
Nov. 15, 2016 Search Report and Written Opinion issued in PCT Patent Application No. PCT/EP2015/060820.

FAST-ACTING INSULIN COMPOSITION COMPRISING A SUBSTITUTED ANIONIC COMPOUND AND A POLYANIONIC COMPOUND

The present invention relates to a fast-acting insulin composition comprising a substituted anionic compound and a polyanionic compound.

Since the production of insulin by genetic engineering, at the start of the 1980s, diabetic patients have been benefiting from human insulin for their treatment. This product has greatly improved this therapy, since the immunological risks associated with the use of nonhuman insulin, in particular from pigs, is eliminated. However, human insulin injected subcutaneously has a hypoglycemiant effect only after 60 minutes, which means that diabetic patients treated with human insulin must perform the injection 30 minutes before a meal.

One of the problems to solve for improving the health and comfort of diabetic patients is that of providing them with insulin formulations that can provide a faster hypoglycemiant response than that of human insulin and, if possible, approaching the physiological response of a healthy person. The secretion of endogenous insulin in a healthy individual is immediately triggered by the increase in glycemia. The object is to minimize the delay between the injection of insulin and the start of a meal.

It is nowadays accepted that the provision of such formulations is useful in order for the medical care patient to be as good as possible.

Genetic engineering has made it possible to provide a response with the development of rapid insulin analogs. These insulins are modified on one or two amino acids so as to be more rapidly absorbed into the blood compartment after a subcutaneous injection. These insulins lispro (Humalog®, Lilly), aspart (Novolog®, Novo Nordisk) and glulisine (Apidra®, Sanofi Aventis) are stable insulin solutions with a faster hypoglycemiant response than that of human insulin. Consequently, patients treated with these rapid insulin analogs can perform the insulin injections as little as 15 minutes before a meal.

The principle of rapid insulin analogs is to form hexamers at a concentration of 100 IU/mL to ensure the stability of the insulin in the commercial product while at the same time promoting the very rapid dissociation of these hexamers into monomers after subcutaneous injection so as to obtain a rapid action.

Human insulin as formulated in its commercial form does not make it possible to obtain a hypoglycemiant response that is close in kinetic terms to the physiological response generated by the start of a meal (increase in glycemia), since, at the working concentration (100 IU/mL), in the presence of zinc and other excipients such as phenol or m-cresol it assembles to form a hexamer whereas it is active in monomeric and dimeric form. Human insulin is prepared form of hexamers to be stable for close to 2 years at 4° C., since, in the form of monomers, it has a very high propensity to aggregate and then to fibrillate, which causes it to lose its activity. Furthermore, in this aggregated form, it presents an immunological risk for the patient.

Dissociation of the hexamers into dimers and of the dimers into monomers delays its action by up to 20 minutes when compared with a rapid insulin analog (Brange J., et al., Advanced Drug Delivery Review, 35, 1999, 307-335).

In addition, the kinetics of passage of insulin analogs into the blood and the kinetics of glycemia reduction are not optimal, and there is a real need for a formulation that has an even shorter action time so as to approach the secretion kinetics of endogenous insulin in healthy people.

The company Biodel has proposed a solution to this problem with a human insulin formulation comprising EDTA and citric acid, as described in patent application US 2008/39365. By virtue of the capacity of EDTA to complex zinc atoms and by virtue of the interactions of citric acid with the cationic zones present on the surface of insulin, these agents are described as destabilizing the hexameric form of insulin and thus of reducing its action time.

However, such a formulation especially has the drawback of disassociating the hexameric form of insulin, which is the only stable form that is capable of satisfying the stability requirements of the pharmaceutical regulation.

Patent application PCT WO 2010/122385 and WO 2013/064787, in the name of the Applicant, are also known, which describe formulations of human insulin or insulin analogs and of a substituted polysaccharide or oligosaccharide comprising carboxyl groups.

However, the requirements entailed by the chronic and intensive use or even the pediatric use of such formulations lead a person skilled in the art to seek to use excipients whose molar mass and size are as small as possible, to facilitate their elimination.

The polysaccharides described in patent applications WO 2010/122385 A1 and US 2012/094902 A1 as excipients are compounds consisting of chains whose lengths are statistically variable and which have a great richness of sites of possible interaction with protein active principles. This richness might induce a lack of specificity in terms of interaction, and a smaller and better defined molecule might make it possible to be more specific in this subject.

In addition, a molecule with a well-defined backbone is generally more easily traceable (for example MS/MS) in biological media during pharmacokinetic or ADME (administration, distribution, metabolism, elimination) experiments when compared with a polymer which generally gives a very diffuse and noisy signal in mass spectrometry.

On the contrary, it is not excluded for a well-defined and shorter molecule to be liable to have a deficit of possible sites of interaction with protein active principles. Specifically, on account of their small size, they do not have the same properties as polymers of polysaccharide type, since there may be a loss of the polymer effect.

The Applicant has, however, succeeded in developing formulations that are capable of accelerating insulin by using a substituted ionic compound in combination with a polyanionic compound.

Furthermore, as in the case of the use of polysaccharides, the hexameric nature of insulin is not affected, and thus the stability of the formulations is not affected, as is moreover confirmed by the examples of the state of association of human insulin or of the insulin analog lispro on circular dichroism in the presence of substituted anionic compounds according to the invention, and optionally of polyanionic compound.

The present invention makes it possible to solve the various problems outlined above, entirely or partly, since it especially makes it possible to prepare a formulation of insulin, human or analog, which is capable, after administration, of accelerating the passage of the human insulin or of the analogs thereof into the blood and of more rapidly reducing glycemia when compared with the corresponding commercial insulin products.

The invention consists of a composition, in the form of an aqueous solution, comprising insulin in hexameric form, at least one substituted anionic compound of non-saccharide structure and at least one polyanionic compound other than said substituted anionic compound.

In one embodiment, the pH of the composition is between 6 and 8.

The term "aqueous solution" means a solution within the meaning of the European Pharmacopea.

The solution according to the invention may thus correspond to European Pharmacopea 8.0, which defines that an injectable preparation of soluble insulin has the characters of a colorless, non-opalescent liquid, free of foreign substances; traces of very fine sediments may become deposited during storage (01/2008: 0834).

The solution according to the invention may be a non-opalescent, or even clear, liquid.

According to European Pharmacopea 8.0 in point 2.2.1, 0 liquid is considered as being clear when it has an opalescence that is no more pronounced than that of the control suspension I, which has an opalescence value of 3 NTU. The opalescence of the solution may be determined by the visual method and/or by the instrumental method, known as turbidimetry. Said methods are defined in European Pharmacopea 8.0, in point 2.2.1.

Most particularly, the solution according to the invention has a turbidity of less than or equal to 3 NTU according to the various methods described in European Pharmacopea 8.0 in point 2.2.1.

The term "non-saccharide structure" means that these compounds do not contain in their structure any saccharide units, whether in cyclic form or in open, reduced or oxidized form.

The term "saccharide unit" denotes pentoses, hexoses, uronic acids and N-acetyl hexosamines in cyclic form or in open, oxidized or reduced form.

In one embodiment, the compositions according to the invention are sterilized by filtration on a 0.22 μm membrane, for example by filtration on an SLGV033RS, Millex-GV membrane from Millipore, a 0.22 μm PVDF membrane.

The substituted anionic compound of non-saccharide structure comprises a hydrocarbon-based radical R which is at least monovalent comprising from 1 to 12 carbon atoms, optionally comprising at least one function chosen from ether, alcohol and carboxylic acid functions,
said hydrocarbon-based radical R bearing at least one radical AA resulting from an aromatic amino acid comprising a phenyl group or an indole group, which is substituted or not substituted, or an aromatic amino acid derivative comprising a phenyl group or an indole group, which is substituted or not substituted, said radical AA being linked to the hydrocarbon-based radical R:
  either directly via a function F chosen from amide, carbamate and urea functions, resulting from a reaction between the amine of the aromatic amino acid and a function of the precursor of the hydrocarbon-based radical R chosen from carboxylic acid, amine and alcohol functions,
  or via a spacer E which is an at least divalent radical, comprising from 2 to 6 carbon atoms, E being linked, on the one hand, to the hydrocarbon-based radical R via a function F' chosen from amide, carbamate and urea functions, and linked, on the other hand, to the radical AA via a function F'' chosen from amide, carbamate and urea functions, resulting from a reaction between the amine of the aromatic amino acid and a function of the spacer E chosen from carboxylic acid, amine and alcohol functions, said substituted anionic compound comprising at least two carboxylic acid functions in the form of salts of alkali metal cations chosen from the group consisting of $Na^+$ and $K^+$.

In one embodiment, E is an at least divalent linear or branched alkyl radical.

In one embodiment, E represents a saturated or unsaturated, linear or branched hydrocarbon-based radical comprising from 2 to 6 carbon atoms, optionally comprising at least one function chosen from alcohol and carboxylic acid functions.

The substituted anionic compound of non-saccharide structure comprises a hydrocarbon-based radical R which is at least monovalent comprising from 3 to 12 carbon atoms, optionally comprising at least one function chosen from ether, alcohol and carboxylic acid functions,
said hydrocarbon-based radical R bearing at least one radical AA resulting from an aromatic amino acid comprising a phenyl group or an indole group, which is substituted or not substituted, or an aromatic amino acid derivative comprising a phenyl group or an indole group, which is substituted or not substituted, said radical AA being linked to the hydrocarbon-based radical R:
  either directly via a function F chosen from amide, carbamate and urea functions, resulting from a reaction between the amine of the aromatic amino acid and a function of the precursor of the hydrocarbon-based radical R chosen from carboxylic acid, amine and alcohol functions,
  or via a spacer E which is an at least divalent radical, comprising from 2 to 6 carbon atoms, E being linked, on the one hand, to the hydrocarbon-based radical R via a function F' chosen from amide, carbamate and urea functions, and linked, on the other hand, to the radical AA via a function F'' chosen from amide, carbamate and urea functions, resulting from a reaction between the amine of the aromatic amino acid and a function of the spacer E chosen from carboxylic acid, amine and alcohol functions, said substituted anionic compound comprising at least two carboxylic acid functions in the form of salts of alkali metal cations chosen from the group consisting of $Na^+$ and $K^+$.

In one embodiment, the substituted anionic compound corresponds to formula I below:

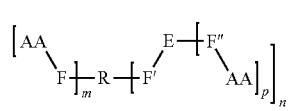

Formula I wherein
  R represents a saturated or unsaturated, linear, branched or cyclic hydrocarbon-based radical comprising from 1 to 12 carbon atoms, optionally comprising at least one function chosen from ether, alcohol and carboxylic acid functions.
  AA is a radical resulting from an aromatic amino acid comprising a phenyl group or an indole group, which is substituted or not substituted, or an aromatic amino acid derivative comprising a phenyl group or an indole group, which is substituted or not substituted, said radical AA bearing at least one free acid function,
  E represents an at least divalent radical, comprising from 2 to 6 carbon atoms,
  F, F' and F'' represent, independently of each other, a function chosen from amide, carbamate and urea functions, F and F″ being functions resulting from a reaction involving the amine of the aromatic amino acid, the precursor of the radical AA, F′ being a function involving a reactive function of the precursor of R and a reactive function of the precursor of E, p being an integer between 1 and 3, m is an integer between 0 and 6; n is an integer between 0 and 6; m+n is an integer between 1 and 6;

said compound comprising at least two carboxylic acid functions in the form of a salt of an alkali metal chosen from $Na^+$ and $K^+$.

In one embodiment, the at least 2 carboxylic acid functions in the form of a salt of an alkali metal are borne by the radicals R, AA or E.

In one embodiment, the at least 2 carboxylic acid functions in the form of a salt of an alkali metal are borne by the radicals R and E.

In one embodiment, the at least 2 carboxylic acid functions in the form of a salt of an alkali metal are borne by the radicals R and AA.

In one embodiment, the at least 2 carboxylic acid functions in the form of a salt of an alkali metal are borne by the radicals AA and E.

In one embodiment, the at least 2 carboxylic acid functions in the form of a salt of an alkali metal are borne by the radical R.

In one embodiment, the at least 2 carboxylic acid functions in the form of a salt of an alkali metal are borne by the radical AA.

In one embodiment, the at least 2 carboxylic acid functions in the form of a salt of an alkali metal are borne by the radical E.

In one embodiment, if m+n*p=1, then R comprises at least one carboxylic acid function. * represents the mathematical multiplication sign.

In one embodiment, E is an at least divalent, linear or branched alkyl radical.

In one embodiment, E represents a saturated or unsaturated, linear or branched hydrocarbon-based radical comprising from 2 to 6 carbon atoms, optionally comprising at least one function chosen from alcohol and carboxylic acid functions.

In one embodiment, F is chosen from amide and carbamate functions.

In one embodiment, F is an amide function.

In one embodiment, F is a carbamate function.

In one embodiment, F′ is a urea function.

In one embodiment, F′ is an amide function.

In one embodiment, F′ is a carbamate function.

In one embodiment, F and F′ are chosen from amide and carbamate functions.

In one embodiment, F and F′ are amide functions.

In one embodiment, F and F′ are carbamate functions.

In one embodiment, F″ is a urea function.

In one embodiment, F″ is an amide function.

In one embodiment, F″ is a carbamate function.

In one embodiment, F′ is an amide function and F″ is a carbamate function.

In one embodiment, the substituted anionic compound corresponds to formula I below:

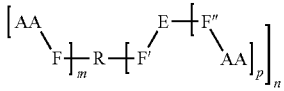

Formula I wherein

R represents a hydrocarbon-based radical comprising from 3 to 12 carbon atoms, optionally comprising at least one function chosen from ether, alcohol and carboxylic acid functions, AA is a radical resulting from an aromatic amino acid comprising a phenyl group or an indole group, which is substituted or not substituted, or an aromatic amino acid derivative comprising a phenyl group or an indole group, which is substituted or not substituted, said radical AA bearing a free acid function, E represents a radical comprising from 2 to 6 carbon atoms, F, F′ and F″ represent, independently of each other, a function chosen from amide, carbamate and urea functions, F and F″ being functions resulting from a reaction involving the amine of the aromatic amino acid, a precursor of the radical AA, p being an integer between 1 and 3, m is an integer between 0 and 6; n is an integer between 0 and 6; m+n is an integer between 1 and 6;

said compound comprising at least two carboxylic acid functions in the form of a salt of an alkali metal chosen from $Na^+$ and $K^+$.

In one embodiment, the at least 2 carboxylic acid functions in the form of a salt of an alkali metal are borne by the radicals R, AA or E.

In one embodiment, the at least 2 carboxylic acid functions in the form of a salt of an alkali metal are borne by the radicals R and E.

In one embodiment, the at least 2 carboxylic acid functions in the form of a salt of an alkali metal are borne by the radicals R and AA.

In one embodiment, the at least 2 carboxylic acid functions in the form of a salt of an alkali metal are borne by the radicals AA and E.

In one embodiment, the at least 2 carboxylic acid functions in the form of a salt of an alkali metal are borne by the radical R.

In one embodiment, the at least 2 carboxylic acid functions in the form of a salt of an alkali metal are borne by the radical AA.

In one embodiment, the at least 2 carboxylic acid functions in the form of a salt of an alkali metal are borne by the radical E.

In one embodiment, E is an at least divalent linear or branched alkyl radical.

In one embodiment, E represents a saturated or unsaturated, linear or branched hydrocarbon-based radical comprising from 2 to 6 carbon atoms, optionally comprising at least one function chosen from alcohol and carboxylic acid functions.

In one embodiment, the radical R may comprise from 4 to 10 carbon atoms, in particular from 4 to 6 carbon atoms.

The radical R may be a linear, branched or cyclic hydrocarbon-based radical, and may be saturated or unsaturated. In particular, the radical R is a saturated linear hydrocarbon-based radical.

In one embodiment, m+n=6.

In one embodiment, m+n=5.

In one embodiment, m+n=4.

In one embodiment, m+n=3.

In one embodiment, m+n=2.

In one embodiment, m+n=1.

In one embodiment, the substituted anionic compound is chosen from the compounds of formula I wherein the radical —R— is chosen from radicals comprising 1 to 12 carbon atoms, of formula IV:

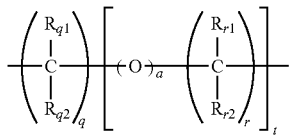

Formula IV wherein q and r are integers between 0 and 12, r is an integer between 0 and 3 and $1 \leq q+r*t \leq 12$, a is equal to 0 or 1, the groups $R_{q1}$, $R_{q2}$, $R_{r1}$ and $R_{r2}$ are, independently of each other, chosen from —H, —OH and —COOH. If a=0 then t=0. When $q \geq 1$ and/or $t \geq 1$, then the radicals $R_{q1}$ and $R_{q2}$ and the radicals $R_{r1}$ and $R_{r2}$ are identical or different from one carbon to another.

In one embodiment, the radical —R— is chosen from the radicals of formula IV wherein t=0, a=0 and r=0, represented by formula V:

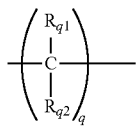

Formula V wherein q is an integer between 1 and 12 and the groups $R_{q1}$ and $R_{q2}$ are, independently of each other, chosen from —H, —OH and —COOH.

In one embodiment, the substituted anionic compound is chosen from the compounds of formula I wherein the radical —R— is a radical resulting from a compound comprising 1 to 12+(m+n) carbon atoms.

In one embodiment, the substituted anionic compound is chosen from the compounds of formula I wherein m+n=6 and the radical —R— is a radical resulting from a compound comprising 2 to 18 carbon atoms.

In one embodiment, the substituted anionic compound is chosen from the compounds of formula I wherein m+n=4 and the radical —R— is a radical resulting from a compound comprising 2 to 16 carbon atoms.

In one embodiment, the substituted anionic compound is chosen from the compounds of formula I wherein m+n=2 and the radical —R— is a radical resulting from a compound comprising 2 to 14 carbon atoms, of formula VI:

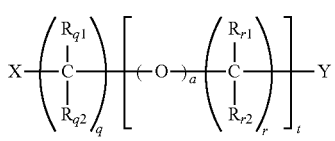

Formula VI wherein q and r are integers between 0 and 12 and $1 \leq q+r*t \leq 12$, a is 0 or 1, the groups $R_{q1}$, $R_{q2}$, $R_{r1}$ and $R_{r2}$ are, independently of each other, chosen from —H, —OH and —COOH and —X and —Y, which may be identical or different, are chosen from —COOH, —OH and —NH₂. If a=0 then t=0. When $q \geq 1$ and/or $t \geq 1$, then the radicals $R_{q1}$ and $R_{q2}$ and the radicals $R_{r1}$ and $R_{r2}$ are identical or different from one carbon to another.

—X and —Y are reactive functions that react with the precursor of E or of AA to form, respectively, F' or F.

In one embodiment, the substituted anionic compound is chosen from the compounds of formula I wherein m+n=1 and the radical —R— is a radical resulting from a compound comprising 1 to 13 carbon atoms, of formula VI above, and if —X or —Y is —NH₂, then it is the group that reacts with the precursor of E or of AA to form F' or F.

In one embodiment, the radical —R— is a radical resulting from a compound of formula VI wherein t=0, a=0 and r=0, represented by formula VII:

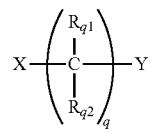

Formula VII wherein q is an integer between 1 and 12 and the groups $R_{q1}$ and $R_{q2}$ are, independently of each other, chosen from —H, —OH and —COOH, and —X and —Y, which may be identical or different, are chosen from —COOH, —OH and —NH₂.

—X and —Y are reactive functions that react with the precursor of E or of AA to form, respectively, F' or F.

In one embodiment, the substituted anionic compound is chosen from the compounds of formula I wherein m+n=1 and the radical —R— is a radical resulting from a compound comprising 1 to 13 carbon atoms, of formula VI above, and if —X or —Y is —NH₂, then it is the group that reacts with the precursor of E or of AA to form F' or F.

In one embodiment, the precursor of R is chosen from the precursors of formula VI or VII wherein —X and —Y, which may be identical or different, are chosen from —COOH and —OH.

The radical R may comprise at least one function chosen in particular from alcohol and carboxylic acid functions.

According to one embodiment, the radical R comprises o carboxylic acid functions, o being an integer between 1 and 3, o especially being equal to 1 or 2, and in particular o is equal to 1.

According to another embodiment, the radical R is free of carboxylic acid functions.

According to one embodiment, the radical R comprises at least one alcohol function, and in particular comprises from 1 to 4 alcohol functions, especially 1 or 2 alcohol functions.

According to another embodiment, the radical R is free of alcohol functions.

According to one embodiment, the radical R comprises 1 or 2 alcohol functions and 1 carboxylic acid function.

The radical R may originate from a polycarboxylic acid, especially from a dicarboxylic acid.

According to one embodiment, all the carboxylic acid functions of the polycarboxylic acid are involved in the functions F and F'.

Thus, according to this embodiment, all the carboxylic acid functions of the precursor of R are involved in the functions F and F'.

According to another embodiment, all the carboxylic acid functions of the polycarboxylic acid are not involved in the functions F and F'.

Thus, according to this embodiment, all the carboxylic acid functions of the precursor of R are not involved in the functions F and F'.

In particular, 1 or 2 carboxylic acid functions are not involved in the functions F and F', most particularly 1 carboxylic acid function is not involved in the functions F and F'.

The radical R may be resulting from a dicarboxylic acid chosen from propanedioic acid, butanedioic acid (or succinic acid), tartaric acid, malic acid, pentanedioic acid, hexanedioic acid (or adipic acid), heptanedioic acid, octanedioic acid, nonanedioic acid, butenedioic acid, pentenedioic acid and hexadienedioic acid.

In particular, the radical R is resulting from a dicarboxylic acid chosen from butanedioic acid (or succinic acid), tartaric acid, malic acid, pentanedioic acid and hexanedioic acid (or adipic acid).

Even more particularly, the radical R is resulting from a dicarboxylic acid chosen from butanedioic acid (or succinic acid) and tartaric acid.

The radical R may be resulting from an amino acid.

In particular, the radical R may be resulting from an amino acid chosen from glutamic acid and aspartic acid.

The radical R may be resulting from a diol. The diol may be chosen from ethylene glycol, diethylene glycol, triethylene glycol and tetraethylene glycol, propanediol, butanediol, pentanediol, hexanediol, heptanediol and octanediol.

In particular, the radical R of the substituted anionic compound is resulting from a dicarboxylic acid, an amino acid or a diol.

The radical AA is resulting from an aromatic amino acid comprising a phenyl or an indole, which is substituted or not substituted, or an aromatic amino acid derivative comprising a phenyl or an indole, which is substituted or not substituted. Most particularly, the radical AA is resulting from an aromatic amino acid comprising a phenyl or an indole, which is substituted or not substituted.

The radical AA is linked to the radical E or to the radical R via a function F or F''' involving the amine of the aromatic amino acid or of an aromatic amino acid derivative.

The term "aromatic amino acid comprising a substituted or not substituted phenyl or indole" means a compound comprising from 7 to 20 carbon atoms, a phenyl or an indole, which is substituted or not substituted, an amine function and an acid function.

The term "aromatic amino acid derivative" means decarboxylated derivatives, amino alcohol or amino amide derivatives corresponding to the aromatic amino acids comprising a phenyl or an indole, which is substituted or not substituted. The derivatives of said aromatic amino acid is comprising a phenyl or an indole, which is substituted or not substituted, may be chosen in particular from amino alcohols and amino amides.

According to one embodiment, AA is resulting from an aromatic amino acid comprising a phenyl or an indole, which is substituted or not substituted, chosen from alpha or beta amino acids. The aromatic amino acids comprising a phenyl or an indole, which is substituted or not substituted, may be chosen from the group consisting of phenylalanine, alpha-methylphenylalanine, 3,4-dihydroxyphenylalanine, alpha-phenylglycine, 4-hydroxyphenylglycine, 3,5-dihydroxyphenylglycine, tyrosine, alpha-methyltyrosine, O-methyltyrosine and tryptophan.

According to one embodiment, the aromatic amino acid comprising a phenyl or an indole, which is substituted or not substituted, is a natural amino acid, chosen especially from phenylalanine, tyrosine and tryptophan, most particularly phenylalanine.

The aromatic amino acids comprising a substituted or not substituted phenyl or indole, and the derivatives thereof may, where appropriate, be in levorotatory or dextrorotatory form or in racemic form. In particular, they are in levorotatory form.

According to one embodiment, the substituted anionic compound comprises from 1 to 6 radicals AA and in particular from 1 to 3 radicals AA.

In one embodiment, the radical E is resulting from a linear or branched alkyl compound comprising at least two functions chosen from the group consisting of —OH, —COOH and —NH$_2$.

In particular, the radical E is resulting from a compound comprising from 2 to 6 carbon atoms, and optionally comprising 1 or 2 carboxylic acid functions and/or 1, 2 or 3 alcohol functions.

The radical E is an at least divalent radical, in particular divalent, trivalent or tetravalent.

According to one embodiment, the radical E is resulting from a linear or branched alkyl compound, optionally bearing one or two carboxylic acid functions.

The radical E may be resulting from an amino alcohol, an amino diol or an amino triol, in particular chosen from the group consisting of trishydroxymethylaminomethane, also known as 2-amino-2-hydroxymethyl-1,3-propanediol or TRIS, serinol and threoninol.

According to one embodiment, when the radical E is resulting from an amino diol or an amino triol, it is, respectively, substituted with 2 or 3 radicals AA.

According to another embodiment, the radical E may be resulting from an amino acid comprising two carboxylic acid functions, in particular aspartic acid or glutamic acid. In this embodiment, the radical E may be linked to one or two radicals AA.

In one embodiment, the substituted anionic compound is chosen from the compounds of formula I wherein the precursor of the radical E does not comprise any —NH$_2$ functions.

In one embodiment, the substituted anionic compound is chosen from the compounds of formula I wherein the radical E is different from the radical R.

In one embodiment, the substituted anionic compound is chosen from the compounds of formula I wherein the precursor of the radical E is different from the precursor of the radical R.

According to one embodiment, the substituted anionic compound comprises from 2 to 8, especially from 2 to 6 or even from 2 to 4 carboxylic acid functions.

According to one embodiment, $m+n*p=1$.
According to one embodiment, $m+n*p=2$.
According to one embodiment, $m+n*p=3$.
According to one embodiment, $m+n*p=4$.
According to one embodiment, $m+n*p=5$.
According to one embodiment, $m+n*p=6$.
According to one embodiment, $m+n*p=7$.
According to one embodiment, $m+n*p=8$.

The calculation $m+n*p$ gives the number of carboxylate functions provided by AA. When the radical R comprises free carboxylate functions, then the total number of free carboxylate functions is greater than $m+n*p$.

According to one embodiment, the substituted anionic compound does not comprise a radical AA linked via a spacer E. Thus, the substituted anionic compound may correspond to formula I wherein $n=0$.

According to one embodiment, the substituted anionic compound does not comprise a radical AA linked via a spacer E, and the substituted anionic compound may correspond to formula I wherein n=0 and corresponds to formula II:

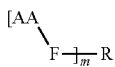

Formula II

AA, F and R have the definitions given above,
1≤m≤6.

In one embodiment, the substituted anionic compound is chosen from the anionic compounds of formula II wherein m=1:

Formula VIII

In one embodiment, the substituted anionic compound is chosen from the anionic compounds of formula II wherein m=2:

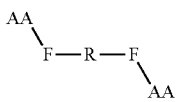

Formula IX

According to one embodiment, the substituted anionic compound does not comprise a radical AA linked via the function F to the radical R. Thus, the substituted anionic compound may correspond to formula I wherein m=0.

According to one embodiment, the substituted anionic compound does not comprise a radical AA linked via the function F to the radical R, and the substituted anionic compound may correspond to formula I wherein m=0 and corresponds to formula III:

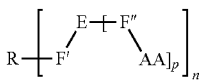

Formula III

AA, E, F', F", p and R have the definitions given above,
1≤n≤6.

In one embodiment, the substituted anionic compound is chosen from the anionic compounds of formula III wherein n=1:

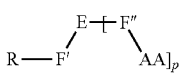

Formula X

In one embodiment, the substituted anionic compound is chosen from the anionic compounds of formula III wherein n=2:

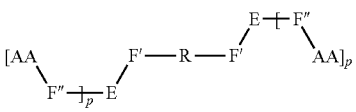

Formula XI

In one embodiment, the substituted anionic compound is chosen from the anionic compounds of formula III, X or XI wherein p=1.

In one embodiment, the substituted anionic compound is chosen from the anionic compounds of formula III, X or XI wherein p=2.

In one embodiment, the substituted anionic compound is chosen from the anionic compounds of formula III, X or XI wherein p=3.

In one embodiment, the substituted anionic compound is chosen from the anionic compounds of formula III or X wherein n=1 and p=3.

In one embodiment, the substituted anionic compound is chosen from the anionic compounds of formula III wherein n=2 and p=3.

According to one embodiment, the substituted anionic compound corresponds to formula I wherein the radical AA is resulting from phenylalanine and the radical R is resulting from tartaric acid, succinic acid or an amino acid chosen from aspartic acid and glutamic acid, the radical R is especially resulting from tartaric acid or succinic acid and in particular n=0 and m=1.

According to one embodiment, the substituted anionic compound corresponds to formula I wherein the radical AA is resulting from phenylalanine and the radical R is resulting from succinic acid, tartaric acid or an amino acid chosen from aspartic acid and glutamic acid, n=0 and m=1.

According to one embodiment, the substituted anionic compound corresponds to formula I wherein the radical AA is resulting from phenylalanine, n=0, m=1, the radical R is resulting from tartaric acid or succinic acid, in particular from tartaric acid, and bears an acid function.

According to one embodiment, the substituted anionic compound corresponds to formula I wherein the radical AA is resulting from phenylalanine, m=0, n=1 or 2, especially n=1, p=3 and E is resulting from TRIS. In particular, the radical R is resulting from tartaric or succinic acid and comprises an acid function or R is a radical originating from a diol.

According to one embodiment, the substituted anionic compound corresponds to formula I wherein the radical AA is resulting from phenylalanine, m=0, n=1 or 2, especially n=1, p=2 and E is resulting from aspartic acid or glutamic acid. In particular, the radical R is resulting from tartaric or succinic acid and comprises an acid function or the radical R is a radical originating from a diol.

According to one embodiment, the substituted anionic compound corresponds to formula I wherein the radical AA is resulting from phenylalanine, m=0, n=1, 2 or 3, especially n=3, p=2 and E is resulting from aspartic acid or glutamic acid. In particular, the radical R is resulting from aspartic acid or glutamic acid.

Most particularly, the substituted anionic compound corresponds to formula I wherein the radical R is resulting from succinic acid and comprises a carboxylic acid, m=0, n=1, p=3, E is resulting from TRIS, F' is an amide function, the radical AA is resulting from phenylalanine, and F" is a urea function.

Most particularly, the substituted anionic compound corresponds to formula I wherein the radical R is resulting from succinic acid and comprises a carboxylic acid, m=0, n=1, p=3, E is resulting from TRIS, F' is an amide function, the radical AA is resulting from phenylalanine, and F" is a carbamate function.

Most particularly, the substituted anionic compound corresponds to formula I wherein the radical R is resulting from tartaric acid and comprises a carboxylic acid, m=1, n=0, F is an amide function, and the radical AA is resulting from phenylalanine.

Most particularly, the substituted anionic compound corresponds to formula I wherein the radical R is resulting from succinic acid and comprises a carboxylic acid, m=1, n=0, F is an amide function, and the radical AA is resulting from phenylalanine.

Most particularly, the substituted anionic compound corresponds to formula I wherein the radical R is resulting from tartaric acid and comprises a carboxylic acid, m=0, n=1, p=3, E is resulting from TRIS, F' is an amide function, the radical AA is resulting from phenylalanine, and F" is a carbamate function.

Most particularly, the substituted anionic compound corresponds to formula I wherein the radical R is resulting from tartaric acid and comprises a carboxylic acid, m=0, n=1, p=2, E is resulting from aspartic acid, F' is an amide function, the radical AA is resulting from phenylalanine, and F" is an amide function.

In one embodiment, the mole ratios of substituted anionic compound/insulin are between 0.6 and 300.

In one embodiment, the mole ratios of substituted anionic compound/insulin are between 0.6 and 120.

In one embodiment, the mole ratios of substituted anionic compound/insulin are between 0.7 and 80.

In one embodiment, the mole ratios of substituted anionic compound/insulin are between 1.4 and 60.

In one embodiment, the mole ratios of substituted anionic compound/insulin are between 1.9 and 40.

In one embodiment, the mole ratios of substituted anionic compound/insulin are between 2.3 and 40.

In one embodiment, the mole ratio of substituted anionic compound/insulin is equal to 8, 12 or 16.

In the above mole ratios, the number of moles of insulin is understood as being the number of moles of insulin monomer.

In one embodiment, the mass ratios of substituted anionic compound/insulin are between 0.5 and 30.

In one embodiment, the mass ratios of substituted anionic compound/insulin are between 0.5 and 20.

In one embodiment, the mass ratios of substituted anionic compound/insulin are between 0.5 and 10.

In one embodiment, the mass ratios of substituted anionic compound/insulin are between 0.6 and 7.

In one embodiment, the mass ratios of substituted anionic compound/insulin are between 1.2 and 5.

In one embodiment, the mass ratios of substituted anionic compound/insulin are between 1.6 and 4.

In one embodiment, the mass ratios of substituted anionic compound/insulin are between 2 and 4.

In one embodiment, the mass ratio of substituted anionic compound/insulin is 2, 3, 4 or 6.

In one embodiment, the insulin is human insulin.

The term "human insulin" means an insulin obtained by synthesis or recombination, the peptide sequence of which is the sequence of human insulin, including the allelic variations and homologs.

In one embodiment, the insulin is a recombinant human insulin as described in the European pharmacopea and the American pharmacopea.

In one embodiment, the insulin is an insulin analog.

The term "insulin analog" means a recombinant insulin whose primary sequence contains at least one modification relative to the primary sequence of human insulin.

In one embodiment, the insulin analog is chosen from the group consisting of the insulin lispro (Humalog®), the insulin aspart (Novolog®, Novorapid®) and the insulin glulisine (Apidra®).

In one embodiment, the insulin analog is the insulin lispro (Humalog®).

In one embodiment, the insulin analog is the insulin aspart (Novolog®, Novorapid®).

In one embodiment, the insulin analog is the insulin glulisine (Apidra®).

In one embodiment, the insulin is in hexameric form.

In one embodiment, the pharmaceutical composition is characterized in that the insulin concentration is between 240 and 3000 µM (40 to 500 IU/mL).

In one embodiment, the pharmaceutical composition is characterized in that the insulin concentration is between 600 and 3000 µM (100 to 500 IU/mL).

In one embodiment, the pharmaceutical composition is characterized in that the insulin concentration is between 600 and 2400 µM (100 to 400 IU/mL).

In one embodiment, the pharmaceutical composition is characterized in that the insulin concentration is between 600 and 1800 µM (100 to 300 IU/mL).

In one embodiment, the pharmaceutical composition is characterized in that the insulin concentration is between 600 and 1200 µM (100 to 200 IU/mL).

One embodiment concerns a pharmaceutical composition characterized in that the insulin concentration is 600 µM (100 IU/mL), 1200 µM (200 IU/mL), 1800 µM (300 IU/mL), 2400 µM (400 IU/mL) or 3000 µM (500 IU/mL).

In one embodiment, the polyanionic compound has affinity for zinc lower than the affinity of insulin for zinc and a dissociation constant $Kd_{Ca}=[PNP\ compound]^r\ [Ca^{2+}]^s/[(PNP\ compound)_r-(Ca^{2+})_s]$ is less than or equal to $10^{-1.5}$.

This dissociation constant is the reaction constant associated with the dissociation of the complex (PNP compound)$_r$–(Ca$^{2+}$)$_s$, i.e. with the following reaction: (PNP compound)$_r$–(Ca$^{2+}$)$_s$⇌r(PNP compound)+sCa$^{2+}$.

The dissociation constants (Kd) of the various polyanionic compounds with respect to calcium ions are determined by external calibration using an electrode specific for calcium ions (Mettler Toledo) and a reference electrode. All the measurements are performed in 150 mM of NaCl at pH 7. Only the concentrations of free calcium ions are determined; the calcium ions linked to the polyanionic compound do not induce an electrode potential.

In one embodiment, the polyanionic compound is chosen from the group consisting of the polycarboxylic acids and the Na$^+$, K$^+$, Ca$^{2+}$ or Mg$^{2+}$ salts thereof.

In one embodiment, the polyanionic compound is an anionic molecule.

In one embodiment, the anionic molecule is chosen from the group consisting of citric acid, aspartic acid, glutamic acid, malic acid, tartaric acid, succinic acid, adipic acid, oxalic acid, phosphate, polyphosphoric acids, such as triphosphate, and the Na$^+$, K$^+$, Ca$^{2+}$ or Mg$^{2+}$ salts thereof.

In one embodiment, the anionic molecule is citric acid and the Na$^+$, K$^+$, Ca$^{2+}$ or Mg$^{2+}$ salts thereof.

In one embodiment, the polyanionic compound is chosen from anionic compounds consisting of a saccharide backbone formed from a discrete number u between 1 and 8 (1≤u≤8) of saccharide units, said saccharide units being chosen from the group consisting of hexoses, in cyclic form or in reduced open form, which may be identical or different, linked via identical or different glycoside bonds substituted with carboxyl groups, and salts thereof.

In one embodiment, the polyanionic compound consisting of a saccharide backbone formed from a discrete number of saccharide units is obtained from a disaccharide compound chosen from the group consisting of trehalose, maltose, lactose, sucrose, cellobiose, isomaltose, maltitol and isomaltitol.

In one embodiment, the polyanionic compound consisting of a saccharide backbone formed from a discrete number of saccharide units is obtained from a compound consisting of a backbone formed from a discrete number of saccharide units chosen from the group consisting of maltotriose, maltotetraose, maltopentaose, maltohexaose, maltoheptaose, maltooctaose and isomaltotriose.

In one embodiment, the polyanionic compound consisting of a saccharide backbone formed from a discrete number of saccharide units is chosen from the group consisting of carboxymethylmaltotriose, carboxymethylmaltotetraose, carboxymethylmaltopentaose, carboxymethylmaltohexaose, carboxymethylmaltoheptaose, carboxymethylmaltooactose and carboxymethylisomaltotriose.

In one embodiment, the concentration of substituted anionic compound is between 1.8 and 100 mg/mL.

In one embodiment, the concentration of substituted anionic compound is between 1.8 and 50 mg/mL.

In one embodiment, the concentration of substituted anionic compound is between 1.8 and 36 mg/mL.

In one embodiment, the concentration of substituted anionic compound is between 1.8 and 36.5 mg/mL.

In one embodiment, the concentration of substituted anionic compound is between 2.1 and 25 mg/mL.

In one embodiment, the concentration of substituted anionic compound is between 4.2 and 18 mg/mL.

In one embodiment, the concentration of substituted anionic compound is between 5.6 and 15 mg/mL.

In one embodiment, the concentration of substituted anionic compound is between 7 and 15 mg/mL.

In one embodiment, the concentration of substituted anionic compound is 7.3 mg/mL.

In one embodiment, the concentration of substituted anionic compound is 10.5 mg/mL.

In one embodiment, the concentration of substituted anionic compound is 14.6 mg/mL.

In one embodiment, the concentration of substituted anionic compound is 21.9 mg/mL.

In one embodiment, the concentration of polyanionic compound is between 2 and 150 mM.

In one embodiment, the concentration of polyanionic compound is between 2 and 100 mM.

In one embodiment, the concentration of polyanionic compound is between 2 and 75 mM.

In one embodiment, the concentration of polyanionic compound is between 2 and 50 mM.

In one embodiment, the concentration of polyanionic compound is between 2 and 30 mM.

In one embodiment, the concentration of polyanionic compound is between 2 and 20 mM.

In one embodiment, the concentration of polyanionic compound is between 2 and 10 mM.

In one embodiment, the concentration of polyanionic compound is between 5 and 150 mM.

In one embodiment, the concentration of polyanionic compound is between 5 and 100 mM.

In one embodiment, the concentration of polyanionic compound is between 5 and 75 mM.

In one embodiment, the concentration of polyanionic compound is between 5 and 50 mM.

In one embodiment, the concentration of polyanionic compound is between 5 and 30 mM.

In one embodiment, the concentration of polyanionic compound is between 5 and 20 mM.

In one embodiment, the concentration of polyanionic compound is between 5 and 10 mM.

In one embodiment, the concentration of polyanionic compound is between 0.5 and 30 mg/mL.

In one embodiment, the concentration of polyanionic compound is between 0.5 and 25 mg/mL.

In one embodiment, the concentration of polyanionic compound is between 0.5 and 10 mg/mL.

In one embodiment, the concentration of polyanionic compound is between 0.5 and 8 mg/mL.

In one embodiment, the concentration of polyanionic compound is between 1 and 30 mg/mL.

In one embodiment, the concentration of polyanionic compound is between 1.5 and 25 mg/mL.

In one embodiment, the concentration of polyanionic compound is between 2 and 25 mg/mL.

In one embodiment, the concentration of polyanionic compound is between 2 and 10 mg/mL.

In one embodiment, the concentration of polyanionic compound is between 2 and 8 mg/mL.

In one embodiment, the pH of the composition is between 6 and 8.

In one particular embodiment, the composition according to the invention comprises insulin, especially as defined above, at least one substituted anionic compound as defined above, and citric acid or the $Na^+$, $K^+$, $Ca^{2+}$ or $Mg^{2+}$ salts thereof, especially as defined above.

In one particular embodiment, the composition according to the invention comprises insulin, especially as defined above, at least one substituted anionic compound corresponding to formula I as defined above, and citric acid or the $Na^+$, $K^+$, $Ca^{2+}$ or $Mg^{2+}$ salts thereof, especially as defined above.

In one particular embodiment, the composition according to the invention comprises insulin, especially as defined above, at least one substituted anionic compound corresponding to formula III as defined above, and citric acid or the $Na^+$, $K^+$, $Ca^{2+}$ or $Mg^{2+}$ salts thereof, especially as defined above.

In one particular embodiment, the composition according to the invention comprises insulin, especially as defined above, at least one substituted anionic compound corresponding to formula IV as defined above, and citric acid or the $Na^+$, $K^+$, $Ca^{2+}$ or $Mg^{2+}$ salts thereof, especially as defined above.

It is known to those skilled in the art that the delay of action of insulins is dependent on the insulin concentration. Only the delay of action values of the compositions at 100 IU/mL are documented.

The "regular" human insulin compositions on the market at a concentration of 600 μM (100 IU/mL) have a delay of action of between 50 and 90 minutes and an end of action of about 360 to 420 minutes in man. The time to reach the maximum insulin concentration in the blood is between 90 and 180 minutes in man.

The rapid insulin analog compositions on the market at a concentration of 600 μM (100 IU/mL) have a delay of action of between 30 and 60 minutes and an end of action of about 240-300 minutes in man. The time to reach the maximum insulin concentration in the blood is between 50 and 90 minutes in man.

The invention also relates to a method for preparing a human insulin composition with an insulin concentration of between 240 and 3000 μM (40 and 500 IU/mL), whose delay of action in man is less than that of the reference composition at the same insulin concentration in the absence of substituted anionic compound and of polyanionic compound, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention also relates to a method for preparing a human insulin composition with an insulin concentration of between 600 and 1200 μM (100 and 200 IU/mL), whose delay of action in man is less than that of the reference composition at the same insulin concentration in the absence of substituted anionic compound and of polyanionic compound, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention also relates to a method for preparing a human insulin composition with an insulin concentration of 600 μM (100 IU/mL), whose delay of action in man is less than 60 minutes, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention also relates to a method for preparing a human insulin composition with an insulin concentration of 1200 μM (200 IU/mL), whose delay of action in man is at least 10% less than that of the human insulin composition at the same concentration (200 IU/mL) and in the absence of substituted anionic compound and of polyanionic compound, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention also relates to a method for preparing a human insulin composition with an insulin concentration of 1800 μM (300 IU/mL), whose delay of action in man is at least 10% less than that of the human insulin composition at the same concentration (300 IU/mL) and in the absence of substituted anionic compound and of polyanionic compound, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention also relates to a method for preparing a human insulin composition with an insulin concentration of 2400 μM (400 IU/mL), whose delay of action in man is at least 10% less than that of the human insulin composition at the same concentration (400 IU/mL) and in the absence of substituted anionic compound and of polyanionic compound, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention also relates to a method for preparing a human insulin composition with an insulin concentration of 3000 μM (500 IU/mL), whose delay of action in man is at least 10% less than that of the human insulin composition at the same concentration (500 IU/mL) and in the absence of substituted anionic compound and of polyanionic compound, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention consists of the preparation of a "rapid" human insulin composition, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention also relates to a method for preparing a human insulin composition with an insulin concentration of 600 μM (100 IU/mL), whose delay of action in man is less than 60 minutes, preferably less than 45 minutes and more preferably less than 30 minutes, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention also relates to a method for preparing an insulin analog composition with an insulin concentration of between 240 and 3000 μM (40 and 500 IU/mL), whose delay of action in man is less than that of the reference composition at the same insulin concentration in the absence of substituted anionic compound and of polyanionic compound, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention also relates to a method for preparing an insulin analog composition with an insulin concentration of between 600 and 1200 μM (100 and 200 IU/mL), whose delay of action in man is less than that of the reference composition at the same insulin analog concentration in the absence of substituted anionic compound and of polyanionic compound, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention also relates to a method for preparing a human insulin composition with an insulin analog concentration of 600 μmol/L (100 IU/mL), whose delay of action in man is less than 30 minutes, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention also relates to a method for preparing a human insulin composition with an insulin analog concentration of 1200 μM (200 IU/mL), whose delay of action in man is at least 10% less than that of the insulin analog composition in the absence of substituted anionic compound and of polyanionic compound, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention also relates to a method for preparing a human insulin composition with an insulin analog concentration of 1800 μM (300 IU/mL), whose delay of action in man is at least 10% less than that of the insulin analog composition in the absence of substituted anionic compound and of polyanionic compound, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention also relates to a method for preparing a human insulin composition with an insulin analog concentration of 2400 μM (400 IU/mL), whose delay of action in man is at least 10% less than that of the insulin analog composition in the absence of substituted anionic compound and of polyanionic compound, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention also relates to a method for preparing a human insulin composition with an insulin analog concentration of 3000 μM (500 IU/mL), whose delay of action in man is at least 10% less than that of the insulin analog composition in the absence of substituted anionic compound and of polyanionic compound, characterized in that it comprises (1) a step of adding to said composition at least one substituted anionic compound, and (2) a step of adding to said composition at least one polyanionic compound.

In one embodiment, the insulin is in hexameric form.

In one embodiment, the pH of the composition is between 6 and 8.

The invention consists of the preparation of a "very rapid" insulin analog composition, characterized in that it comprises a step of adding to said composition at least one substituted anionic compound, said compound comprising partially substituted carboxyl functional groups, the unsubstituted carboxyl functional groups being salifiable.

In one embodiment, the preparation also comprises a step of adding to said composition at least one polyanionic compound.

In one embodiment, the insulin is in hexameric form.

In one embodiment, the pH of the composition is between 6 and 8.

In one embodiment, the invention relates to the use of at least one substituted anionic compound, in combination with a polyanionic compound, for preparing a human insulin pharmaceutical composition for, after administration, accelerating the passage of the human insulin into the blood and more rapidly reducing glycemia when compared with a composition free of substituted anionic compound.

In one embodiment, the invention relates to the use of at least one substituted anionic compound, in combination with a polyanionic compound, for preparing an insulin analog composition for, after administration, accelerating the passage of the insulin analogue into the blood and more rapidly reducing glycemia when compared with a composition free of substituted anionic compound.

In one embodiment, the pH of the composition is between 6 and 8.

The invention also relates to a pharmaceutical composition according to the invention, characterized in that it is obtained by drying and/or lyophilization.

In one embodiment, the compositions according to the invention also comprise the addition of zinc salts at a concentration of between 0 and 500 μM, especially between 0 and 300 μM and in particular between 0 and 200 μM.

In one embodiment, the compositions according to the invention comprise buffers at concentrations of between 0 and 100 mM, preferably between 0 and 50 mM or even between 15 and 50 mM.

In one embodiment, the buffer is Tris.

In one embodiment, the compositions according to the invention also comprise preserving agents.

In one embodiment, the preserving agents are chosen from the group consisting of m-cresol and phenol, alone or as a mixture.

In one embodiment, the concentration of preserving agents is between 10 and 50 mM and especially between 10 and 40 mM.

The compositions according to the invention may also comprise additives such as tonicity agents, for instance glycerol, sodium chloride (NaCl), mannitol and glycine.

The compositions according to the invention may also comprise additives in accordance with the pharmacopeas, for instance surfactants, for example polysorbate.

The compositions according to the invention may also comprise any excipient in accordance with the pharmacopeas and compatible with the insulins used at the working concentrations.

In the case of local and systemic releases, the envisaged modes of administration are the intravenous, subcutaneous, intradermal or intramuscular route. Most particularly, the mode of administration is the subcutaneous route.

The transdermal, oral, nasal, vaginal, ocular, buccal and hormonal administration routes are also envisaged.

The invention also relates to the use of a composition according to the invention for the composition of a human insulin or insulin analog solution with a concentration of 100 IU/mL or 200 IU/mL intended for implantable or transportable insulin pumps.

According to another of its aspects, the invention also relates to the substituted anionic compounds as defined above.

In one embodiment, the substituted anionic compound corresponds to formula I below:

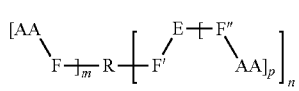
Formula I wherein
- R represents a saturated or unsaturated, linear, branched or cyclic hydrocarbon-based radical comprising from 1 to 12 carbon atoms, comprising at least one function chosen from ether and alcohol functions, and optionally comprising a carboxylic acid function,
- AA is a radical resulting from an aromatic amino acid comprising a phenyl group or an indole group, which is substituted or not substituted, or an aromatic amino acid derivative comprising a phenyl group or an indole group, which is substituted or not substituted, said radical AA bearing at least one free acid function,
- E represents an at least divalent linear or branched alkyl radical, comprising from 2 to 6 carbon atoms,
- F, F' and F" represent, independently of each other, a function chosen from amide, carbamate and urea functions, F and F" being functions resulting from a reaction involving the amine of the aromatic amino acid, a precursor of a radical AA, F' being a function involving a reactive function of the precursor of R and a reactive function of the precursor of E,
- p being an integer between 1 and 3,
- m is an integer between 0 and 6; n is an integer between 0 and 6; m+n is an integer between 1 and 6;

said compound comprising at least two carboxylic acid functions in the form of a salt of an alkali metal chosen from $Na^+$ and $K^+$,
with the exclusion of the compounds wherein m=2 and n=0 and R bearing a carboxylic acid function and an alcohol function In one embodiment, the at least 2 carboxylic acid functions in the form of a salt of an alkali metal are borne by the radicals R, AA or E.

In one embodiment, the at least 2 carboxylic acid functions in the form of a salt of an alkali metal are borne by the radicals R and E.

In one embodiment, the at least 2 carboxylic acid functions in the form of a salt of an alkali metal are borne by the radicals R and AA.

In one embodiment, the at least 2 carboxylic acid functions in the form of a salt of an alkali metal are borne by the radicals AA and E.

In one embodiment, the at least 2 carboxylic acid functions in the form of a salt of an alkali metal are borne by the radical R.

In one embodiment, the at least 2 carboxylic acid functions in the form of a salt of an alkali metal are borne by the radical AA.

In one embodiment, the at least 2 carboxylic acid functions in the form of a salt of an alkali metal are borne by the radical E.

In one embodiment, if m+n*p=1, then R comprises at least one carboxylic acid function. * represents the mathematical multiplication sign.

In one embodiment, F is chosen from amide and carbamate functions.
In one embodiment, F is an amide function.
In one embodiment, F is a carbamate function.
In one embodiment, F' is a urea function.
In one embodiment, F' is an amide function.
In one embodiment, F' is a carbamate function.
In one embodiment, F and F' are chosen from amide and carbamate functions.
In one embodiment, F and F' are amide functions.
In one embodiment, F and F' are carbamate functions.
In one embodiment, F" is a urea function.
In one embodiment, F" is an amide function.
In one embodiment, F" is a carbamate function.
In one embodiment, F' is an amide function and F" is a carbamate function.

In one embodiment, the radical R may comprise from 4 to 10 carbon atoms, in particular from 4 to 6 carbon atoms.

The radical R may be a linear, branched or cyclic hydrocarbon-based radical, and may be saturated or unsaturated. In particular, the radical R is a saturated linear hydrocarbon-based radical.

In one embodiment, m+n=6.
In one embodiment, m+n=5.
In one embodiment, m+n=4.
In one embodiment, m+n=3.
In one embodiment, m+n=2.
In one embodiment, m+n=1.

In one embodiment, the substituted anionic compound is chosen from the compounds of formula I wherein the radical —R— is chosen from radicals comprising 1 to 12 carbon atoms, of formula IV:

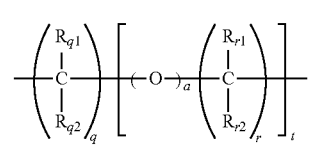
Formula IV wherein q and r are integers between 0 and 12, r is an integer between 0 and 3 and $1 \leq q+r*t \leq 12$, a is equal to 0 or 1, the groups $R_{q1}$, $R_{q2}$, $R_{r1}$ and $R_{r2}$ are, independently of each other, chosen from —H, —OH and —COOH. If a=0 then t=0 and at least one $R_{q1}$ or $R_{q2}$ is —OH. When $q \geq 1$ and/or $t \geq 1$, then the radicals $R_{q1}$ and $R_{q2}$ and the radicals $R_{r1}$ and $R_{r2}$ are identical or different from one carbon to another.

In one embodiment, the radical —R— is chosen from the radicals of formula IV wherein t=0, a=0 and r=0, represented by formula V:

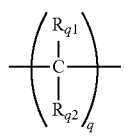
Formula V wherein q is an integer between 1 and 12 and the groups $R_{q1}$ and $R_{q2}$ are, independently of each other, chosen from —H, —OH and —COOH, and at least one $R_{q1}$ or $R_{q2}$ is —OH.

In one embodiment, the substituted anionic compound is chosen from the compounds of formula I wherein the radical —R— is a radical resulting from a compound comprising 1 to 12+(m+n) carbon atoms.

In one embodiment, the substituted anionic compound is chosen from the compounds of formula I wherein m+n=6 and the radical —R— is a radical resulting from a compound comprising 2 to 18 carbon atoms.

In one embodiment, the substituted anionic compound is chosen from the compounds of formula I wherein m+n=4 and the radical —R— is a radical resulting from a compound comprising 2 to 16 carbon atoms.

In one embodiment, the substituted anionic compound is chosen from the compounds of formula I wherein m+n=2 and the radical —R— is a radical resulting from a compound comprising 2 to 14 carbon atoms, of formula VI:

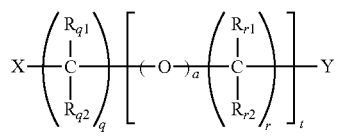

Formula VI wherein q and r are integers between 0 and 12 and 1≤q+r≤12, a is 0 or 1, the groups $R_{q1}$, $R_{q2}$, $R_{r1}$ and $R_{r2}$ are, independently of each other, chosen from —H, —OH and —COOH and —X and —Y, which may be identical or different, are chosen from —COOH, —OH and —NH$_2$. If a=0 then t=0 and at least one $R_{q1}$, $R_{q2}$, —X or —Y is —OH. When q≥1 and/or t≥1, then the radicals $R_{q1}$ and $R_{q2}$ and the radicals $R_{r1}$ and $R_{r2}$ are identical or different from one carbon to another.

—X and —Y are reactive functions that react with the precursor of E or of AA to form, respectively, F' or F.

In one embodiment, the substituted anionic compound is chosen from the compounds of formula I wherein m+n=1 and the radical —R— is a radical resulting from a compound comprising 2 to 13 carbon atoms, of formula VI above, and if —X or —Y is —NH$_2$, then it is the group that reacts with the precursor of E or of AA to form F' or F.

In one embodiment, the radical —R— is a radical resulting from a compound of formula VI wherein t=0, a=0 and r=0, represented by formula VII:

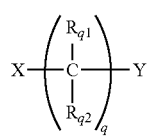

Formula VII wherein q is an integer between 1 and 12 and the groups $R_{q1}$ and $R_{q2}$ are, independently of each other, chosen from —H, —OH and —COOH, and —X and —Y, which may be identical or different, are chosen from —COOH, —OH and —NH$_2$ and at least one $R_{q1}$, $R_{q2}$, —X or —Y is —OH.

—X and —Y are reactive functions that react with the precursor of E or of AA to form, respectively, F' or F.

In one embodiment, the substituted anionic compound is chosen from the compounds of formula I wherein m+n=1 and the radical —R— is a radical resulting from a compound comprising 2 to 13 carbon atoms, of formula VI above, and if —X or —Y is —NH$_2$, then it is the group that reacts with the precursor of E or of AA to form F' or F.

In one embodiment, the precursor of R is chosen from the precursors of formula VI or VII wherein —X and —Y, which may be identical or different, are chosen from —COOH and —OH.

According to one embodiment, the radical R comprises o carboxylic acid functions, o being an integer between 1 and 3, o especially being equal to 1 or 2, and in particular o is equal to 1.

According to another embodiment, the radical R is free of carboxylic acid functions.

According to one embodiment, the radical R comprises 1 or 4 alcohol functions, especially 1 or 2 alcohol functions.

According to one embodiment, the radical R comprises 1 or 2 alcohol functions and 1 carboxylic acid function.

The radical R may originate from a polycarboxylic acid, especially from a dicarboxylic acid.

According to one embodiment, all the carboxylic acid functions of the polycarboxylic acid are involved in the functions F and F'.

Thus, according to this embodiment, all the carboxylic acid functions of the precursor of R are involved in the functions F and F'.

According to another embodiment, all the carboxylic acid functions of the polycarboxylic acid are not involved in the functions F and F'.

Thus, according to this embodiment, all the carboxylic acid functions of the precursor of R are not involved in the functions F and F'.

In particular, 1 or 2 carboxylic acid functions are not involved in the functions F and F', most particularly 1 carboxylic acid function is not involved in the functions F and F'.

In particular, the radical R is resulting from malic acid or tartaric acid.

In particular, the radical R is resulting from tartaric acid.

The radical R may be resulting from a diol. The diol may be chosen from ethylene glycol, diethylene glycol, triethylene glycol and tetraethylene glycol, propanediol, butanediol, pentanediol, hexanediol, heptanediol and octanediol.

In particular, the radical R of the substituted anionic compound is resulting from a dicarboxylic acid, an amino acid or a diol.

The radical AA is resulting from an aromatic amino acid comprising a phenyl or an indole, which is substituted or not substituted, or an aromatic amino acid derivative comprising a phenyl or an indole, which is substituted or not substituted. Most particularly, the radical AA is resulting from an aromatic amino acid comprising a phenyl or an indole, which is substituted or not substituted.

The radical AA is linked to the radical E or to the radical R via a function F or F'' involving the amine of the aromatic amino acid or of an aromatic amino acid derivative.

The term "aromatic amino acid comprising a substituted or not substituted phenyl or indole" means a compound comprising from 7 to 20 carbon atoms, a phenyl or an indole, which is substituted or not substituted, an amine function and an acid function.

The term "aromatic amino acid derivative" means decarboxylated derivatives, amino alcohol or amino amide derivatives corresponding to the aromatic amino acids comprising a phenyl or an indole, which is substituted or not substituted. The derivatives of said aromatic amino acid is comprising a phenyl or an indole, which is substituted or not substituted, may be chosen in particular from amino alcohols and amino amides.

According to one embodiment, AA is resulting from an aromatic amino acid comprising a phenyl or an indole, which is substituted or not substituted, chosen from alpha or beta amino acids. The aromatic amino acids comprising a phenyl or an indole, which is substituted or not substituted, may be chosen from the group consisting of phenylalanine, alpha-methylphenylalanine, 3,4-dihydroxyphenylalanine, alpha-phenylglycine, 4-hydroxyphenylglycine, 3,5-dihydroxyphenylglycine, tyrosine, alpha-methyltyrosine, O-methyltyrosine and tryptophan.

According to one embodiment, the aromatic amino acid comprising a phenyl or an indole, which is substituted or not substituted, is a natural amino acid, chosen especially from phenylalanine, tyrosine and tryptophan, most particularly phenylalanine.

The aromatic amino acids comprising a substituted or not substituted phenyl or indole, and the derivatives thereof may, where appropriate, be in levorotatory or dextrorotatory form or in racemic form. In particular, they are in levorotatory form.

According to one embodiment, the substituted anionic compound comprises from 1 to 6 radicals AA and in particular from 1 to 3 radicals AA.

In one embodiment, the radical E is resulting from a linear or branched alkyl compound comprising at least two functions chosen from the group consisting of —OH, —COOH and —NH$_2$.

In particular, the radical E is resulting from a compound comprising from 2 to 6 carbon atoms, and optionally comprising 1 or 2 carboxylic acid functions and/or 1, 2 or 3 alcohol functions.

The radical E is an at least divalent radical, in particular divalent, trivalent or tetravalent.

According to one embodiment, the radical E is resulting from a linear or branched alkyl compound, optionally bearing one or two carboxylic acid functions.

The radical E may be resulting from an amino alcohol, an amino diol or an amino triol, in particular chosen from the group consisting of trishydroxymethylaminomethane, also known as 2-amino-2-hydroxymethyl-1,3-propanediol or TRIS, serinol and threoninol.

According to one embodiment, when the radical E is resulting from an amino diol or an amino triol, it is, respectively, substituted with 2 or 3 radicals AA.

According to another embodiment, the radical E may be resulting from an amino acid comprising two carboxylic acid functions, in particular aspartic acid or glutamic acid. In this embodiment, the radical E may be linked to one or two radicals AA.

In one embodiment, the substituted anionic compound is chosen from the compounds of formula I wherein the precursor of the radical E does not comprise any —NH$_2$ functions.

In one embodiment, the substituted anionic compound is chosen from the compounds of formula I wherein the radical E is different from the radical R.

In one embodiment, the substituted anionic compound is chosen from the compounds of formula I wherein the precursor of the radical E is different from the precursor of the radical R.

According to one embodiment, the substituted anionic compound comprises from 2 to 8, especially from 2 to 6 or even from 2 to 4 carboxylic acid functions.

According to one embodiment, m+n*p=1.
According to one embodiment, m+n*p=2.
According to one embodiment, m+n*p=3.
According to one embodiment, m+n*p=4.
According to one embodiment, m+n*p=5.
According to one embodiment, m+n*p=6.
According to one embodiment, m+n*p=7.
According to one embodiment, m+n*p=8.

The calculation m+n*p gives the number of carboxylate functions provided by AA. When the radical R comprises free carboxylate functions, then the total number of free carboxylate functions is greater than m+n*p.

According to one embodiment, the substituted anionic compound does not comprise a radical AA linked via a spacer E. Thus, the substituted anionic compound may correspond to formula I wherein n=0.

According to one embodiment, the substituted anionic compound does not comprise a radical AA linked via a spacer E, and the substituted anionic compound may correspond to formula I wherein n=0 and corresponds to formula II:

Formula II

AA, F and R have the definitions given above,
$1 \leq m \leq 6$.

In one embodiment, the substituted anionic compound is chosen from the anionic compounds of formula II wherein m=1:

Formula VIII

In one embodiment, the substituted anionic compound is chosen from the anionic compounds of formula II wherein m=2:

Formula (IX)

According to one embodiment, the substituted anionic compound does not comprise a radical AA linked via the function F to the radical R. Thus, the substituted anionic compound may correspond to formula I wherein m=0.

According to one embodiment, the substituted anionic compound does not comprise a radical AA linked via the function F to the radical R, and the substituted anionic compound may correspond to formula I wherein m=0 and corresponds to formula III:

Formula III

AA, E, F', F'', p and R have the definitions given above,
$1 \leq n \leq 6$.

In one embodiment, the substituted anionic compound is chosen from the anionic compounds of formula III wherein n=1:

Formula X

In one embodiment, the substituted anionic compound is chosen from the anionic compounds of formula III wherein n=2:

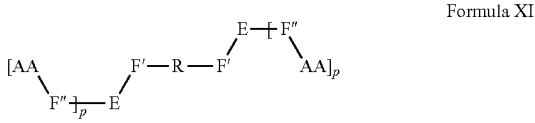

Formula XI

In one embodiment, the substituted anionic compound is chosen from the anionic compounds of formula III, X or XI wherein p=1.

In one embodiment, the substituted anionic compound is chosen from the anionic compounds of formula III, X or XI wherein p=2.

In one embodiment, the substituted anionic compound is chosen from the anionic compounds of formula III, X or XI wherein p=3.

In one embodiment, the substituted anionic compound is chosen from the anionic compounds of formula III or X wherein n=1 and p=3.

In one embodiment, the substituted anionic compound is chosen from the anionic compounds of formula III wherein n=2 and p=3.

In one embodiment, the substituted anionic compound corresponds to formula I below:

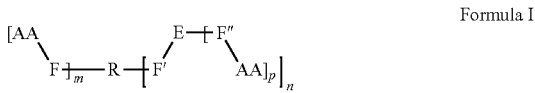

Formula I wherein
R represents a saturated or unsaturated, linear, branched or cyclic hydrocarbon-based radical comprising from 6 to 12 carbon atoms, optionally comprising at least one function chosen from ether, alcohol and carboxylic acid functions.
F, F' and F" represent, independently of each other, a function chosen from amide, carbamate and urea functions, F and F" being functions resulting from a reaction involving the amine of the aromatic amino acid, a precursor of a radical AA, F' being a function involving a reactive function of the precursor of R and a reactive function of the precursor of E,
AA is a radical resulting from an aromatic amino acid comprising a phenyl group or an indole group, which is substituted or not substituted, or an aromatic amino acid derivative comprising a phenyl group or an indole group, which is substituted or not substituted, said radical AA bearing at least one free acid function,
E represents an at least divalent linear or branched alkyl radical, comprising from 2 to 6 carbon atoms,
p being an integer between 1 and 3,
m is an integer between 0 and 6; n is an integer between 0 and 6; m+n is an integer between 1 and 6;
said compound comprising at least two carboxylic acid functions in the form of a salt of an alkali metal chosen from $Na^+$ and $K^+$.
In one embodiment, if m+n*p=1, then R comprises at least one carboxylic acid function. * represents the mathematical multiplication sign.

In one embodiment, the at least 2 carboxylic acid functions in the form of a salt of an alkali metal are borne by the radicals R, AA or E.

In one embodiment, the at least 2 carboxylic acid functions in the form of a salt of an alkali metal are borne by the radicals R and E.

In one embodiment, the at least 2 carboxylic acid functions in the form of a salt of an alkali metal are borne by the radicals R and AA.

In one embodiment, the at least 2 carboxylic acid functions in the form of a salt of an alkali metal are borne by the radicals AA and E.

In one embodiment, the at least 2 carboxylic acid functions in the form of a salt of an alkali metal are borne by the radical R.

In one embodiment, the at least 2 carboxylic acid functions in the form of a salt of an alkali metal are borne by the radical AA.

In one embodiment, the at least 2 carboxylic acid functions in the form of a salt of an alkali metal are borne by the radical E.

In one embodiment, F is chosen from amide and carbamate functions.
In one embodiment, F is an amide function.
In one embodiment, F is a carbamate function.
In one embodiment, F' is a urea function.
In one embodiment, F' is an amide function.
In one embodiment, F' is a carbamate function.
In one embodiment, F and F' are chosen from amide and carbamate functions.
In one embodiment, F and F' are amide functions.
In one embodiment, F and F' are carbamate functions.
In one embodiment, F" is a urea function.
In one embodiment, F" is an amide function.
In one embodiment, F" is a carbamate function.
In one embodiment, F' is an amide function and F" is a carbamate function.

The radical R may be a linear, branched or cyclic hydrocarbon-based radical, and may be saturated or unsaturated. In particular, the radical R is a saturated linear hydrocarbon-based radical.

In one embodiment, m+n=6.
In one embodiment, m+n=5.
In one embodiment, m+n=4.
In one embodiment, m+n=3.
In one embodiment, m+n=2.
In one embodiment, m+n=1.

In one embodiment, the substituted anionic compound is chosen from the compounds of formula I wherein the radical —R— is chosen from radicals comprising 6 to 12 carbon atoms, of formula IV:

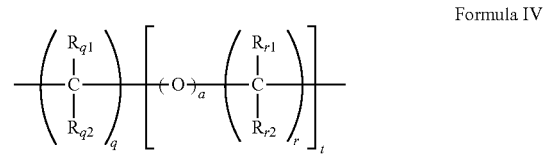

Formula IV wherein q and r are integers between 0 and 12, r is an integer between 0 and 3 and 2≤q+r*t≤12, a is equal to 0 or 1, the groups $R_{q1}$, $R_{q2}$, $R_{r1}$ and $R_{r2}$ are, independently of each other, chosen from —H, —OH and —COOH. If a=0 then t=0. When q≥1 and/or t≥1, then the radicals $R_{q1}$ and $R_{q2}$ and the radicals $R_{r1}$ and $R_{r2}$ are identical or different from one carbon to another.

In one embodiment, the radical —R— is chosen from the radicals of formula IV wherein t=0, a=0 and r=0, represented by formula V:

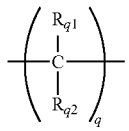

Formula V wherein q is an integer between 2 and 12 and the groups $R_{q1}$ and $R_{q2}$ are, independently of each other, chosen from —H, —OH and —COOH.

In one embodiment, when the substituents are linked via a function resulting from an acid function of the precursor of R, the substituted anionic compound is chosen from the compounds of formula I wherein the radical —R— is a radical resulting from a compound comprising 6 to 12+(m+n) carbon atoms.

In one embodiment, the substituted anionic compound is chosen from the compounds of formula I wherein m+n=6 and the radical —R— is a radical resulting from a compound comprising 6 to 18 carbon atoms.

In one embodiment, the substituted anionic compound is chosen from the compounds of formula I wherein m+n=4 and the radical —R— is a radical resulting from a compound comprising 6 to 16 carbon atoms.

In one embodiment, the substituted anionic compound is chosen from the compounds of formula I wherein m+n=2 and the radical —R— is a radical resulting from a compound comprising 6 to 14 carbon atoms, of formula VI:

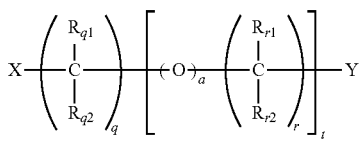

Formula VI wherein q and r are integers between 0 and 12 and 2≤q+r≤12, a is 0 or 1, the groups $R_{q1}$, $R_{q2}$, $R_{r1}$ and $R_{r2}$ are, independently of each other, chosen from —H, —OH and —COOH and —X and —Y, which may be identical or different, are chosen from —COOH, —OH and —NH$_2$. If a=0 then t=0. When q 1 and/or t≥1, then the radicals $R_{q1}$ and $R_{q2}$ and the radicals $R_{r1}$ and $R_{r2}$ are identical or different from one carbon to another.

—X and —Y are reactive functions that react with the precursor of E or of AA to form, respectively, F' or F.

In one embodiment, the substituted anionic compound is chosen from the compounds of formula I wherein m+n=1 and the radical —R— is a radical resulting from a compound comprising 6 to 13 carbon atoms, of formula VI above, and if —X or —Y is —NH$_2$, then it is the group that reacts with the precursor of E or of AA to form F' or F.

In one embodiment, the radical —R— is a radical resulting from a compound of formula VI wherein t=0, a=0 and r=0, represented by formula VII:

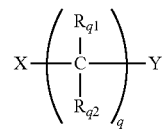

Formula VII wherein q is an integer between 2 and 12 and the groups $R_{q1}$ and $R_{42}$ are, independently of each other, chosen from —H, —OH and —COOH, and —X and —Y, which may be identical or different, are chosen from —COOH, —OH and —NH$_2$.

—X and —Y are reactive functions that react with the precursor of E or of AA to form, respectively, F' or F.

In one embodiment, the substituted anionic compound is chosen from the compounds of formula I wherein m+n=1 and the radical —R— is a radical resulting from a compound comprising 6 to 13 carbon atoms, of formula VI above, and if —X or —Y is —NH$_2$, then it is the group that reacts with the precursor of E or of AA to form F' or F.

In one embodiment, the precursor of R is chosen from the precursors of formula VI or VII wherein —X and —Y, which may be identical or different, are chosen from —COOH and —OH.

The radical R may comprise at least one function chosen in particular from alcohol and carboxylic acid functions.

According to one embodiment, the radical R comprises o carboxylic acid functions, o being an integer between 1 and 3, o especially being equal to 1 or 2, and in particular o is equal to 1.

According to another embodiment, the radical R is free of carboxylic acid functions.

According to one embodiment, the radical R comprises at least one alcohol function, and in particular comprises from 1 to 4 alcohol functions, especially 1 or 2 alcohol functions.

According to another embodiment, the radical R is free of alcohol functions.

According to one embodiment, the radical R comprises 1 or 2 alcohol functions and 1 carboxylic acid function.

The radical R may originate from a polycarboxylic acid, especially from a dicarboxylic acid.

According to one embodiment, all the carboxylic acid functions of the polycarboxylic acid are involved in the functions F and F'.

Thus, according to this embodiment, all the carboxylic acid functions of the precursor of R are involved in the functions F and F'.

According to another embodiment, all the acid functions of the polycarboxylic acid are not involved in the functions F and F'.

Thus, according to this embodiment, all the carboxylic acid functions of the precursor of R are not involved in the functions F and F'.

In particular, 1 or 2 carboxylic acid functions are not involved in the functions F and F', most particularly 1 carboxylic acid function is not involved in the functions F and F'.

The radical R may be resulting from a dicarboxylic acid chosen from heptanedioic acid, octanedioic acid and nonanedioic acid.

The radical R may be resulting from a diol. The diol may be chosen from triethylene glycol and tetraethylene glycol, hexanediol, heptanediol and octanediol.

In particular, the radical R of the substituted anionic compound is resulting from a dicarboxylic acid, an amino acid or a diol.

The radical AA is resulting from an aromatic amino acid comprising a phenyl or an indole, which is substituted or not substituted, or an aromatic amino acid derivative comprising a phenyl or an indole, which is substituted or not substituted. Most particularly, the radical AA is resulting from an aromatic amino acid comprising a phenyl or an indole, which is substituted or not substituted.

The radical AA is linked to the radical E or to the radical R via a function F or F" involving the amine of the aromatic amino acid or of an aromatic amino acid derivative.

The term "aromatic amino acid comprising a substituted or not substituted phenyl or indole" means a compound comprising from 7 to 20 carbon atoms, a phenyl or an indole, which is substituted or not substituted, an amine function and an acid function.

The term "aromatic amino acid derivative" means decarboxylated derivatives, amino alcohol or amino amide derivatives corresponding to the aromatic amino acids comprising a phenyl or an indole, which is substituted or not substituted. The derivatives of said aromatic amino acid is comprising a phenyl or an indole, which is substituted or not substituted, may be chosen in particular from amino alcohols and amino amides.

According to one embodiment, AA is resulting from an aromatic amino acid comprising a phenyl or an indole, which is substituted or not substituted, chosen from alpha or beta amino acids. The aromatic amino acids comprising a phenyl or an indole, which is substituted or not substituted, may be chosen from the group consisting of phenylalanine, alpha-methylphenylalanine, 3,4-dihydroxyphenylalanine, alpha-phenylglycine, 4-hydroxyphenylglycine, 3,5-dihydroxyphenylglycine, tyrosine, alpha-methyltyrosine, O-methyltyrosine and tryptophan.

According to one embodiment, the aromatic amino acid comprising a phenyl or an indole, which is substituted or not substituted, is a natural amino acid, chosen especially from phenylalanine, tyrosine and tryptophan, most particularly phenylalanine.

The aromatic amino acids comprising a substituted or not substituted phenyl or indole, and the derivatives thereof may, where appropriate, be in levorotatory or dextrorotatory form or in racemic form. In particular, they are in levorotatory form.

According to one embodiment, the substituted anionic compound comprises from 1 to 6 radicals AA and in particular from 1 to 3 radicals AA.

In one embodiment, the radical E is resulting from a linear or branched alkyl compound comprising at least two functions chosen from the group consisting of —OH, —COOH and —NH$_2$.

In particular, the radical E is resulting from a compound comprising from 2 to 6 carbon atoms, and optionally comprising 1 or 2 carboxylic acid functions and/or 1, 2 or 3 alcohol functions.

The radical E is an at least divalent radical, in particular divalent, trivalent or tetravalent.

According to one embodiment, the radical E is resulting from a linear or branched alkyl compound, optionally bearing one or two carboxylic acid functions.

The radical E may be resulting from an amino alcohol, an amino diol or an amino triol, in particular chosen from the group consisting of trishydroxymethylaminomethane, also known as 2-amino-2-hydroxymethyl-1,3-propanediol or TRIS, serinol and threoninol.

According to one embodiment, when the radical E is resulting from an amino diol or an amino triol, it is, respectively, substituted with 2 or 3 radicals AA.

According to another embodiment, the radical E may be resulting from an amino acid comprising two carboxylic acid functions, in particular aspartic acid or glutamic acid. In this embodiment, the radical E may be linked to one or two radicals AA.

In one embodiment, the substituted anionic compound is chosen from the compounds of formula I wherein the precursor of the radical E does not comprise any —NH$_2$ functions.

In one embodiment, the substituted anionic compound is chosen from the compounds of formula I wherein the radical E is different from the radical R.

In one embodiment, the substituted anionic compound is chosen from the compounds of formula I wherein the precursor of the radical E is different from the precursor of the radical R.

According to one embodiment, the substituted anionic compound comprises from 2 to 8, especially from 2 to 6 or even from 2 to 4 carboxylic acid functions.

According to one embodiment, $m+n*p=1$.

According to one embodiment, $m+n*p=2$.

According to one embodiment, $m+n*p=3$.

According to one embodiment, $m+n*p=4$.

According to one embodiment, $m+n*p=5$.

According to one embodiment, $m+n*p=6$.

According to one embodiment, $m+n*p=7$.

According to one embodiment, $m+n*p=8$.

The calculation $m+n*p$ gives the number of carboxylate functions provided by AA. When the radical R comprises free carboxylate functions, then the total number of free carboxylate functions is greater than $m+n*p$.

According to one embodiment, the substituted anionic compound does not comprise a radical AA linked via a spacer E. Thus, the substituted anionic compound may correspond to formula I wherein $n=0$.

According to one embodiment, the substituted anionic compound does not comprise a radical AA linked via a spacer E, and the substituted anionic compound may correspond to formula I wherein $n=0$ and corresponds to formula II:

Formula II

AA, F and R have the definitions given above, $1 \leq m \leq 6$.

In one embodiment, the substituted anionic compound is chosen from the anionic compounds of formula II wherein $m=1$:

Formula VIII

In one embodiment, the substituted anionic compound is chosen from the anionic compounds of formula II wherein $m=2$:

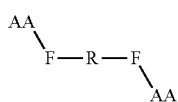

Formula (IX)

According to one embodiment, the substituted anionic compound does not comprise a radical AA linked via the function F to the radical R. Thus, the substituted anionic compound may correspond to formula I wherein m=0.

According to one embodiment, the substituted anionic compound does not comprise a radical AA linked via the function F to the radical R, and the substituted anionic compound may correspond to formula I wherein m=0 and corresponds to formula III:

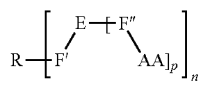

Formula III

AA, E, F', F", p and R have the definitions given above, $1 \leq n \leq 6$.

In one embodiment, the substituted anionic compound is chosen from the anionic compounds of formula III wherein n=1:

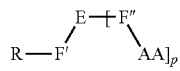

Formula X

In one embodiment, the substituted anionic compound is chosen from the anionic compounds of formula III wherein n=2:

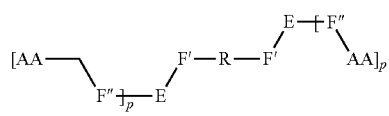

Formula XI

In one embodiment, the substituted anionic compound is chosen from the anionic compounds of formula III, X or XI wherein p=1.

In one embodiment, the substituted anionic compound is chosen from the anionic compounds of formula III, X or XI wherein p=2.

In one embodiment, the substituted anionic compound is chosen from the anionic compounds of formula III, X or XI wherein p=3.

In one embodiment, the substituted anionic compound is chosen from the anionic compounds of formula III or X wherein n=1 and p=3.

In one embodiment, the substituted anionic compound is chosen from the anionic compounds of formula III wherein n=2 and p=3.

In one embodiment, the substituted anionic compound corresponds to formula I below:

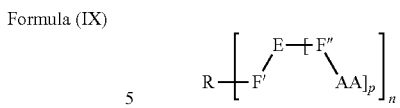

Formula XII wherein
R represents a saturated or unsaturated, linear, branched or cyclic hydrocarbon-based radical comprising from 1 to 12 carbon atoms, optionally comprising at least one function chosen from ether, alcohol and carboxylic acid functions.

F' and F" represent, independently of each other, a function chosen from amide, carbamate and urea functions, F" being a function resulting from a reaction involving the amine of the aromatic amino acid, a precursor of the radical AA, F' being a function involving a reactive function of the precursor of R and a reactive function of the precursor of E, AA is a radical resulting from an aromatic amino acid comprising a phenyl group or an indole group, which is substituted or not substituted, or an aromatic amino acid derivative comprising a phenyl group or an indole group, which is substituted or not substituted, said radical AA bearing at least one free acid function, E represents an at least divalent linear or branched alkyl radical, comprising from 2 to 6 carbon atoms, p being an integer between 1 and 3, n represents an integer between 1 and 6;

said compound comprising at least two carboxylic acid functions in the form of a salt of an alkali metal chosen from $Na^+$ and $K^+$.

In one embodiment, the at least 2 carboxylic acid functions in the form of a salt of an alkali metal are borne by the radicals R, AA or E.

In one embodiment, the at least 2 carboxylic acid functions in the form of a salt of an alkali metal are borne by the radicals R and E.

In one embodiment, the at least 2 carboxylic acid functions in the form of a salt of an alkali metal are borne by the radicals R and AA.

In one embodiment, the at least 2 carboxylic acid functions in the form of a salt of an alkali metal are borne by the radicals AA and E.

In one embodiment, the at least 2 carboxylic acid functions in the form of a salt of an alkali metal are borne by the radical R.

In one embodiment, the at least 2 carboxylic acid functions in the form of a salt of an alkali metal are borne by the radical AA.

In one embodiment, the at least 2 carboxylic acid functions in the form of a salt of an alkali metal are borne by the radical E.

In one embodiment, if n*p=1, then R comprises at least one carboxylic acid function. * represents the mathematical multiplication sign.

In one embodiment, F' is a urea function.
In one embodiment, F' is an amide function.
In one embodiment, F' is a carbamate function.
In one embodiment, F" is a urea function.
In one embodiment, F" is an amide function.
In one embodiment, F" is a carbamate function.
In one embodiment, F' is an amide function and F" is a carbamate function.

In one embodiment, the radical R may comprise from 4 to 10 carbon atoms, in particular from 4 to 6 carbon atoms.

The radical R may be a linear, branched or cyclic hydrocarbon-based radical, and may be saturated or unsaturated. In particular, the radical R is a saturated linear hydrocarbon-based radical.

In one embodiment, n=6.

In one embodiment, n=5.

In one embodiment, n=4.

In one embodiment, n=3.

In one embodiment, n=2.

In one embodiment, n=1.

In one embodiment, the substituted anionic compound is chosen from the compounds of formula I wherein the radical —R— is chosen from radicals comprising 1 to 12 carbon atoms, of formula IV:

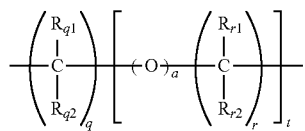

Formula IV wherein q and r are integers between 0 and 12, r is an integer between 0 and 3 and 1≤q+r*t≤12, a is equal to 0 or 1, the groups $R_{q1}$, $R_{q2}$, $R_{r1}$ and $R_{r2}$ are, independently of each other, chosen from —H, —OH and —COOH. If a=0 then t=0. When q≥1 and/or t≥1, then the radicals $R_{q1}$ and $R_{q2}$ and the radicals $R_{r1}$ and $R_{r2}$ are identical or different from one carbon to another.

In one embodiment, the radical —R— is chosen from the radicals of formula IV wherein t=0, a=0 and r=0, represented by formula V:

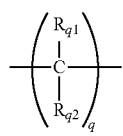

Formula V wherein q is an integer between 1 and 12 and the groups $R_{q1}$ and $R_{q2}$ are, independently of each other, chosen from —H, —OH and —COOH.

In one embodiment, the substituted anionic compound is chosen from the compounds of formula I wherein the radical —R— is a radical resulting from a compound comprising 1 to 12+n carbon atoms.

In one embodiment, the substituted anionic compound is chosen from the compounds of formula I wherein n=6 and the radical —R— is a radical resulting from a compound comprising 2 to 18 carbon atoms.

In one embodiment, the substituted anionic compound is chosen from the compounds of formula I wherein n=4 and the radical —R— is a radical resulting from a compound comprising 2 to 16 carbon atoms.

In one embodiment, the substituted anionic compound is chosen from the compounds of formula I wherein n=2 and the radical —R— is a radical resulting from a compound comprising 2 to 14 carbon atoms, of formula VI:

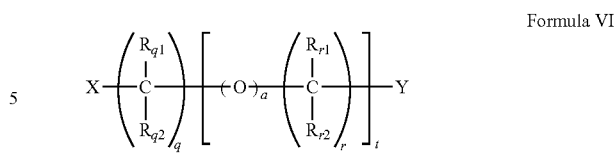

Formula VI wherein q and r are integers between 0 and 12 and 1≤q+r≤12, a is 0 or 1, the groups $R_{q1}$, $R_{q2}$, $R_{r1}$ and $R_{r2}$ are, independently of each other, chosen from —H, —OH and —COOH and —X and —Y, which may be identical or different, are chosen from —COOH, —OH and —NH₂. If a=0 then t=0. When q≥1 and/or t≥1, then the radicals $R_{q1}$ and $R_{q2}$ and the radicals $R_{r1}$ and $R_{r2}$ are identical or different from one carbon to another.

—X and —Y are reactive functions that react with the precursor of E to form F.

In one embodiment, the substituted anionic compound is chosen from the compounds of formula I wherein n=1 and the radical —R— is a radical resulting from a compound comprising 1 to 13 carbon atoms, of formula VI above, and if an —X or —Y is —NH₂, then it is the group that will react with the precursor of E to form F' or F.

In one embodiment, the radical —R— is a radical resulting from a compound of formula VI wherein t=0, a=0 and r=0, represented by formula VII:

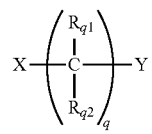

Formula VII wherein q is an integer between 1 and 12 and the groups $R_{q1}$ and $R_{q2}$ are, independently of each other, chosen from —H, —OH and —COOH, and —X and —Y, which may be identical or different, are chosen from —COOH, —OH and —NH₂.

—X and —Y are reactive functions that react with the precursor of E to form F'.

In one embodiment, the substituted anionic compound is chosen from the compounds of formula I wherein n=1 and the radical —R— is a radical resulting from a compound comprising 2 to 13 carbon atoms, of formula VI above, and if —X or —Y is —NH₂, then it is the group that reacts with the precursor of E to form F.

In one embodiment, the precursor of R is chosen from the precursors of formula VI or VII wherein —X and —Y, which may be identical or different, are chosen from —COOH and —OH.

The radical R may comprise at least one function chosen in particular from alcohol and carboxylic acid functions.

According to one embodiment, the radical R comprises o carboxylic acid functions, o being an integer between 1 and 3, o especially being equal to 1 or 2, and in particular o is equal to 1.

According to another embodiment, the radical R is free of carboxylic acid functions.

According to one embodiment, the radical R comprises at least one alcohol function, and in particular comprises from 1 to 4 alcohol functions, especially 1 or 2 alcohol functions.

According to another embodiment, the radical R is free of alcohol functions.

According to one embodiment, the radical R comprises 1 or 2 alcohol functions and 1 carboxylic acid function.

The radical R may originate from a polycarboxylic acid, especially from a dicarboxylic acid.

According to one embodiment, all the carboxylic acid functions of the polycarboxylic acid are involved in the functions F'.

Thus, according to this embodiment, all the carboxylic acid functions of the precursor of R are involved in the functions F'.

According to another embodiment, all the acid functions of the polycarboxylic acid are not involved in the functions F'.

Thus, according to this embodiment, all the carboxylic acid functions of the precursor of R are not involved in the functions F'.

In particular, 1 or 2 carboxylic acid functions are not involved in the functions F', most particularly 1 carboxylic acid function is not involved in the functions F'.

The radical R may be resulting from a dicarboxylic acid chosen from propanedioic acid, butanedioic acid (or succinic acid), tartaric acid, malic acid, pentanedioic acid, hexanedioic acid (or adipic acid), heptanedioic acid, octanedioic acid, nonanedioic acid, pentanedioic acid, butenedioic acid, pentenedioic acid and hexadienedioic acid (or adipic acid).

In particular, the radical R is resulting from a dicarboxylic acid chosen from butanedioic acid (or succinic acid), tartaric acid, malic acid, pentanedioic acid and hexanedioic acid (or adipic acid).

Even more particularly, the radical R is resulting from a dicarboxylic acid chosen from butanedioic acid (or succinic acid) and tartaric acid.

The radical R may be resulting from an amino acid.

In particular, the radical R may be resulting from an amino acid chosen from glutamic acid and aspartic acid.

The radical R may be resulting from a diol. The diol may be chosen from ethylene glycol, diethylene glycol, triethylene glycol and tetraethylene glycol, propanediol, butanediol, pentanediol, hexanediol, heptanediol and octanediol.

In particular, the radical R of the substituted anionic compound is resulting from a dicarboxylic acid, an amino acid or a diol.

The radical AA is resulting from an aromatic amino acid comprising a phenyl or an indole, which is substituted or not substituted, or an aromatic amino acid derivative comprising a phenyl or an indole, which is substituted or not substituted. Most particularly, the radical AA is resulting from an aromatic amino acid comprising a phenyl or an indole, which is substituted or not substituted.

The radical AA is linked to the radical E via a function F''' involving the amine of the aromatic amino acid or of an aromatic amino acid derivative.

The term "aromatic amino acid comprising a substituted or not substituted phenyl or indole" means a compound comprising from 7 to 20 carbon atoms, a phenyl or an indole, which is substituted or not substituted, an amine function and an acid function.

The term "aromatic amino acid derivative" means decarboxylated derivatives, amino alcohol or amino amide derivatives corresponding to the aromatic amino acids comprising a phenyl or an indole, which is substituted or not substituted. The derivatives of said aromatic amino acids comprising a phenyl or an indole, which is substituted or not substituted, may be chosen in particular from amino alcohols and amino amides.

According to one embodiment, AA is resulting from an aromatic amino acid comprising a phenyl or an indole, which is substituted or not substituted, chosen from alpha or beta amino acids. The aromatic amino acids comprising a phenyl or an indole, which is substituted or not substituted, may be chosen from the group consisting of phenylalanine, alpha-methylphenylalanine, 3,4-dihydroxyphenylalanine, alpha-phenylglycine, 4-hydroxyphenylglycine, 3,5-dihydroxyphenylglycine, tyrosine, alpha-methyltyrosine, O-methyltyrosine and tryptophan.

According to one embodiment, the aromatic amino acid comprising a phenyl or an indole, which is substituted or not substituted, is a natural amino acid, chosen especially from phenylalanine, tyrosine and tryptophan, most particularly phenylalanine.

The aromatic amino acids comprising a substituted or not substituted phenyl or indole, and the derivatives thereof may, where appropriate, be in levorotatory or dextrorotatory form or in racemic form. In particular, they are in levorotatory form.

According to one embodiment, the substituted anionic compound comprises from 1 to 6 radicals AA and in particular from 1 to 3 radicals AA.

In one embodiment, the radical E is resulting from a linear or branched alkyl compound comprising at least two functions chosen from the group consisting of —OH, —COOH and —NH$_2$.

In particular, the radical E is resulting from a compound comprising from 2 to 6 carbon atoms, and optionally comprising 1 or 2 carboxylic acid functions and/or 1, 2 or 3 alcohol functions.

The radical E is an at least divalent radical, in particular divalent, trivalent or tetravalent.

According to one embodiment, the radical E is resulting from a linear or branched alkyl compound, optionally bearing one or two carboxylic acid functions.

The radical E may be resulting from an amino alcohol, an amino diol or an amino triol, in particular chosen from the group consisting of trishydroxymethylaminomethane, also known as 2-amino-2-hydroxymethyl-1,3-propanediol or TRIS, serinol and threoninol.

According to one embodiment, when the radical E is resulting from an amino diol or an amino triol, it is, respectively, substituted with 2 or 3 radicals AA.

According to another embodiment, the radical E may be resulting from an amino acid comprising two carboxylic acid functions, in particular aspartic acid or glutamic acid. In this embodiment, the radical E may be linked to one or two radicals AA.

In one embodiment, the substituted anionic compound is chosen from the compounds of formula I wherein the precursor of the radical E does not comprise any —NH$_2$ functions.

In one embodiment, the substituted anionic compound is chosen from the compounds of formula I wherein the radical E is different from the radical R.

In one embodiment, the substituted anionic compound is chosen from the compounds of formula I wherein the precursor of the radical E is different from the precursor of the radical R.

According to one embodiment, the substituted anionic compound comprises from 2 to 8, especially from 2 to 6 or even from 2 to 4 carboxylic acid functions.

In one embodiment, n*p=1.
In one embodiment, n*p=2.
In one embodiment, n*p=3.
In one embodiment, n*p=4.

In one embodiment, n*p=5.
In one embodiment, n*p=6.
In one embodiment, n*p=7.
In one embodiment, n*p=8.

The calculation n*p gives the number of carboxylate functions provided by AA. When the radical R comprises free carboxylate functions, then the total number of free carboxylate functions is greater than n*p.

In one embodiment, the substituted anionic compound is chosen from the anionic compounds of formula XII wherein n=1:

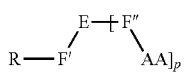

Formula X

In one embodiment, the substituted anionic compound is chosen from the anionic compounds of formula XII wherein n=2:

Formula XI $$[AA\diagdown_{F''\!\!\!-\!\!\!\mid_p\!\!\!-\!\!E}F'\!-\!R\!-\!F'\diagup^{E\!-\!\!\mid\!\!F''}_{\diagdown AA]_p}$$

In one embodiment, the substituted anionic compound is chosen from the anionic compounds of formula XII, X or XI wherein p=1.

In one embodiment, the substituted anionic compound is chosen from the anionic compounds of formula XII, X or XI wherein p=2.

In one embodiment, the substituted anionic compound is chosen from the anionic compounds of formula XII, X or XI wherein p=3.

In one embodiment, the substituted anionic compound is chosen from the anionic compounds of formula XII or X wherein n=1 and p=3.

In one embodiment, the substituted anionic compound is chosen from the anionic compounds of formula XII or XI wherein n=2 and p=3.

EXAMPLES

Figure 1:
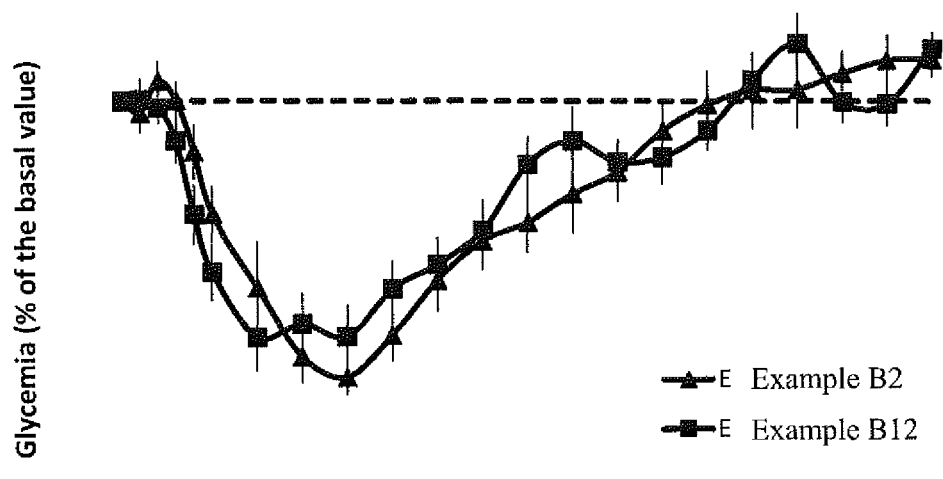
FIG. 1 describes the pharmacodynamic results obtained with the compositions described in examples B2 and B12.

TABLE 1 below presents, in a nonlimiting manner, examples of compounds according to the invention.

| Substituted anionic compounds | Formulations |
|---|---|
| A1 | 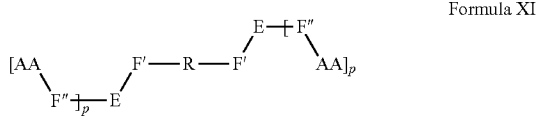 |

TABLE 1-continued
below presents, in a nonlimiting manner, examples of compounds according to the invention.
| Substituted anionic compounds | Formulations |
|---|---|
| A2 | 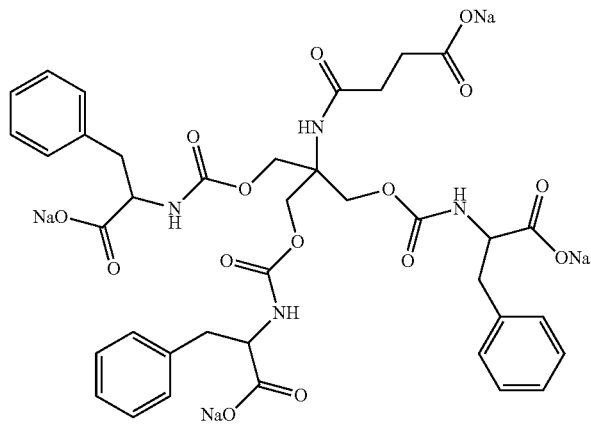 |
| A3 | 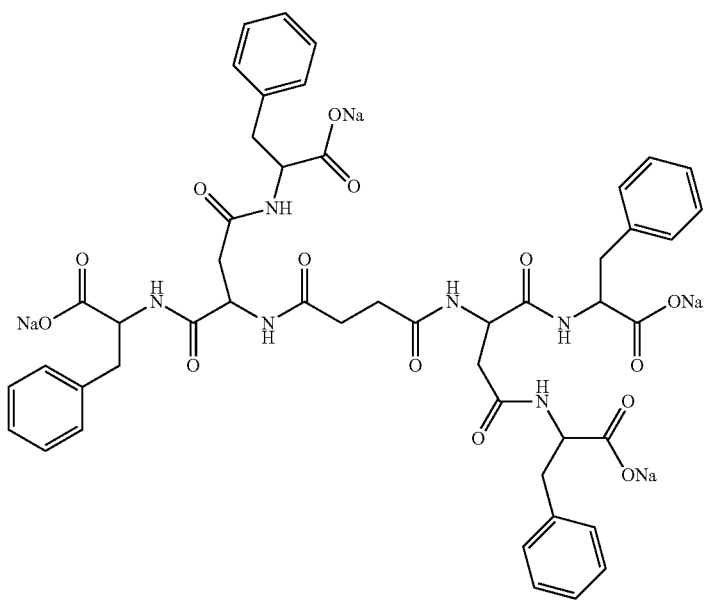 |

TABLE 1-continued
below presents, in a nonlimiting manner, examples of compounds according to the invention.
| Substituted anionic compounds | Formulations |
|---|---|
| A4 | 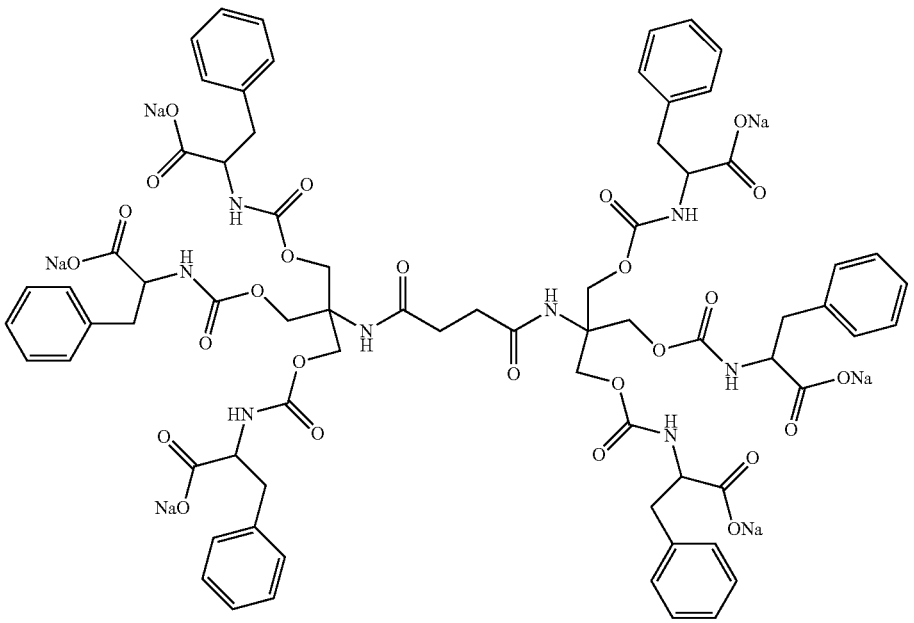 |
| A5 | 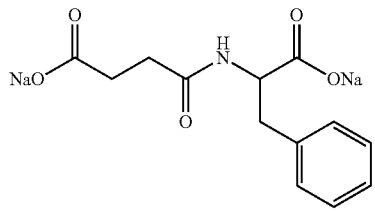 |
| A6 | 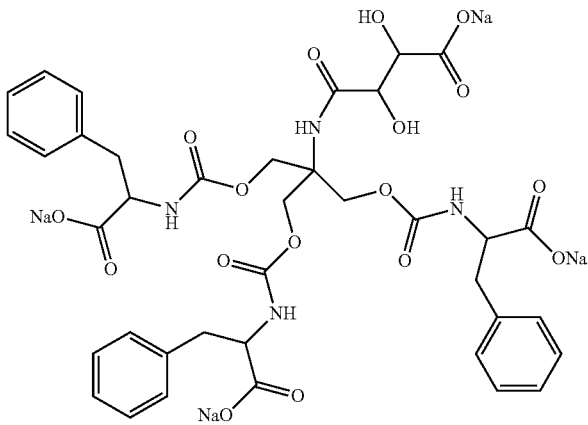 |

| Substituted anionic compounds | Formulations |
|---|---|
| A7 | (chemical structure) |

Part A: Synthesis of the Substituted Anionic Compounds

Example A1

Substituted Anionic Compound A1

The substituted anionic compound A1 or N-(3-carboxy-1-oxopropyl-)-L-phenylalanine is obtained according to a modification of the process described in patent application WO 96/33699 (Milstein, S.) from L-phenylalanine ethyl ester and O,O'-diacetyltartaric anhydride.
Yield: 6.7 g (26%)
$^1$H NMR (DMSO-$d_6$, ppm): 3.10 (2H); 4.20 (1H); 4.30 (1H); 4.50 (1H); 7.25 (5H); 7.70 (1H).

Example A2

Substituted Anionic Compound A2

Molecule 1

L-Phenylalanine Ethyl Ester Isocyanate

To a solution of the hydrochloride salt of L-phenylalanine ethyl ester (23 g, 100 mmol) in a mixture of dichloromethane (400 mL) and saturated aqueous sodium hydrogen carbonate solution (400 mL) at 0° C. is added one portion of triphosgene (9.8 g, 33 mmol). After stirring for 1 hour at 0° C., the organic phase is separated out and the aqueous phase is extracted 3 times with dichloromethane. The combined organic phases are dried over $Na_2SO_4$, filtered and concentrated to give a colorless oil which gradually crystallizes.
Yield: 22 g (quantitative)
$^1$H NMR (CDCl$_3$, ppm): 1.24 (3H); 2.98 (1H); 3.11 (1H); 4.17-4.23 (3H); 7.14-7.28 (5H).

Molecule 2

Product Obtained by Reaction Between Tris(Hydroxymethyl)Aminomethane and Monomethyl Succinate Via a process similar to that described in J. Org. Chem. 2011, 76, 2084 by reaction between tris(hydroxymethyl) aminomethane (2.66 g, 22 mmol) and monomethyl succinate (2.64 g, 20 mmol), a white solid is obtained.
Yield: 3.77 g (80%)
$^1$H NMR (CDCl$_3$, ppm): 2.52 (2H); 2.52 (2H); 3.64-3.70 (9H); 6.69 (1H).

Molecule 3

Product Obtained by Reaction Between Molecule 2 and Molecule 1

1,4-Diazobicyclo[2.2.2]octane (DABCO) (136 mg, 1.21 mmol) is added, under nitrogen, to a solution of molecule 2 (1.68 g, 7.14 mmol) and molecule 1 (5.63 g, 25.7 mmol) in toluene (70 mL), and the mixture is heated at 90° C. for 2.5 days. After concentrating the reaction medium under vacuum and coevaporation of the toluene with ethanol, the residue obtained is taken up in dichloromethane and washed with 1N HCl. The aqueous phase is extracted twice with dichloromethane. The organic phases are combined, dried over $Na_2SO_4$, filtered and concentrated under vacuum. Purification by flash chromatography (cyclohexane/ethyl acetate) leads to the desired product in the form of a colorless oil.
Yield: 5.15 g (80%)
$^1$H NMR (CDCl$_3$, ppm): 1.24 (9H); 2.39 (2H); 2.59 (2H); 2.90-3.15 (6H); 3.63 (3H); 4.10-4.30 (9H); 4.45-4.60 (6H); 6.07 (3H); 7.10-7.35 (15H).

Substituted Anionic Compound A2

A suspension of molecule 3 (10.2 g, 11.43 mmol) in an ethanol/tetrahydrofuran (THF)/water mixture (50 mL/32 mL/32 mL) is treated under nitrogen with 2N NaOH (23.4 mL) and then stirred at room temperature overnight. The volatile solvents are evaporated off under vacuum and 25 mL of 2N HCl are then gradually added to the medium. The medium is then extracted with ethyl acetate and the organic phase is dried over $Na_2SO_4$, filtered and concentrated under vacuum to give a foam. After triturating in pentane and ethyl ether, filtering and drying under vacuum, a white issue solid corresponding to the anionic molecule A2 in acid form is obtained. The solid is dissolved in a water/1-butanol mixture (50/50 vol/vol) and lyophilized.

Yield: 5.9 g (86%)

$^1$H NMR (DMSO-d$_6$, ppm): 2.10-2.20 (4H); 2.80-3.10 (6H); 4.00-4.20 (9H); 7.10-7.30 (15H); 7.50-7.60 (4H); 12.20-12.80 (4H).

LC/MS (ESI): 795.3; (calculated ([M+H]$^+$): 795.3).

The substituted anionic compound A2 in acid form is dissolved in water and the solution is neutralized by gradual addition of 10N sodium hydroxide to give an aqueous solution of substituted anionic compound A2, which is then lyophilized.

$^1$H NMR ((D$_2$O, ppm): 2.25-2.40 (4H); 2.75-2.90 (3H); 3.10-3.30 (3H); 3.75-4.30 (9H); 7.10-7.40 (15H).

Example A3

Substituted Anionic Compound A3

Molecule 4

Product Obtained by Reaction Between the Hydrochloride Salt of L-Phenylalanine Ethyl Ester and N-(Tert-Butoxycarbonyl)-L-Aspartic Acid A suspension of N-(tert-butoxycarbonyl)-L-aspartic acid (2.33 g, 10 mmol) in 120 mL of dichloromethane at 0° C. is treated, under nitrogen, with 1-ethyl-3-(3-dimethylaminopropyl)carbodiimide (EDCI) (5.75 g, 30 mmol). After stirring for 35 minutes, the hydrochloride salt of L-phenylalanine ethyl ester (6.89 g, 30 mmol), 1-hydroxybenzotriazole (HOBt) (4.05 g, 30 mmol) and diisopropylethylamine (DIPEA) (3.7 mL) are added and the mixture is stirred at room temperature overnight. The medium is neutralized by adding 150 mL of saturated aqueous NaHCO$_3$ solution and the medium is diluted with 150 mL of dichloromethane. The aqueous phase is extracted with dichloromethane. The organic phases are combined, washed with water, with saturated aqueous NaHCO$_3$ solution and with saturated aqueous NH$_4$Cl solution and then dried and concentrated under vacuum.

Yield: 8.02 g (quantitative)

$^1$H NMR (CDCl$_3$, ppm): 1.15-1.30 (6H); 1.42 (9H); 2.50-2.57 (1H); 2.83-2.89 (1H); 3.07-3.10 (4H); 4.05-4.22 (4H); 4.43 (1H); 4.73-4.83 (2H); 5.99-6.30 (1H); 6.27-6.29 (1H); 7.15-7.30 (10H).

Molecule 5

Hydrochloride Salt of the Product Obtained by Deprotection of the Boc Group of Molecule 4

A solution of molecule 4 (8 g, 10 mmol) in dichloromethane at 0° C. is treated, under nitrogen, with 4N HCl solution in dioxane (26 mL). After 5 hours at 0° C., the medium is concentrated under vacuum and coevaporated several times with dichloromethane to give a viscous foam.

Yield: 5.2 g (quantitative)

$^1$H NMR (DMSO-d$_6$, ppm): 1.05-1.15 (6H); 2.49-2.68 (1H); 2.79-2.86 (1H); 2.95-3.05 (4H); 3.99-4.07 (5H); 4.40-4.50 (2H); 7.20-7.36 (10H); 8.16 (3H); 8.89 (1H); 8.99 (1H).

Molecule 6

Product Obtained by Reaction Between Succinic Acid and Molecule 5

A suspension of succinic acid (0.33 g, 2.77 mmol) in dichloromethane (30 mL) at 0° C. is treated, under nitrogen, with EDCI (1.59 g, 8.3 mmol). After stirring for 35 minutes, a solution of molecule 5 (5.2 g, 10 mmol) in dichloromethane (10 mL), HOBt (1.12 g, 8.3 mmol) and DIPEA (1 mL) are added and the mixture is stirred at room temperature for 48 hours. The medium is diluted with dichloromethane and filtered through a sinter. The solid is washed with dichloromethane and then dried under vacuum to give a white solid.

Yield: 2.9 g (quantitative)

$^1$H NMR (DMSO-d$_5$, ppm): 0.95-1.15 (12H); 2.20-2.40 (8H); 2.80-3.10 (8H); 3.90-4.10 (8H); 4.30-4.50 (4H); 4.50-4.65 (4H); 7.10-7.40 (20H); 8.03 (2H); 8.13 (2H); 8.32 (2H).

Substituted Anionic Compound A3

A suspension of molecule 6 (2.9 g, 2.77 mmol) in a THF/ethanol/water mixture (50/50/25 mL) is treated, under nitrogen, with aqueous 2N NaOH solution (5.68 mL). After stirring at room temperature overnight, the reaction medium is filtered through a sinter and the filtrate is concentrated under vacuum. The aqueous phase obtained is acidified with 2N HCl and the precipitate formed is filtered off and then transferred into a round-bottomed flask with methanol. The solution is concentrated under vacuum and dried under vacuum to give a white solid of the substituted anionic compound A3 in acid form.

Yield: 1.98 g (76%)

$^1$H NMR (DMSO-d$_6$, ppm): 2.20-2.60 (8H); 2.80-3.10 (8H); 3.80-4.10 (8H); 4.30-4.45 (4H); 4.50-4.60 (2H); 7.10-7.35 (20H); 7.91 (2H); 8.06 (2H); 8.25 (2H).

LC/MS (ESI): 937.5; (calculated ([M+H]$^+$): 937.9).

The substituted anionic compound A3 in acid form is dissolved in water and the solution is neutralized by gradual addition of 10N sodium hydroxide to give an aqueous solution of anionic molecule A3, which is then lyophilized.

$^1$H NMR ((D$_2$O, ppm): 2.20-2.25 (4H); 2.45-2.55 (2H); 2.60-2.75 (2H); 2.75-3.00 (4H); 3.15-3.25 (4H); 4.30-4.45 (4H); 4.55-4.80 (2H); 7.10-7.35 (20H).

Example A4

Substituted Anionic Compound A4

Molecule 7

Product Obtained by Reaction Between Diethyl Succinate and Tris(Hydroxymethyl)Aminomethane A suspension of diethyl succinate (8.72 g, 50 mmol) and of tris(hydroxymethyl)aminomethane (12.72 g, 105 mmol) in an ethanol/water mixture (10/1 vol/vol) is heated, under nitrogen, at 100° C. for 7 hours and then at 60° C. for 2 days. The white precipitate formed is filtered off on a sinter, rinsed with ethanol and then dried under vacuum. The solid is taken up in an ethanol/water mixture (9/1 by vol) and then filtered off, rinsed with an ethanol/water mixture (9/1 by vol) and dried under vacuum.

Yield: 7.1 g (44%)

$^1$H NMR (DMSO-d$_6$, ppm): 2.54 (4H); 3.51 (12H); 4.65 (6H); 7.16 (2H).

Molecule 8

Product Obtained by Reaction Between Molecule 7 and Molecule 1

A suspension of molecule 7 (9.9 g, 30.5 mmol) and of molecule 1 (47 g, 213 mmol) in toluene is treated, under nitrogen, with 1,4-diazobicyclo[2.2.7]octane (DABCO)

(1.37 g, 12.2 mmol), and the mixture is heated at 110° C. for 6 hours and then at 90° C. overnight. The medium is concentrated under vacuum and then taken up in 750 mL of ethyl acetate and 250 mL of 1N HCl. The organic phase is washed with saturated NaCl solution, dried and concentrated under vacuum. The residue is purified by flash chromatography (cyclohexane/ethyl acetate).

Yield: 21.1 g (42%)

$^1$H NMR (CDCl$_3$, ppm): 1.22 (18H); 2.35 (4H); 2.90-3.15 (12H); 4.15-4.30 (18H); 4.40-4.65 (12H); 6.07 (6H); 7.10-7.35 (30H).

Anionic Molecule A4

A solution of molecule 8 (21.1 g, 12.8 mmol) in an ethanol/THF/water mixture (48/48/24 mL) is treated, under nitrogen, with aqueous 2N NaOH solution (42.2 mL). After stirring at room temperature for 24 hours, the reaction medium is concentrated under vacuum and the aqueous phase is acidified with 2N HCl. The precipitate is filtered off, rinsed with water and then taken up in water. The suspension is frozen and then lyophilized to give a white solid of anionic molecule A4 in acid form.

Yield: 18 g (95%)

$^1$H NMR (DMSO-d$_6$, ppm): 2.19 (4H); 2.75-3.10 (12H); 3.80-4.30 (18H); 7.10-7.30 (30H); 7.51 (8H).

LC/MS (ESI): 734.8; (calculated ([M/2]): 735.7).

The substituted anionic compound A4 in acid form is dissolved in water and the solution is neutralized by gradual addition of 10N sodium hydroxide to give an aqueous solution of anionic molecule A4, which is then lyophilized.

$^1$H NMR ((D$_2$O, ppm): 2.20 (4H); 2.75-2.95 (6H); 3.10-3.30 (6H); 3.80-4.35 (18H); 7.10-7.30 (30H).

Example A5

Substituted Anionic Compound A5

Triethylamine (30.6 g, 0.3 mol) is added to a solution of L-phenylalanine (25 g, 0.15 mol) in THF (200 mL) at room temperature, followed by addition of a solution of succinic anhydride (15.1 g, 0.15 mol) in THF (189 mL). The reaction medium is brought to the boiling point and heated for 16 hours. After cooling to room temperature, the medium is concentrated under vacuum to three-quarters of its volume and then acidified to pH 1.5 by adding 12N HCl. The aqueous phase is extracted with ethyl acetate. The organic phase is washed with 0.01N HCl and concentrated under vacuum to give a viscous yellow oil. This oil is taken up in water and the solution is stirred at pH 12 for 3 hours following the addition of 10N sodium hydroxide. The solution is then neutralized and then acidified by adding 12N HCl to pH 1.5. The solution is extracted with ethyl acetate, concentrated under vacuum and dried under vacuum to give a white solid of the substituted anionic compound A5 in acid form.

Yield: 26.9 g (67%)

$^1$H NMR (DMSO-d$_5$, ppm): 2.33 (4H); 2.75-3.15 (2H); 4.42 (1H); 7.21 (5H); 8.18 (1H); 12.38 (2H).

LC/MS (ESI): 266.2; (calculated ([M+H]$^+$): 266.3).

The substituted anionic compound A5 in acid form is dissolved in water and the solution is neutralized by gradual addition of 10N sodium hydroxide to give an aqueous solution of substituted anionic compound A5 or N-(β-carboxypropionyl)-L-phenylalanine, which is then lyophilized.

$^1$H NMR ((D$_2$O, ppm): 2.25-2.45 (4H); 2.65-2.92 (1H); 3.08-3.19 (1H); 4.35-4.45 (1H); 7.05-7.39 (5H)

Example A6

Substituted Anionic Compound A6

Molecule 9

Carbamic acid N-[2-hydroxy-1,1-bis(hydroxymethyl)ethyl]-1,1-dimethylethyl ester

Molecule 9 is obtained according to the process described in patent WO 2008/30119 starting with 20 g of tris(hydroxymethyl)aminomethane.

Yield: 33.2 g (88%)

$^1$H NMR (DMSO-d$_5$, ppm): 1.37 (9H); 3.50 (6H); 4.48 (3H); 5.76 (1H).

Molecule 10

Product Obtained by Reaction Between Molecule 1 and Molecule 9

1,4-Diazobicyclo[2.2.7]octane (DABCO) (795 µL, 7.2 mmol) is added to a solution of molecule 9 (4 g, 18.08 mmol) and of molecule 1 (11.87 g, 57.9 mmol) in toluene (260 mL), and the mixture is heated at 110° C. for 3 hours and then at 90° C. overnight. After concentrating under vacuum, the medium is taken up in ethyl acetate and then washed with 1N HCl. The organic phase is washed with saturated NaCl solution, dried over Na$_2$SO$_4$, filtered and concentrated under vacuum. The residue is purified by flash chromatography (cyclohexane/ethyl acetate).

Yield: 7.5 g (50%)

$^1$H NMR (CDCl$_3$, ppm): 1.41 (9H); 2.85-3.20 (6H); 3.73 (9H); 4.25 (3H); 4.39 (3H); 4.57 (3H); 5.72 (3H); 7.10-7.35 (15H).

LC/MS (ESI): 837.7; (calculated ([M+H]$^+$): 837.8).

Molecule 11

Hydrochloride Salt of the Product Obtained by Deprotection of the Boc Group of Molecule 10

A solution of molecule 10 (7.5 g, 9 mmol) in dichloromethane at 0° C. is treated, under argon, with 4N HCl solution in dioxane (22.4 mL). The medium is stirred from 0° C. to room temperature for 3 hours and is then concentrated under vacuum to give a white gum, which is dried under vacuum at room temperature for 15 hours.

Yield: 6.84 g (99%) $^1$H NMR (CDCl$_3$, ppm): 3.02-3.20 (6H); 3.73 (9H); 4.19 (3H); 4.42 (3H); 4.55 (3H); 5.72 (3H); 7.15-7.35 (15H); 8.93 (3H).

LC/MS (ESI): 737.4; (calculated ([M-Cl$^-$]): 737.7).

Molecule 12

Product Obtained by Reaction Between Molecule 11 and O,O'-Diacetyltartaric Anhydride Molecule 11 (5.7 g, 7.4 mmol) is dissolved in dichloromethane (50 mL) and saturated NaHCO$_3$ solution (30 mL) is added. The aqueous phase is extracted with dichloromethane and the organic phase is dried over Na$_2$SO$_4$, filtered and concentrated to a volume of about 20 mL. This solution is poured onto a solution of O,O'-diacetyltartaric anhydride (1.6 g, 7.4 mmol) in THF (35 mL) at 0° C. After stirring for 4 hours, the medium is concentrated under vacuum to give a white foam. The product is purified by flash chromatography (dichloromethane/methanol) to give a white foam.

Yield: 5.5 g (78%)

$^1$H NMR (CDCl$_3$, ppm): 2.05 (3H); 2.15 (3H); 2.93 (3H); 3.05 (3H); 3.73 (9H); 4.19 (3H); 4.50 (6H); 5.60 (1H); 5.69 (1H); 6.30 (3H); 7.15-7.35 (15H); 7.92 (1H).

LC/MS (ESI): 953.6; (calculated ([M+H]$^+$): 953.9).

Example A6

Substituted Anionic Compound A6

To a solution of molecules 12 (5.14 g, 5.39 mmol) in a methanol/water/THF mixture (18 mL/18 mL/18 mL) at 0° C. is added aqueous 2N sodium hydroxide solution (13.5 mL) and the mixture is stirred at 0° C. for 2 hours. After removal of the methanol and THF by evaporation under vacuum and washing of the solution with ethyl acetate, the solution is cooled to 0° C. and acidified to pH 1 by adding aqueous 10% HCl solution. The precipitated product is extracted with ethyl acetate 3×100 mL). The combined organic phases are dried over Na2SO4, filtered and concentrated under vacuum to give a white solid. The residue is taken up twice in a methanol/toluene mixture and then evaporated to dryness under vacuum. The solid is suspended in water and the mixture is lyophilized.

Yield: 3.8 g (85%)

LC/MS (ESI): 827.4; (calculated ([M+H]$^+$): 827.7).

The substituted anionic compound A6 (3.8 g) in acid form is suspended in water and 1.0025 M sodium hydroxide is gradually added to pH 7.18. After lyophilization, the desired product is obtained in the form of a white solid.

Yield: 4.09 g (83%)

$^1$H NMR (D$_2$O, 80° C., ppm): 3.45 (3H); 3.75 (3H); 4.55-4.75 (6H); 4.75-4.85 (4H); 5.00 (1H); 7.75-8.00 (15H).

LC/MS (ESI): 827.5; (calculated ([M+3H+−3Na+]): 827.7).

Example A7

Substituted Anionic Compound A7

Molecule 13

Product Obtained by Reaction Between Molecule 5 and O,O'-Diacetyltartaric Anhydride An aqueous solution (60 mL) of molecule 5 (4.99 g, 9.6 mmol) is poured into saturated NaHCO$_3$ solution (60 mL) and the mixture is extracted with dichloromethane (3×30 mL). The organic phase is dried over Na$_2$SO$_4$, filtered and concentrated to two-thirds of its volume under vacuum. It is added to a solution of O,O'-diacetyltartaric anhydride (2.07 g, 9.6 mmol) in THF at 0° C. and the mixture is stirred at 0° C. for 30 minutes. The mixture is concentrated under vacuum to obtain a white foam.

Yield: 6.45 g (96%)

$^1$H NMR (DMSO-d$_6$, ppm): 1.01-1.10 (6H); 2.00 (3H); 2.10 (3H); 2.43 (4H); 2.80-2.95 (4H); 3.60 (1H); 3.95-4.05 (4H); 4.39 (2H); 4.60 (1H); 5.50 (2H); 7.19-7.30 (10H); 8.25-8.40 (3H); 13.50 (1H).

LC/MS (ESI): 700.3; (calculated ([M+H]$^+$): 700.7).

Substituted Anionic Compound A7

To a solution of molecule 13 (5.39 g, 7.70 mmol) in a methanol/water mixture (38 mL/38 mL) at 0° C. is added aqueous 2N sodium hydroxide solution (15.4 mL) and the mixture is stirred at 0° C. for 1 hour. The methanol is removed under reduced pressure and the volume of water is reduced to about one third. The medium is acidified at 0° C. by slow addition of aqueous 10% HCl solution and is then extracted with ethyl acetate (3×50 mL). The organic phases are dried over Na$_2$SO$_4$ and evaporated under reduced pressure to give a white solid of the substituted anionic compound A7 in acid form, which is treated azeotropically 3 times with 50 mL of water to remove the traces of ethyl acetate and of acetic acid.

Yield: 3.24 g (75%)

$^1$H NMR (DMSO-d$_6$, ppm): 2.55 (1H); 2.65 (1H); 2.80-3.05 (4H); 3.35 (1H); 4.25-4.45 (4H); 4.58 (1H); 5.93 (1H); 7.19-7.30 (10H); 7.81 (1H); 8.10 (1H); 8.28 (1H); 12.65 (3H).

LC/MS (ESI): 560.1; (calculated ([M+H]$^+$): 560.5).

The substituted anionic compound A7 (3.24 g) in acid form is suspended in 50 mL of water and 0.521 M sodium hydroxide is added dropwise to pH 7.08. After lyophilization, the desired product is obtained in the form of a white solid.

Yield: 3.53 g (97%)

$^1$H NMR (MeOD-d$_4$, ppm): 2.61 (1H); 2.70 (1H); 2.95 (2H); 3.15 (2H); 4.29 (1H); 4.42 (3H); 4.64 (1H); 7.10-7.30 (10H).

LC/MS (ESI): 560.2; (calculated ([M+3H+−3Na+]): 559.4).

Part A': Synthesis of a Polyanionic Compound

Polyanionic Compound 1: Sodium Maltotriosemethylcarboxylate 0.6 g (16 mmol) of sodium borohydride is added to 8 g (143 mmol of hydroxyl functions) of maltotriose (Carbo-Synth) dissolved in water at 65° C. After stirring for 30 minutes, 28 g (238 mmol) of sodium chloroacetate are added. 24 mL of 10 N NaOH (240 mmol) are then added dropwise to this solution, and the mixture is then heated at 65° C. for 90 minutes. 16.6 g (143 mmol) of sodium chloride acetate are then added to the reaction medium, along with dropwise addition of 14 mL of 10 N NaOH (140 mmol). After heating for 1 hour, the mixture is diluted with water, neutralized with acetic acid and then purified by ultrafiltration on a 1 kDa PES membrane against water. The concentration of compound in the final solution is determined from the dry extract, and an acid/base titration in a 50/50 (V/V) water/acetone mixture is then performed to determine the degree of substitution with sodium methylcarboxylate.

According to the dry extract: [polyanionic compound 1]=32.9 mg/g

According to the acid/base titration: the degree of substitution with sodium methylcarboxylates per saccharide unit is 1.65.

The polyanionic compounds are selected by measuring their dissociation constant with respect to calcium ions and with respect to their capacity for not destabilizing the hexameric form of insulin.

As regards the dissociation constant with respect to calcium ions, it is determined as follows.

Solutions containing 2.5 mM of CaCl$_2$, 150 mM of NaCl and increasing concentrations (between 0 and 20 mM) of polyanionic compound are prepared. The potential of all these formulations is measured and the concentrations of free calcium ions in the formulations are determined. After linearization by the Scatchard method, the dissociation constants are established. These data make it possible to compare the affinity of the various polyanionic compounds for Ca.

Part B: Preparation of the Solutions

B1. Novolog® Rapid Insulin Analog Solution at 100 IU/mL
This solution is a commercial solution of aspart insulin from Novo Nordisk sold under the name Novolog®. This product is a rapid insulin analog.

B2. Humalog® Rapid Insulin Analog Solution at 100 IU/mL
This solution is a commercial solution of lispro insulin from Eli Lilly sold under the name Humalog®. This product is a rapid insulin analog.

B3. Humulin® R Human Insulin Solution at 100 IU/mL
This solution is a commercial solution of human insulin from Eli Lilly sold under the name Humulin® R. This product is a human insulin composition.

B4. Apidra® Rapid Insulin Analog Solution at 100 IU/mL
This solution is a commercial solution of glulisine insulin from Sanofi sold under the name Apidra®. This product is a rapid insulin analog.

B5. Preparation of a 1.188 M Sodium Citrate Solution
The sodium citrate solution is obtained by dissolving 9.0811 g of sodium citrate (30.9 mmol) in 25 mL of water in a graduated flask. The pH is adjusted to 7.4 by adding 1 mL of 1 M HCl. The solution is filtered through a 0.22 μm membrane.

B7. Preparation of a Solution of Lispro Insulin at 100 IU/mL in the Presence of the Substituted Anionic Compound A1 and Citrate
For a final volume of 100 mL of composition, with a [substituted anionic compound A1]/[lispro insulin] mass ratio of 2.0 and a concentration of 9.3 mM of citrate, the various reagents are added in the amounts specified in the table and in the following order

| | |
|---|---|
| Lyophilized compound (substituted anionic compound A1) | 730 mg |
| Commercial solution of Humalog® | 100 mL |
| Sodium citrate solution at 1.188M | 783 μL |

The final pH is adjusted to 7.4±0.4.
The clear solution is filtered through a 0.22 μm membrane and stored at 4° C.

B8. Preparation of a Solution of Human Insulin at 100 IU/mL in the Presence of the Substituted Anionic Compound A1 and Citrate
For a final volume of 100 mL of composition, with a [substituted anionic compound A1]/[human insulin] mass ratio of 2.0 and a concentration of 9.3 mM of citrate, the various reagents are added in the amounts specified in the table and in the following order

| | |
|---|---|
| Lyophilized compound (substituted anionic compound A1) | 730 mg |
| Commercial solution of Humulin® R | 100 mL |
| Sodium citrate solution at 1.188M | 783 μL |

The final pH is adjusted to 7.4±0.4.
The clear solution is filtered through a 0.22 μm membrane and stored at 4° C.

B9. Preparation of a Solution of Aspart Insulin at 100 IU/mL in the Presence of the Substituted Anionic Compound A1 and Citrate
For a final volume of 100 mL of composition, with a [substituted anionic compound A1]/[aspart insulin] mass ratio of 2.0 and a concentration of 9.3 mM of citrate, the various reagents are added in the amounts specified in the table and in the following order

| | |
|---|---|
| Lyophilized compound (substituted anionic compound A1) | 730 mg |
| Commercial solution of Novolog® | 100 mL |
| Sodium citrate solution at 1.188M | 783 μL |

The final pH is adjusted to 7.4±0.4.
The clear solution is filtered through a 0.22 μm membrane and stored at 4° C.

B10. Preparation of a Solution of Glulisine Insulin at 100 IU/mL in the Presence of the Substituted Anionic Compound A1 and Citrate
For a final volume of 100 mL of composition, with a [substituted anionic compound A1]/[glulisine insulin] mass ratio of 2.0 and a concentration of 9.3 mM of citrate, the various reagents are added in the amounts specified in the table and in the following order

| | |
|---|---|
| Lyophilized compound (substituted anionic compound A1) | 730 mg |
| Commercial solution of Apidra® | 100 mL |
| Sodium citrate solution at 1.188M | 783 μL |

The final pH is adjusted to 7.4±0.4.
The clear solution is filtered through a 0.22 μm membrane and stored at 4° C.

B12. Preparation of a Solution of Lispro Insulin at 100 IU/mL in the Presence of the Substituted Anionic Compound A2 and Citrate
For a final volume of 100 mL of composition, with a [substituted anionic compound A2]/[lispro insulin] mass ratio of 2.0 and a concentration of 9.3 mM of citrate, the various reagents are added in the amounts specified in the table and in the following order

| | |
|---|---|
| Lyophilized compound (substituted anionic compound A2) | 730 mg |
| Commercial solution of Humalog® | 100 mL |
| Sodium citrate solution at 1.188M | 783 μL |

The final pH is adjusted to 7.4±0.4.
The clear solution is filtered through a 0.22 μm membrane and stored at 4° C.

B13. Preparation of a Solution of Human Insulin at 100 IU/mL in the Presence of the Substituted Anionic Compound A2 and Citrate
For a final volume of 100 mL of composition, with a [substituted anionic compound A2]/[human insulin] mass ratio of 2.0 and a concentration of 9.3 mM of citrate, the various reagents are added in the amounts specified in the table and in the following order

| | |
|---|---|
| Lyophilized compound (substituted anionic compound A2) | 730 mg |
| Commercial solution of Humulin® R | 100 mL |
| Sodium citrate solution at 1.188M | 783 μL |

The final pH is adjusted to 7.4±0.4.
The clear solution is filtered through a 0.22 μm membrane and stored at 4° C.

B14. Preparation of a Solution of Aspart Insulin at 100 IU/mL in the Presence of the Substituted Anionic Compound A2 and Citrate
For a final volume of 100 mL of composition, with a [substituted anionic compound A2]/[aspart insulin] mass ratio of 2.0 and a concentration of 9.3 mM of citrate, the various reagents are added in the amounts specified in the table and in the following order

| | |
|---|---|
| Lyophilized compound (substituted anionic compound A2) | 730 mg |
| Commercial solution of Novolog ® | 100 mL |
| Sodium citrate solution at 1.188M | 783 μL |

The final pH is adjusted to 7.4±0.4.
The clear solution is filtered through a 0.22 μm membrane and stored at 4° C.

B15. Preparation of a Solution of Glulisine Insulin at 100 IU/mL in the Presence of the Substituted Anionic Compound A2 and Citrate For a final volume of 100 mL of composition, with a [substituted anionic compound A2]/[glulisine insulin] mass ratio of 2.0 and a concentration of 9.3 mM of citrate, the various reagents are added in the amounts specified in the table and in the following order

| | |
|---|---|
| Lyophilized compound (substituted anionic compound A2) | 730 mg |
| Commercial solution of Apidra ® | 100 mL |
| Sodium citrate solution at 1.188M | 783 μL |

The final pH is adjusted to 7.4±0.4.
The clear solution is filtered through a 0.22 μm membrane and stored at 4° C.

B17. Preparation of a Solution of Lispro Insulin at 100 IU/mL in the Presence of the Substituted Anionic Compound A3 and Citrate For a final volume of 100 mL of composition, with a [substituted anionic compound A3]/[lispro insulin] mass ratio of 2.0 and a concentration of 9.3 mM of citrate, the various reagents are added in the amounts specified in the table and in the following order

| | |
|---|---|
| Lyophilized compound (substituted anionic compound A3) | 730 mg |
| Commercial solution of Humalog ® | 100 mL |
| Sodium citrate solution at 1.188M | 783 μL |

The final pH is adjusted to 7.4±0.4.
The clear solution is filtered through a 0.22 μm membrane and stored at 4° C.

B18. Preparation of a Solution of Human Insulin at 100 IU/mL in the Presence of the Substituted Anionic Compound A3 and Citrate For a final volume of 100 mL of composition, with a [substituted anionic compound A3]/[human insulin] mass ratio of 2.0 and a concentration of 9.3 mM of citrate, the various reagents are added in the amounts specified in the table and in the following order

| | |
|---|---|
| Lyophilized compound (substituted anionic compound A3) | 730 mg |
| Commercial solution of Humulin ® R | 100 mL |
| Sodium citrate solution at 1.188M | 783 μL |

The final pH is adjusted to 7.4±0.4.
The clear solution is filtered through a 0.22 μm membrane and stored at 4° C.

B19. Preparation of a Solution of Aspart Insulin at 100 IU/mL in the Presence of the Substituted Anionic Compound A3 and Citrate For a final volume of 100 mL of composition, with a [substituted anionic compound A3]/[aspart insulin] mass ratio of 2.0 and a concentration of 9.3 mM of citrate, the various reagents are added in the amounts specified in the table and in the following order

| | |
|---|---|
| Lyophilized compound (substituted anionic compound A3) | 730 mg |
| Commercial solution of Novolog ® | 100 mL |
| Sodium citrate solution at 1.188M | 783 μL |

The final pH is adjusted to 7.4±0.4.
The clear solution is filtered through a 0.22 μm membrane and stored at 4° C.

B20. Preparation of a Solution of Glulisine Insulin at 100 IU/mL in the Presence of the Substituted Anionic Compound A3 and Citrate For a final volume of 100 mL of composition, with a [substituted anionic compound A3]/[glulisine insulin] mass ratio of 2.0 and a concentration of 9.3 mM of citrate, the various reagents are added in the amounts specified in the table and in the following order

| | |
|---|---|
| Lyophilized compound (substituted anionic compound A3) | 730 mg |
| Commercial solution of Apidra ® | 100 mL |
| Sodium citrate solution at 1.188M | 783 μL |

The final pH is adjusted to 7.4±0.4.
The clear solution is filtered through a 0.22 μm membrane and stored at 4° C.

B22. Preparation of a Solution of Lispro Insulin at 100 IU/mL in the Presence of the Substituted Anionic Compound A4 and Citrate For a final volume of 100 mL of composition, with a [substituted anionic compound A4]/[lispro insulin] mass ratio of 2.0 and a concentration of 9.3 mM of citrate, the various reagents are added in the amounts specified in the table and in the following order

| | |
|---|---|
| Lyophilized compound (substituted anionic compound A4) | 730 mg |
| Commercial solution of Humalog ® | 100 mL |
| Sodium citrate solution at 1.188M | 783 μL |

The final pH is adjusted to 7.4±0.4.
The clear solution is filtered through a 0.22 μm membrane and stored at 4° C.

B23. Preparation of a Solution of Human Insulin at 100 IU/mL in the Presence of the Substituted Anionic Compound A4 and Citrate For a final volume of 100 mL of composition, with a [substituted anionic compound A4]/[human insulin] mass ratio of 2.0 and a concentration of 9.3 mM of citrate, the various reagents are added in the amounts specified in the table and in the following order

| | |
|---|---|
| Lyophilized compound (substituted anionic compound A4) | 730 mg |
| Commercial solution of Humalog ® | 100 mL |
| Sodium citrate solution at 1.188M | 783 μL |

The final pH is adjusted to 7.4±0.4.
The clear solution is filtered through a 0.22 μm membrane and stored at 4° C.

B24. Preparation of a Solution of Aspart Insulin at 100 IU/mL in the Presence of the Substituted Anionic Compound A4 and Citrate For a final volume of 100 mL of composition, with a [substituted anionic compound A4]/[aspart insulin] mass ratio of 2.0 and a concentration of 9.3 mM of citrate, the various reagents are added in the amounts specified in the table and in the following order

| Lyophilized compound (substituted anionic compound A4) | 730 mg |
| Commercial solution of Novolog ® | 100 mL |
| Sodium citrate solution at 1.188M | 783 µL |

The final pH is adjusted to 7.4±0.4.

The clear solution is filtered through a 0.22 µm membrane and stored at 4° C.

B25. Preparation of a Solution of Glulisine Insulin at 100 IU/mL in the Presence of the Substituted Anionic Compound A4 and Citrate For a final volume of 100 mL of composition, with a [substituted anionic compound A4]/[glulisine insulin] mass ratio of 2.0 and a concentration of 9.3 mM of citrate, the various reagents are added in the amounts specified in the table and in the following order

| Lyophilized compound (substituted anionic compound A4) | 730 mg |
| Commercial solution of Apidra ® | 100 mL |
| Sodium citrate solution at 1.188M | 783 µL |

The final pH is adjusted to 7.4±0.4.

The clear solution is filtered through a 0.22 µm membrane and stored at 4° C.

B26. Preparation of a Solution of Lispro Insulin at 100 IU/mL in the Presence of Compound A4 and of the Polyanionic Compound 1

For a final volume of 100 mL of formulation, with a [compound A1]/[polyanionic compound 1]/[lispro insulin] mass ratio of 2.0/2.0/1, the various reagents are added in the amounts specified below and in the following order:

| Lyophilized compound A1 | 730 mg |
| Lyophilized polyanionic compound 1 | 730 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B27. Preparation of a Solution of Lispro Insulin at 100 IU/mL in the Presence of Compound A1 and of the Polyanionic Compound 1

For a final volume of 100 mL of formulation, with a [compound A1]/[polyanionic compound 1]/[lispro insulin] mass ratio of 2/4/1, the various reagents are added in the amounts specified below:

| Compound A1 in lyophilized form | 730 mg |
| Polyanionic compound 1 in lyophilized form | 1460 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B28. Preparation of a Solution of Lispro Insulin at 100 IU/mL in the Presence of Compound A4 and of the Polyanionic Compound 1

For a final volume of 100 mL of formulation, with a [compound A1]/[polyanionic compound 1]/[lispro insulin] mass ratio of 2.0/5.5/1, the various reagents are added in the amounts specified below and in the following order:

| Lyophilized compound A1 | 730 mg |
| Lyophilized polyanionic compound 1 | 2000 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B29. Preparation of a Solution of Lispro Insulin at 100 IU/mL in the Presence of Compound A2 and of the Polyanionic Compound 1

For a final volume of 100 mL of formulation, with a [compound A2]/[polyanionic compound 1]/[lispro insulin] mass ratio of 2.0/2.0/1, the various reagents are added in the amounts specified below and in the following order:

| Lyophilized compound A2 | 730 mg |
| Lyophilized polyanionic compound 1 | 730 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B30. Preparation of a Solution of Lispro Insulin at 100 IU/mL in the Presence of Compound A2 and of the Polyanionic Compound 1

For a final volume of 100 mL of formulation, with a [compound A2]/[polyanionic compound 1]/[lispro insulin] mass ratio of 2/4/1, the various reagents are added in the amounts specified below:

| Compound A2 in lyophilized form | 730 mg |
| Polyanionic compound 1 in lyophilized form | 1460 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B31. Preparation of a Solution of Lispro Insulin at 100 IU/mL in the Presence of Compound A2 and of the Polyanionic Compound 1

For a final volume of 100 mL of formulation, with a [compound A2]/[polyanionic compound 1]/[lispro insulin] mass ratio of 2.0/5.5/1, the various reagents are added in the amounts specified below and in the following order:

| | |
|---|---|
| Lyophilized compound A2 | 730 mg |
| Lyophilized polyanionic compound 1 | 2000 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B32. Preparation of a Solution of Lispro Insulin at 100 IU/mL in the Presence of Compound A3 and of the Polyanionic Compound 1

For a final volume of 100 mL of formulation, with a [compound A3]/[polyanionic compound 1]/[lispro insulin] mass ratio of 2.0/2.0/1, the various reagents are added in the amounts specified below and in the following order:

| | |
|---|---|
| Lyophilized compound A3 | 730 mg |
| Lyophilized polyanionic compound 1 | 730 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B33. Preparation of a Solution of Lispro Insulin at 100 IU/mL in the Presence of Compound A3 and of the Polyanionic Compound 1

For a final volume of 100 mL of formulation, with a [compound A3]/[polyanionic compound 1]/[lispro insulin] mass ratio of 2/4/1, the various reagents are added in the amounts specified below:

| | |
|---|---|
| Compound A3 in lyophilized form | 730 mg |
| Polyanionic compound 1 in lyophilized form | 1460 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B34. Preparation of a Solution of Lispro Insulin at 100 IU/mL in the Presence of Compound A3 and of the Polyanionic Compound 1

For a final volume of 100 mL of formulation, with a [compound A3]/[polyanionic compound 1]/[lispro insulin] mass ratio of 2.0/5.5/1, the various reagents are added in the amounts specified below and in the following order:

| | |
|---|---|
| Lyophilized compound A3 | 730 mg |
| Lyophilized polyanionic compound 1 | 2000 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B35. Preparation of a Solution of Lispro Insulin at 100 IU/mL in the Presence of Compound A4 and of the Polyanionic Compound 1

For a final volume of 100 mL of formulation, with a [compound A4]/[polyanionic compound 1]/[lispro insulin] mass ratio of 2.0/2.0/1, the various reagents are added in the amounts specified below and in the following order:

| | |
|---|---|
| Lyophilized compound A4 | 730 mg |
| Lyophilized polyanionic compound 1 | 730 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B36. Preparation of a Solution of Lispro Insulin at 100 IU/mL in the Presence of Compound A4 and of the Polyanionic Compound 1

For a final volume of 100 mL of formulation, with a [compound A4]/[polyanionic compound 1]/[lispro insulin] mass ratio of 2/4/1, the various reagents are added in the amounts specified below:

| | |
|---|---|
| Compound A4 in lyophilized form | 730 mg |
| Polyanionic compound 1 in lyophilized form | 1460 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B37. Preparation of a Solution of Lispro Insulin at 100 IU/mL in the Presence of Compound A4 and of the Polyanionic Compound 1

For a final volume of 100 mL of formulation, with a [compound A4]/[polyanionic compound 1]/[lispro insulin] mass ratio of 2.0/5.5/1, the various reagents are added in the amounts specified below and in the following order:

| | |
|---|---|
| Lyophilized compound A4 | 730 mg |
| Lyophilized polyanionic compound 1 | 2000 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B39. Preparation of a Solution of Lispro Insulin at 100 IU/mL in the Presence of the Substituted Anionic Compound A5 and Citrate For a final volume of 100 mL of formulation, with a [substituted anionic compound A5]/[lispro insulin] mass ratio of 2.0 and a concentration of 9.3 mM of citrate, the various reagents are added in the amounts specified below and in the following order:

| | |
|---|---|
| Lyophilized substituted anionic compound A5 | 730 mg |
| Commercial solution of Humalog ® at 100 IU/mL | 100 mL |
| Sodium citrate solution at 1.188M | 783 µL |

Citrate may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B40. Preparation of a Solution of Human Insulin at 100 IU/mL in the Presence of the Substituted Anionic Compound A5 and Citrate For a final volume of 100 mL of formulation, with a [substituted anionic compound A5]/[human insulin] mass ratio of 2.0 and a concentration of 9.3 mM of citrate, the various reagents are added in the amounts specified below and in the following order:

| | |
|---|---|
| Lyophilized substituted anionic compound A5 | 730 mg |
| Commercial solution of Humulin ® R | 100 mL |
| Sodium citrate solution at 1.188M | 783 µL |

Citrate may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B41. Preparation of a Solution of Aspart Insulin at 100 IU/mL in the Presence of the Substituted Anionic Compound A5 and Citrate For a final volume of 100 mL of formulation, with a [substituted anionic compound A5]/[aspart insulin] mass ratio of 2.0 and a concentration of 9.3 mM of citrate, the various reagents are added in the amounts specified below and in the following order:

| | |
|---|---|
| Lyophilized substituted anionic compound A5 | 730 mg |
| Commercial solution of Novolog ® | 100 mL |
| Sodium citrate solution at 1.188M | 783 µL |

Citrate may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B42. Preparation of a Solution of Glulisine Insulin at 100 IU/mL in the Presence of the Substituted Anionic Compound A5 and Citrate For a final volume of 100 mL of formulation, with a [substituted anionic compound A5]/[glulisine insulin] mass ratio of 2.0 and a concentration of 9.3 mM of citrate, the various reagents are added in the amounts specified below and in the following order:

| | |
|---|---|
| Lyophilized substituted anionic compound A5 | 730 mg |
| Commercial solution of Apidra ® | 100 mL |
| Sodium citrate solution at 1.188M | 783 µL |

Citrate may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B43. Preparation of a Solution of Lispro Insulin at 100 IU/mL in the Presence of Compound A5 and of the Polyanionic Compound 1

For a final volume of 100 mL of formulation, with a [compound A5]/[polyanionic compound 1]/[lispro insulin] mass ratio of 2.0/2.0/1, the various reagents are added in the amounts specified below and in the following order:

| | |
|---|---|
| Lyophilized compound A5 | 730 mg |
| Lyophilized polyanionic compound 1 | 730 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B44. Preparation of a Solution of Lispro Insulin at 100 IU/mL in the Presence of Compound A5 and of the Polyanionic Compound 1

For a final volume of 100 mL of formulation, with a [compound A5]/[polyanionic compound 1]/[lispro insulin] mass ratio of 2/4/1, the various reagents are added in the amounts specified below:

| | |
|---|---|
| Compound A5 in lyophilized form | 730 mg |
| Polyanionic compound 1 in lyophilized form | 1460 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B45. Preparation of a Solution of Lispro Insulin at 100 IU/mL in the Presence of Compound A5 and of the Polyanionic Compound 1

For a final volume of 100 mL of formulation, with a [compound A5]/[polyanionic compound 1]/[lispro insulin] mass ratio of 2.0/5.5/1, the various reagents are added in the amounts specified below and in the following order:

| | |
|---|---|
| Lyophilized compound A5 | 730 mg |
| Lyophilized polyanionic compound 1 | 2000 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B47. Preparation of a Solution of Lispro Insulin at 100 IU/mL in the Presence of the Substituted Anionic Compound A6 and Citrate For a final volume of 100 mL of formulation, with a [substituted anionic compound A6]/[lispro insulin] mass ratio of 2.0 and a concentration of 9.3 mM of citrate, the various reagents are added in the amounts specified below and in the following order:

| Lyophilized substituted anionic compound A6 | 730 mg |
| Commercial solution of Humalog ® at 100 IU/mL | 100 mL |
| Sodium citrate solution at 1.188M | 783 µL |

Citrate may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B48. Preparation of a Solution of Human Insulin at 100 IU/mL in the Presence of the Substituted Anionic Compound A6 and Citrate For a final volume of 100 mL of formulation, with a [substituted anionic compound A6]/[human insulin] mass ratio of 2.0 and a concentration of 9.3 mM of citrate, the various reagents are added in the amounts specified below and in the following order:

| Lyophilized substituted anionic compound A6 | 730 mg |
| Commercial solution of Humulin ® R | 100 mL |
| Sodium citrate solution at 1.188M | 783 µL |

Citrate may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B49. Preparation of a Solution of Aspart Insulin at 100 IU/mL in the Presence of the Substituted Anionic Compound A6 and Citrate For a final volume of 100 mL of formulation, with a [substituted anionic compound A6]/[aspart insulin] mass ratio of 2.0 and a concentration of 9.3 mM of citrate, the various reagents are added in the amounts specified below and in the following order:

| Lyophilized substituted anionic compound A6 | 730 mg |
| Commercial solution of Novolog ® | 100 mL |
| Sodium citrate solution at 1.188M | 783 µL |

Citrate may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B50. Preparation of a Solution of Glulisine Insulin at 100 IU/mL in the Presence of the Substituted Anionic Compound A6 and Citrate For a final volume of 100 mL of formulation, with a [substituted anionic compound A6]/[glulisine insulin] mass ratio of 2.0 and a concentration of 9.3 mM of citrate, the various reagents are added in the amounts specified below and in the following order:

| Lyophilized substituted anionic compound A6 | 730 mg |
| Commercial solution of Apidra ® | 100 mL |
| Sodium citrate solution at 1.188M | 783 µL |

Citrate may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B51. Preparation of a Solution of Lispro Insulin at 100 IU/mL in the Presence of Compound A6 and of the Polyanionic Compound 1

For a final volume of 100 mL of formulation, with a [compound A6]/[polyanionic compound 1]/[lispro insulin] mass ratio of 2.0/2.0/1, the various reagents are added in the amounts specified below and in the following order:

| Lyophilized compound A6 | 730 mg |
| Lyophilized polyanionic compound 1 | 730 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B52. Preparation of a Solution of Lispro Insulin at 100 IU/mL in the Presence of Compound A6 and of the Polyanionic Compound 1

For a final volume of 100 mL of formulation, with a [compound A6]/[polyanionic compound 1]/[lispro insulin] mass ratio of 2/4/1, the various reagents are added in the amounts specified below:

| Compound A6 in lyophilized form | 730 mg |
| Polyanionic compound 1 in lyophilized form | 1460 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B53. Preparation of a Solution of Lispro Insulin at 100 IU/mL in the Presence of Compound A6 and of the Polyanionic Compound 1

For a final volume of 100 mL of formulation, with a [compound A6]/[polyanionic compound 1]/[lispro insulin] mass ratio of 2.0/5.5/1, the various reagents are added in the amounts specified below and in the following order:

| Lyophilized compound A6 | 730 mg |
|---|---|
| Lyophilized polyanionic compound 1 | 2000 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B55. Preparation of a Solution of Lispro Insulin at 100 IU/mL in the Presence of the Substituted Anionic Compound A7 and Citrate For a final volume of 100 mL of formulation, with a [substituted anionic compound A7]/[lispro insulin] mass ratio of 2.0 and a concentration of 9.3 mM of citrate, the various reagents are added in the amounts specified below and in the following order:

| Lyophilized substituted anionic compound A7 | 730 mg |
|---|---|
| Commercial solution of Humalog ® at 100 IU/mL | 100 mL |
| Sodium citrate solution at 1.188M | 783 μL |

Citrate may be used in the acid form or in the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B56. Preparation of a Solution of Human Insulin at 100 IU/mL in the Presence of the Substituted Anionic Compound A7 and Citrate For a final volume of 100 mL of formulation, with a [substituted anionic compound A7]/[human insulin] mass ratio of 2.0 and a concentration of 9.3 mM of citrate, the various reagents are added in the amounts specified below and in the following order:

| Lyophilized substituted anionic compound A7 | 730 mg |
|---|---|
| Commercial solution of Humulin ® R | 100 mL |
| Sodium citrate solution at 1.188M | 783 μL |

Citrate may be used in the acid form or in the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B57. Preparation of a Solution of Aspart Insulin at 100 IU/mL in the Presence of the Substituted Anionic Compound A7 and Citrate For a final volume of 100 mL of formulation, with a [substituted anionic compound A7]/[aspart insulin] mass ratio of 2.0 and a concentration of 9.3 mM of citrate, the various reagents are added in the amounts specified below and in the following order:

| Lyophilized substituted anionic compound A7 | 730 mg |
|---|---|
| Commercial solution of Novolog ® | 100 mL |
| Sodium citrate solution at 1.188M | 783 μL |

Citrate may be used in the acid form or in the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B58. Preparation of a Solution of Glulisine Insulin at 100 IU/mL in the Presence of the Substituted Anionic Compound A7 and Citrate For a final volume of 100 mL of formulation, with a [substituted anionic compound A7]/[glulisine insulin] mass ratio of 2.0 and a concentration of 9.3 mM of citrate, the various reagents are added in the amounts specified below and in the following order:

| Lyophilized substituted anionic compound A7 | 730 mg |
|---|---|
| Commercial solution of Apidra ® | 100 mL |
| Sodium citrate solution at 1.188M | 783 μL |

Citrate may be used in the acid form or in the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B59. Preparation of a Solution of Lispro Insulin at 100 IU/mL in the Presence of Compound A7 and of the Polyanionic Compound 1

For a final volume of 100 mL of formulation, with a [compound A7]/[polyanionic compound 1]/[lispro insulin] mass ratio of 2.0/2.0/1, the various reagents are added in the amounts specified below and in the following order:

| Lyophilized compound A7 | 730 mg |
|---|---|
| Lyophilized polyanionic compound 1 | 730 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B60. Preparation of a Solution of Lispro Insulin at 100 IU/mL in the Presence of Compound A7 and of the Polyanionic Compound 1

For a final volume of 100 mL of formulation, with a [compound A7]/[polyanionic compound 1]/[lispro insulin] mass ratio of 2/4/1, the various reagents are added in the amounts specified below:

| Compound A7 in lyophilized form | 730 mg |
|---|---|
| Polyanionic compound 1 in lyophilized form | 1460 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B61. Preparation of a Solution of Lispro Insulin at 100 IU/mL in the Presence of Compound A6 and of the Polyanionic Compound 1

For a final volume of 100 mL of formulation, with a [compound A7]/[polyanionic compound 1]/[lispro insulin] mass ratio of 2.0/5.5/1, the various reagents are added in the amounts specified below and in the following order:

| | |
|---|---|
| Lyophilized compound A7 | 730 mg |
| Lyophilized polyanionic compound 1 | 2000 mg |
| Commercial solution of Humalog ® at 100 IU/mL | 100 mL |

The polyanionic compound 1 may be used in the acid form or in the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B62. Preparation of a Solution of Insulin Analog (Lispro Insulin) at 200 IU/mL The commercial formulation of lispro insulin (Humalog®) was concentrated using Amicon Ultra-15 centrifugation tubes with a cut-off threshold of 3 kDa. The Amicon tubes were first rinsed with 12 mL of deionized water. 12 mL of the commercial formulation were centrifuged for 35 minutes at 4000 g at 20° C. The volume of the retentate was measured and the concentration thus determined. All the retentates were pooled and the global concentration was estimated (>200 IU/mL).

The concentration of this concentrated lispro insulin solution was adjusted to 200 IU/mL by addition of the commercial formulation of lispro insulin (Humalog®). The concentrated lispro insulin formulation has the same concentrations of excipients (m-cresol, glycerol, phosphate) as the commercial formulation at 100 IU/mL.

The final pH is adjusted to 7.4±0.4. The clear solution is filtered through a 0.22 μm membrane and stored at 4° C.

B63. Preparation of a Solution of Human Insulin at 200 IU/mL

The commercial formulation of human insulin (Humulin® R) was concentrated using Amicon Ultra-15 centrifugation tubes with a cut-off threshold of 3 kDa. The Amicon tubes were first rinsed with 12 mL of deionized water. 12 mL of the commercial formulation were centrifuged for 35 minutes at 4000 g at 20° C. The volume of the retentate was measured and the concentration thus determined. All the retentates were pooled and the global concentration was estimated (>200 IU/mL).

The concentration of this concentrated human insulin solution was adjusted to 200 IU/mL by addition of the commercial formulation of human insulin (Humulin® R). The concentrated human insulin formulation has the same concentrations of excipients (m-cresol, glycerol) as the commercial formulation at 100 IU/mL.

The final pH is adjusted to 7.4±0.4. The clear solution is filtered through a 0.22 μm membrane and stored at 4° C.

B64. Preparation of a Solution of Aspart Insulin at 200 IU/mL

The commercial formulation of aspart insulin (Novolog®) was concentrated using Amicon Ultra-15 centrifugation tubes with a cut-off threshold of 3 kDa. The Amicon tubes were first rinsed with 12 mL of deionized water. 12 mL of the commercial formulation were centrifuged for 35 minutes at 4000 g at 20° C. The volume of the retentate was measured and the concentration thus determined. All the retentates were pooled and the global concentration was estimated (>200 IU/mL).

The concentration of this concentrated aspart insulin solution was adjusted to 200 IU/mL by addition of the commercial formulation of aspart insulin (Novolog®). The concentrated aspart insulin formulation has the same concentrations of excipients (m-cresol, glycerol) as the commercial formulation at 100 IU/mL.

The final pH is adjusted to 7.4±0.4. The clear solution is filtered through a 0.22 μm membrane and stored at 4° C.

B65. Preparation of a Solution of Glulisine Insulin at 200 IU/mL

The commercial formulation of glulisine insulin (Apidra®) was concentrated using Amicon Ultra-15 centrifugation tubes with a cut-off threshold of 3 kDa. The Amicon tubes were first rinsed with 12 mL of deionized water. 12 mL of the commercial formulation were centrifuged for 35 minutes at 4000 g at 20° C. The volume of the retentate was measured and the concentration thus determined. All the retentates were pooled and the global concentration was estimated (>200 IU/mL).

The concentration of this concentrated glulisine insulin solution was adjusted to 200 IU/mL by addition of the commercial formulation of glulisine insulin (Apidra®). The concentrated glulisine insulin formulation has the same concentrations of excipients (m-cresol, NaCl, TRIS) as the commercial formulation at 100 IU/mL.

The final pH is adjusted to 7.4±0.4. The clear solution is filtered through a 0.22 μm membrane and stored at 4° C.

B66. Preparation of a Solution of Human Insulin, of Lispro Insulin, of Aspart Insulin or of Glulisine Insulin at 300, 400 and 500 IU/mL Concentrated formulations of human insulin, of lispro insulin, of aspart insulin or of glulisine insulin at 300 IU/mL, 400 IU/mL or 500 IU/mL (and also at all intermediate concentrations) are prepared on the basis of the protocol of Example B65 relating to the preparation of a glulisine insulin solution at 200 IU/mL. The commercial insulin formulation is concentrated using Amicon Ultra-15 centrifugation tubes with a cut-off threshold of 3 kDa. The Amicon tubes are first rinsed with 12 mL of deionized water. 12 mL of the commercial formulation are centrifuged at 4000 g and at 20° C. By modifying the centrifugation time, it is possible to adjust the final concentration of insulin in the formulation. The volume of the retentate is measured and the concentration is thus estimated. All the retentates are pooled and the global concentration is estimated (>300, 400 or 500 IU/mL).

The concentration of this concentrated insulin solution is adjusted to the desired concentration (e.g. 300 IU/mL, 400 IU/mL or 500 IU/mL) by addition of the insulin formulation (Humulin® R, Novolog®, Humalog® or Apidra®). The concentrated insulin formulation has the same concentrations of excipients as the commercial formulation at 100 IU/mL.

The final pH is adjusted to 7.4±0.4. The clear solution is filtered through a 0.22 μm membrane and stored at 4° C.

B67. Preparation of a Solution of Lispro Insulin at 200 IU/mL in the Presence of the Substituted Anionic Compound A1 and Citrate For a final volume of 100 mL of formulation, with a [substituted anionic compound A1]/[lispro insulin] mass ratio of 2, the various reagents are mixed in the amounts specified below:

| | |
|---|---|
| Lispro insulin at 200 IU/mL | 100 mL |
| Lyophilizate of substituted anionic compound A1 | 1460 mg |
| Sodium citrate solution at 1.188M | 1566 µL |

The final pH is adjusted to 7.4±0.4. The clear solution is filtered through a 0.22 µm membrane and stored at 4° C.

B68. Preparation of a Solution of Lispro Insulin at 200 IU/mL in the Presence of the Substituted Anionic Compound A1 and of the Polyanionic Compound 1

For a final volume of 100 mL of formulation, with a [substituted anionic compound A1]/[polyanionic compound 1]/[lispro insulin] mass ratio of 2/2/1, the various reagents are mixed in the amounts specified below:

| | |
|---|---|
| Lispro insulin at 200 IU/mL | 100 mL |
| Lyophilizate of substituted anionic compound A1 | 1460 mg |
| Lyophilizate of polyanionic compound 1 | 1460 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B69. Preparation of a Solution of Lispro Insulin at 200 IU/mL in the Presence of the Substituted Anionic Compound A1 and of the Polyanionic Compound 1

For a final volume of 100 mL of formulation, with a [substituted anionic compound A1]/[polyanionic compound 1]/[lispro insulin] mass ratio of 2/4/1, the various reagents are mixed in the amounts specified below:

| | |
|---|---|
| Lispro insulin at 200 IU/mL | 100 mL |
| Lyophilizate of substituted anionic compound A1 | 1460 mg |
| Lyophilizate of polyanionic compound 1 | 2920 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B70. Preparation of a Solution of Human Insulin at 200 IU/mL in the Presence of the Substituted Anionic Compound A1 and Citrate For a final volume of 100 mL of formulation, with a [substituted anionic compound A1]/[human insulin] mass ratio of 2, the various reagents are mixed in the amounts specified below:

| | |
|---|---|
| Human insulin at 200 IU/mL | 100 mL |
| Lyophilizate of substituted anionic compound A1 | 1460 mg |
| Sodium citrate solution at 1.188M | 1566 µL |

The final pH is adjusted to 7.4±0.4. The clear solution is filtered through a 0.22 µm membrane and stored at 4° C.

B71. Preparation of a Solution of Human Insulin at 200 IU/mL in the Presence of the Substituted Anionic Compound A1 and of the Polyanionic Compound 1

For a final volume of 100 mL of formulation with a [substituted anionic compound A1]/[polyanionic compound 1]/[human insulin] mass ratio of 2/2/1, the various reagents are mixed in the amounts specified below:

| | |
|---|---|
| Human insulin at 200 IU/mL | 100 mL |
| Lyophilizate of substituted anionic compound A1 | 1460 mg |
| Lyophilizate of polyanionic compound 1 | 1460 mg |

The final pH is adjusted to 7.4±0.4. The clear solution is filtered through a 0.22 µm membrane and stored at 4° C.

B72. Preparation of a Solution of Human Insulin at 200 IU/mL in the Presence of the Substituted Anionic Compound A1 and of the Polyanionic Compound 1

For a final volume of 100 mL of formulation with a [substituted anionic compound A1]/[polyanionic compound 1]/[human insulin] mass ratio of 2/4/1, the various reagents are mixed in the amounts specified below:

| | |
|---|---|
| Human insulin at 200 IU/mL | 100 mL |
| Lyophilizate of substituted anionic compound A1 | 1460 mg |
| Lyophilizate of polyanionic compound 1 | 2920 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B73. Preparation of a Solution of Aspart Insulin at 200 IU/mL in the Presence of the Substituted Anionic Compound A1 at 14.6 mg/mL and 18.6 mM of Citrate For a final volume of 100 mL of formulation, with a [substituted anionic compound A1]/[aspart insulin] mass ratio of 2.0, the various reagents are mixed in the amounts specified below:

| | |
|---|---|
| Lyophilizate of substituted anionic compound A1 | 1460 mg |
| Aspart insulin at 200 IU/mL | 100 mL |
| Sodium citrate solution at 1.188M | 1566 µL |

The final pH is adjusted to 7.4±0.4. The clear solution is filtered through a 0.22 µm membrane and stored at 4° C.

B74. Preparation of a Solution of Glulisine Insulin at 200 IU/mL in the Presence of the Substituted Anionic Compound A1 and Citrate For a final volume of 100 mL of formulation, with a [substituted anionic compound A1]/[glulisine insulin] mass ratio of 2, the various reagents are mixed in the amounts specified below and in the following order:

| | |
|---|---|
| Lyophilizate of substituted anionic compound A1 | 1460 mg |
| Glulisine insulin at 200 IU/mL | 100 mL |
| Sodium citrate solution at 1.188M | 1566 µL |

The final pH is adjusted to 7.4±0.4. The clear solution is filtered through a 0.22 µm membrane and stored at 4° C.

B75. Preparation of a Solution of Lispro Insulin at 200 IU/mL in the Presence of the Substituted Anionic Compound A2 and Citrate For a final volume of 100 mL of formulation, with a [substituted anionic compound A2]/[lispro insulin] mass ratio of 2, the various reagents are mixed in the amounts specified below:

| | |
|---|---|
| Lispro insulin at 200 IU/mL | 100 mL |
| Lyophilizate of substituted anionic compound A2 | 1460 mg |
| Sodium citrate solution at 1.188M | 1566 µL |

The final pH is adjusted to 7.4±0.4. The clear solution is filtered through a 0.22 µm membrane and stored at 4° C.

B76. Preparation of a Solution of Lispro Insulin at 200 IU/mL in the Presence of the Substituted Anionic Compound A2 and of the Polyanionic Compound 1

For a final volume of 100 mL of formulation, with a [substituted anionic compound A2]/[polyanionic compound 1]/[lispro insulin] mass ratio of 2/2/1, the various reagents are mixed in the amounts specified below:

| | |
|---|---|
| Lispro insulin at 200 IU/mL | 100 mL |
| Lyophilizate of substituted anionic compound A2 | 1460 mg |
| Lyophilizate of polyanionic compound 1 | 1460 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B77. Preparation of a Solution of Lispro Insulin at 200 IU/mL in the Presence of the Substituted Anionic Compound A2 and of the Polyanionic Compound 1

For a final volume of 100 mL of formulation, with a [substituted anionic compound A2]/[polyanionic compound 1]/[lispro insulin] mass ratio of 2/4/1, the various reagents are mixed in the amounts specified below:

| | |
|---|---|
| Lispro insulin at 200 IU/mL | 100 mL |
| Lyophilizate of substituted anionic compound A2 | 1460 mg |
| Lyophilizate of polyanionic compound 1 | 2920 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B78. Preparation of a Solution of Human Insulin at 200 IU/mL in the Presence of the Substituted Anionic Compound A2 and Citrate For a final volume of 100 mL of formulation, with a [substituted anionic compound A2]/[human insulin] mass ratio of 2, the various reagents are mixed in the amounts specified below:

| | |
|---|---|
| Human insulin at 200 IU/mL | 100 mL |
| Lyophilizate of substituted anionic compound A2 | 1460 mg |
| Sodium citrate solution at 1.188M | 1566 µL |

The final pH is adjusted to 7.4±0.4. The clear solution is filtered through a 0.22 µm membrane and stored at 4° C.

B79. Preparation of a Solution of Human Insulin at 200 IU/mL in the Presence of the Substituted Anionic Compound A2 and of the Polyanionic Compound 1

For a final volume of 100 mL of formulation with a [substituted anionic compound A2]/[polyanionic compound 1]/[human insulin] mass ratio of 2/2/1, the various reagents are mixed in the amounts specified below:

| | |
|---|---|
| Human insulin at 200 IU/mL | 100 mL |
| Lyophilizate of substituted anionic compound A2 | 1460 mg |
| Lyophilizate of polyanionic compound 1 | 1460 mg |

The final pH is adjusted to 7.4±0.4. The clear solution is filtered through a 0.22 µm membrane and stored at 4° C.

B80. Preparation of a Solution of Human Insulin at 200 IU/mL in the Presence of the Substituted Anionic Compound A2 and of the Polyanionic Compound 1

For a final volume of 100 mL of formulation with a [substituted anionic compound A2]/[polyanionic compound 1]/[human insulin] mass ratio of 2/4/1, the various reagents are mixed in the amounts specified below:

| | |
|---|---|
| Human insulin at 200 IU/mL | 100 mL |
| Lyophilizate of substituted anionic compound A2 | 1460 mg |
| Lyophilizate of polyanionic compound 1 | 2920 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B81. Preparation of a Solution of Aspart Insulin at 200 IU/mL in the Presence of the Substituted Anionic Compound A2 and Citrate For a final volume of 100 mL of formulation, with a [substituted anionic compound A2]/[aspart insulin] mass ratio of 2.0, the various reagents are mixed in the amounts specified below and in the following order:

| | |
|---|---|
| Lyophilizate of substituted anionic compound A2 | 1460 mg |
| Aspart insulin at 200 IU/mL | 100 mL |
| Sodium citrate solution at 1.188M | 1566 µL |

The final pH is adjusted to 7.4±0.4. The clear solution is filtered through a 0.22 µm membrane and stored at 4° C.

B82. Preparation of a Solution of Glulisine Insulin at 200 IU/mL in the Presence of the Substituted Anionic Compound A2 and Citrate For a final volume of 100 mL of formulation, with a [substituted anionic compound A2]/[glulisine insulin] mass ratio of 2, the various reagents are mixed in the amounts specified below and in the following order:

| | |
|---|---|
| Lyophilizate of substituted anionic compound A2 | 1460 mg |
| Glulisine insulin at 200 IU/mL | 100 mL |
| Sodium citrate solution at 1.188M | 1566 µL |

The final pH is adjusted to 7.4±0.4. The clear solution is filtered through a 0.22 µm membrane and stored at 4° C.

B83. Preparation of a Solution of Lispro Insulin at 200 IU/mL in the Presence of the Substituted Anionic Compound A3 and Citrate For a final volume of 100 mL of formulation, with a [substituted anionic compound A3]/[lispro insulin] mass ratio of 2, the various reagents are mixed in the amounts specified below:

| | |
|---|---|
| Lispro insulin at 200 IU/mL | 100 mL |
| Lyophilizate of substituted anionic compound A3 | 1460 mg |
| Sodium citrate solution at 1.188M | 1566 µL |

The final pH is adjusted to 7.4±0.4. The clear solution is filtered through a 0.22 µm membrane and stored at 4° C.

B84. Preparation of a Solution of Lispro Insulin at 200 IU/mL in the Presence of the Substituted Anionic Compound A3 and of the Polyanionic Compound 1

For a final volume of 100 mL of formulation, with a [substituted anionic compound A3]/[polyanionic compound 1]/[lispro insulin] mass ratio of 2/2/1, the various reagents are mixed in the amounts specified below:

| | |
|---|---|
| Lispro insulin at 200 IU/mL | 100 mL |
| Lyophilizate of substituted anionic compound A3 | 1460 mg |
| Lyophilizate of polyanionic compound 1 | 1460 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B85. Preparation of a Solution of Lispro Insulin at 200 IU/mL in the Presence of the Substituted Anionic Compound A3 and of the Polyanionic Compound 1

For a final volume of 100 mL of formulation, with a [substituted anionic compound A3]/[polyanionic compound 1]/[lispro insulin] mass ratio of 2/4/1, the various reagents are mixed in the amounts specified below:

| | |
|---|---|
| Lispro insulin at 200 IU/mL | 100 mL |
| Lyophilizate of substituted anionic compound A3 | 1460 mg |
| Lyophilizate of polyanionic compound 1 | 2920 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B86. Preparation of a Solution of Human Insulin at 200 IU/mL in the Presence of the Substituted Anionic Compound A3 and Citrate For a final volume of 100 mL of formulation, with a [substituted anionic compound A3]/[human insulin] mass ratio of 2, the various reagents are mixed in the amounts specified below:

| | |
|---|---|
| Human insulin at 200 IU/mL | 100 mL |
| Lyophilizate of substituted anionic compound A3 | 1460 mg |
| Sodium citrate solution at 1.188M | 1566 µL |

The final pH is adjusted to 7.4±0.4. The clear solution is filtered through a 0.22 µm membrane and stored at 4° C.

B87. Preparation of a Solution of Human Insulin at 200 IU/mL in the Presence of the Substituted Anionic Compound A3 and of the Polyanionic Compound 1

For a final volume of 100 mL of formulation with a [substituted anionic compound A3]/[polyanionic compound 1]/[human insulin] mass ratio of 2/2/1, the various reagents are mixed in the amounts specified below:

| | |
|---|---|
| Human insulin at 200 IU/mL | 100 mL |
| Lyophilizate of substituted anionic compound A3 | 1460 mg |
| Lyophilizate of polyanionic compound 1 | 1460 mg |

The final pH is adjusted to 7.4±0.4. The clear solution is filtered through a 0.22 µm membrane and stored at 4° C.

B88. Preparation of a Solution of Human Insulin at 200 IU/mL in the Presence of the Substituted Anionic Compound A3 and of the Polyanionic Compound 1

For a final volume of 100 mL of formulation with a [substituted anionic compound A3]/[polyanionic compound 1]/[human insulin] mass ratio of 2/4/1, the various reagents are mixed in the amounts specified below:

| | |
|---|---|
| Human insulin at 200 IU/mL | 100 mL |
| Lyophilizate of substituted anionic compound A3 | 1460 mg |
| Lyophilizate of polyanionic compound 1 | 2920 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B89. Preparation of a Solution of Aspart Insulin at 200 IU/mL in the Presence of the Substituted Anionic Compound A3 and Citrate For a final volume of 100 mL of formulation, with a [substituted anionic compound A3]/[aspart insulin] mass ratio of 2.0, the various reagents are mixed in the amounts specified below and in the following order:

| | |
|---|---|
| Lyophilizate of substituted anionic compound A3 | 1460 mg |
| Aspart insulin at 200 IU/mL | 100 mL |
| Sodium citrate solution at 1.188M | 1566 µL |

The final pH is adjusted to 7.4±0.4. The clear solution is filtered through a 0.22 µm membrane and stored at 4° C.

B90. Preparation of a Solution of Glulisine Insulin at 200 IU/mL in the Presence of the Substituted Anionic Compound A3 and Citrate For a final volume of 100 mL of formulation, with a [substituted anionic compound A3]/[glulisine insulin] mass ratio of 2, the various reagents are mixed in the amounts specified below and in the following order:

| | |
|---|---|
| Lyophilizate of substituted anionic compound A3 | 1460 mg |
| Glulisine insulin at 200 IU/mL | 100 mL |
| Sodium citrate solution at 1.188M | 1566 µL |

The final pH is adjusted to 7.4±0.4. The clear solution is filtered through a 0.22 µm membrane and stored at 4° C.

B91. Preparation of a Solution of Lispro Insulin at 200 IU/mL in the Presence of the Substituted Anionic Compound A4 and Citrate For a final volume of 100 mL of formulation, with a [substituted anionic compound A4]/[lispro insulin] mass ratio of 2, the various reagents are mixed in the amounts specified below:

| Lispro insulin at 200 IU/mL | 100 mL |
|---|---|
| Lyophilizate of substituted anionic compound A4 | 1460 mg |
| Sodium citrate solution at 1.188M | 1566 µL |

The final pH is adjusted to 7.4±0.4. The clear solution is filtered through a 0.22 µm membrane and stored at 4° C.

B92. Preparation of a Solution of Lispro Insulin at 200 IU/mL in the Presence of the Substituted Anionic Compound A4 and of the Polyanionic Compound 1

For a final volume of 100 mL of formulation, with a [substituted anionic compound A4]/[polyanionic compound 1]/[lispro insulin] mass ratio of 2/2/1, the various reagents are mixed in the amounts specified below:

| Lispro insulin at 200 IU/mL | 100 mL |
|---|---|
| Lyophilizate of substituted anionic compound A4 | 1460 mg |
| Lyophilizate of polyanionic compound 1 | 1460 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B93. Preparation of a Solution of Lispro Insulin at 200 IU/mL in the Presence of the Substituted Anionic Compound A4 and of the Polyanionic Compound 1

For a final volume of 100 mL of formulation, with a [substituted anionic compound A4]/[polyanionic compound 1]/[lispro insulin] mass ratio of 2/4/1, the various reagents are mixed in the amounts specified below:

| Lispro insulin at 200 IU/mL | 100 mL |
|---|---|
| Lyophilizate of substituted anionic compound A4 | 1460 mg |
| Lyophilizate of polyanionic compound 1 | 2920 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B94. Preparation of a Solution of Human Insulin at 200 IU/mL in the Presence of the Substituted Anionic Compound A4 and Citrate For a final volume of 100 mL of formulation, with a [substituted anionic compound A4]/[human insulin] mass ratio of 2, the various reagents are mixed in the amounts specified below:

| Human insulin at 200 IU/mL | 100 mL |
|---|---|
| Lyophilizate of substituted anionic compound A4 | 1460 mg |
| Sodium citrate solution at 1.188M | 1566 µL |

The final pH is adjusted to 7.4±0.4. The clear solution is filtered through a 0.22 µm membrane and stored at 4° C.

B95. Preparation of a Solution of Human Insulin at 200 IU/mL in the Presence of the Substituted Anionic Compound A4 and of the Polyanionic Compound 1

For a final volume of 100 mL of formulation with a [substituted anionic compound A4]/[polyanionic compound 1]/[human insulin] mass ratio of 2/2/1, the various reagents are mixed in the amounts specified below:

| Human insulin at 200 IU/mL | 100 mL |
|---|---|
| Lyophilizate of substituted anionic compound A4 | 1460 mg |
| Lyophilizate of polyanionic compound 1 | 1460 mg |

The final pH is adjusted to 7.4±0.4. The clear solution is filtered through a 0.22 µm membrane and stored at 4° C.

B96. Preparation of a Solution of Human Insulin at 200 IU/mL in the Presence of the Substituted Anionic Compound A4 and of the Polyanionic Compound 1

For a final volume of 100 mL of formulation with a [substituted anionic compound A4]/[polyanionic compound 1]/[human insulin] mass ratio of 2/4/1, the various reagents are mixed in the amounts specified below:

| Human insulin at 200 IU/mL | 100 mL |
|---|---|
| Lyophilizate of substituted anionic compound A4 | 1460 mg |
| Lyophilizate of polyanionic compound 1 | 2920 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B97. Preparation of a Solution of Aspart Insulin at 200 IU/mL in the Presence of the Substituted Anionic Compound A4 and Citrate For a final volume of 100 mL of formulation, with a [substituted anionic compound A4]/[aspart insulin] mass ratio of 2.0, the various reagents are mixed in the amounts specified below and in the following order:

| Lyophilizate of substituted anionic compound A4 | 1460 mg |
|---|---|
| Aspart insulin at 200 IU/mL | 100 mL |
| Sodium citrate solution at 1.188M | 1566 µL |

The final pH is adjusted to 7.4±0.4. The clear solution is filtered through a 0.22 µm membrane and stored at 4° C.

B98. Preparation of a Solution of Glulisine Insulin at 200 IU/mL in the Presence of the Substituted Anionic Compound A4 and Citrate For a final volume of 100 mL of formulation, with a [substituted anionic compound A4]/[glulisine insulin] mass ratio of 2, the various reagents are mixed in the amounts specified below and in the following order:

| Lyophilizate of substituted anionic compound A4 | 1460 mg |
|---|---|
| Glulisine insulin at 200 IU/mL | 100 mL |
| Sodium citrate solution at 1.188M | 1566 µL |

The final pH is adjusted to 7.4±0.4. The clear solution is filtered through a 0.22 µm membrane and stored at 4° C.

B99. Preparation of a Solution of Lispro Insulin at 200 IU/mL in the Presence of the Substituted Anionic Compound A5 and Citrate For a final volume of 100 mL of formulation, with a [substituted anionic compound A5]/[lispro insulin] mass ratio of 2, the various reagents are mixed in the amounts specified below:

| | |
|---|---|
| Lispro insulin at 200 IU/mL | 100 mL |
| Lyophilizate of substituted anionic compound A5 | 1460 mg |
| Sodium citrate solution at 1.188M | 1566 μL |

The final pH is adjusted to 7.4±0.4. The clear solution is filtered through a 0.22 μm membrane and stored at 4° C.

B100. Preparation of a Solution of Lispro Insulin at 200 IU/mL in the Presence of the Substituted Anionic Compound A5 and of the Polyanionic Compound 1

For a final volume of 100 mL of formulation, with a [substituted anionic compound A5]/[polyanionic compound 1]/[lispro insulin] mass ratio of 2/2/1, the various reagents are mixed in the amounts specified below:

| | |
|---|---|
| Lispro insulin at 200 IU/mL | 100 mL |
| Lyophilizate of substituted anionic compound A5 | 1460 mg |
| Lyophilizate of polyanionic compound 1 | 460 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B101. Preparation of a Solution of Lispro Insulin at 200 IU/mL in the Presence of the Substituted Anionic Compound A5 and of the Polyanionic Compound 1

For a final volume of 100 mL of formulation, with a [substituted anionic compound A5]/[polyanionic compound 1]/[lispro insulin] mass ratio of 2/4/1, the various reagents are mixed in the amounts specified below:

| | |
|---|---|
| Lispro insulin at 200 IU/mL | 100 mL |
| Lyophilizate of substituted anionic compound A5 | 1460 mg |
| Lyophilizate of polyanionic compound 1 | 2920 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B102. Preparation of a Solution of Human Insulin at 200 IU/mL in the Presence of the Substituted Anionic Compound A5 and Citrate For a final volume of 100 mL of formulation, with a [substituted anionic compound A5]/[human insulin] mass ratio of 2, the various reagents are mixed in the amounts specified below:

| | |
|---|---|
| Human insulin at 200 IU/mL | 100 mL |
| Lyophilizate of substituted anionic compound A5 | 1460 mg |
| Sodium citrate solution at 1.188M | 1566 μL |

The final pH is adjusted to 7.4±0.4. The clear solution is filtered through a 0.22 μm membrane and stored at 4° C.

B103. Preparation of a Solution of Human Insulin at 200 IU/mL in the Presence of the Substituted Anionic Compound A5 and of the Polyanionic compound 1

For a final volume of 100 mL of formulation with a [substituted anionic compound A5]/[polyanionic compound 1]/[human insulin] mass ratio of 2/2/1, the various reagents are mixed in the amounts specified below:

| | |
|---|---|
| Human insulin at 200 IU/mL | 100 mL |
| Lyophilizate of substituted anionic compound A5 | 1460 mg |
| Lyophilizate of polyanionic compound 1 | 1460 mg |

The final pH is adjusted to 7.4±0.4. The clear solution is filtered through a 0.22 μm membrane and stored at 4° C.

B104. Preparation of a Solution of Human Insulin at 200 IU/mL in the Presence of the Substituted Anionic Compound A5 and of the Polyanionic Compound 1

For a final volume of 100 mL of formulation with a [substituted anionic compound A5]/[polyanionic compound 1]/[human insulin] mass ratio of 2/4/1, the various reagents are mixed in the amounts specified below:

| | |
|---|---|
| Human insulin at 200 IU/mL | 100 mL |
| Lyophilizate of substituted anionic compound A5 | 1460 mg |
| Lyophilizate of polyanionic compound 1 | 2920 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B105. Preparation of a Solution of Aspart Insulin at 200 IU/mL in the Presence of the Substituted Anionic Compound A5 and Citrate For a final volume of 100 mL of formulation, with a [substituted anionic compound A5]/[aspart insulin] mass ratio of 2.0, the various reagents are mixed in the amounts specified below and in the following order:

| | |
|---|---|
| Lyophilizate of substituted anionic compound A5 | 1460 mg |
| Aspart insulin at 200 IU/mL | 100 mL |
| Sodium citrate solution at 1.188M | 1566 μL |

The final pH is adjusted to 7.4±0.4. The clear solution is filtered through a 0.22 μm membrane and stored at 4° C.

B106. Preparation of a Solution of Glulisine Insulin at 200 IU/mL in the Presence of the Substituted Anionic Compound A5 and Citrate For a final volume of 100 mL of formulation, with a [substituted anionic compound A5]/[glulisine insulin] mass ratio of 2, the various reagents are mixed in the amounts specified below and in the following order:

| | |
|---|---|
| Lyophilizate of substituted anionic compound A5 | 1460 mg |
| Glulisine insulin at 200 IU/mL | 100 mL |
| Sodium citrate solution at 1.188M | 1566 μL |

The final pH is adjusted to 7.4±0.4. The clear solution is filtered through a 0.22 μm membrane and stored at 4° C.

B107. Preparation of a Solution of Lispro Insulin at 200 IU/mL in the Presence of the Substituted Anionic Compound A6 and Citrate For a final volume of 100 mL of formulation, with a [substituted anionic compound A6]/[lispro insulin] mass ratio of 2, the various reagents are mixed in the amounts specified below:

| | |
|---|---|
| Lispro insulin at 200 IU/mL | 100 mL |
| Lyophilizate of substituted anionic compound A6 | 1460 mg |
| Sodium citrate solution at 1.188M | 1566 µL |

The final pH is adjusted to 7.4±0.4. The clear solution is filtered through a 0.22 µm membrane and stored at 4° C.

B108. Preparation of a Solution of Lispro Insulin at 200 IU/mL in the Presence of the Substituted Anionic Compound A6 and of the Polyanionic Compound 1

For a final volume of 100 mL of formulation, with a [substituted anionic compound A6]/[polyanionic compound 1]/[lispro insulin] mass ratio of 2/2/1, the various reagents are mixed in the amounts specified below:

| | |
|---|---|
| Lispro insulin at 200 IU/mL | 100 mL |
| Lyophilizate of substituted anionic compound A6 | 1460 mg |
| Lyophilizate of polyanionic compound 1 | 1460 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B109. Preparation of a Solution of Lispro Insulin at 200 IU/mL in the Presence of the Substituted Anionic Compound A6 and of the Polyanionic Compound 1

For a final volume of 100 mL of formulation, with a [substituted anionic compound A6]/[polyanionic compound 1]/[lispro insulin] mass ratio of 2/4/1, the various reagents are mixed in the amounts specified below:

| | |
|---|---|
| Lispro insulin at 200 IU/mL | 100 mL |
| Lyophilizate of substituted anionic compound A6 | 1460 mg |
| Lyophilizate of polyanionic compound 1 | 2920 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B110. Preparation of a Solution of Human Insulin at 200 IU/mL in the Presence of the Substituted Anionic Compound A6 and Citrate For a final volume of 100 mL of formulation, with a [substituted anionic compound A6]/[human insulin] mass ratio of 2, the various reagents are mixed in the amounts specified below:

| | |
|---|---|
| Human insulin at 200 IU/mL | 100 mL |
| Lyophilizate of substituted anionic compound A6 | 1460 mg |
| Sodium citrate solution at 1.188M | 1566 µL |

The final pH is adjusted to 7.4±0.4. The clear solution is filtered through a 0.22 µm membrane and stored at 4° C.

B111. Preparation of a Solution of Human Insulin at 200 IU/mL in the Presence of the Substituted Anionic Compound A6 and of the Polyanionic compound 1

For a final volume of 100 mL of formulation with a [substituted anionic compound A6]/[polyanionic compound 1]/[human insulin] mass ratio of 2/2/1, the various reagents are mixed in the amounts specified below:

| | |
|---|---|
| Human insulin at 200 IU/mL | 100 mL |
| Lyophilizate of substituted anionic compound A6 | 1460 mg |
| Lyophilizate of polyanionic compound 1 | 1460 mg |

The final pH is adjusted to 7.4±0.4. The clear solution is filtered through a 0.22 µm membrane and stored at 4° C.

B112. Preparation of a Solution of Human Insulin at 200 IU/mL in the Presence of the Substituted Anionic Compound A6 and of the Polyanionic compound 1

For a final volume of 100 mL of formulation with a [substituted anionic compound A6]/[polyanionic compound 1]/[human insulin] mass ratio of 2/4/1, the various reagents are mixed in the amounts specified below:

| | |
|---|---|
| Human insulin at 200 IU/mL | 100 mL |
| Lyophilizate of substituted anionic compound A6 | 1460 mg |
| Lyophilizate of polyanionic compound 1 | 2920 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B113. Preparation of a Solution of Aspart Insulin at 200 IU/mL in the Presence of the Substituted Anionic Compound A6 and Citrate For a final volume of 100 mL of formulation, with a [substituted anionic compound A6]/[aspart insulin] mass ratio of 2.0, the various reagents are mixed in the amounts specified below and in the following order:

| | |
|---|---|
| Lyophilizate of substituted anionic compound A6 | 1460 mg |
| Aspart insulin at 200 IU/mL | 100 mL |
| Sodium citrate solution at 1.188M | 1566 µL |

The final pH is adjusted to 7.4±0.4. The clear solution is filtered through a 0.22 µm membrane and stored at 4° C.

B114. Preparation of a Solution of Glulisine Insulin at 200 IU/mL in the Presence of the Substituted Anionic Compound A6 and Citrate For a final volume of 100 mL of formulation, with a [substituted anionic compound A6]/[glulisine insulin] mass ratio of 2, the various reagents are mixed in the amounts specified below and in the following order:

| | |
|---|---|
| Lyophilizate of substituted anionic compound A6 | 1460 mg |
| Glulisine insulin at 200 IU/mL | 100 mL |
| Sodium citrate solution at 1.188M | 1566 µL |

The final pH is adjusted to 7.4±0.4. The clear solution is filtered through a 0.22 µm membrane and stored at 4° C.

B115. Preparation of a Solution of Lispro Insulin at 200 IU/mL in the Presence of the Substituted Anionic Compound A7 and Citrate For a final volume of 100 mL of formulation, with a [substituted anionic compound A7]/[lispro insulin] mass ratio of 2, the various reagents are mixed in the amounts specified below:

| | |
|---|---|
| Lispro insulin at 200 IU/mL | 100 mL |
| Lyophilizate of substituted anionic compound A7 | 1460 mg |
| Sodium citrate solution at 1.188M | 1566 µL |

The final pH is adjusted to 7.4±0.4. The clear solution is filtered through a 0.22 µm membrane and stored at 4° C.

B116. Preparation of a Solution of Lispro Insulin at 200 IU/mL in the Presence of the Substituted Anionic Compound A7 and of the Polyanionic Compound 1

For a final volume of 100 mL of formulation, with a [substituted anionic compound A7]/[polyanionic compound 1]/[lispro insulin] mass ratio of 2/2/1, the various reagents are mixed in the amounts specified below:

| | |
|---|---|
| Lispro insulin at 200 IU/mL | 100 mL |
| Lyophilizate of substituted anionic compound A7 | 1460 mg |
| Lyophilizate of polyanionic compound 1 | 1460 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B117. Preparation of a Solution of Lispro Insulin at 200 IU/mL in the Presence of the Substituted Anionic Compound A7 and of the Polyanionic Compound 1

For a final volume of 100 mL of formulation, with a [substituted anionic compound A7]/[polyanionic compound 1]/[lispro insulin] mass ratio of 2/4/1, the various reagents are mixed in the amounts specified below:

| | |
|---|---|
| Lispro insulin at 200 IU/mL | 100 mL |
| Lyophilizate of substituted anionic compound A7 | 1460 mg |
| Lyophilizate of polyanionic compound 1 | 2920 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B118. Preparation of a Solution of Human Insulin at 200 IU/mL in the Presence of the Substituted Anionic Compound A7 and Citrate For a final volume of 100 mL of formulation, with a [substituted anionic compound A7]/[human insulin] mass ratio of 2, the various reagents are mixed in the amounts specified below:

| | |
|---|---|
| Human insulin at 200 IU/mL | 100 mL |
| Lyophilizate of substituted anionic compound A7 | 1460 mg |
| Sodium citrate solution at 1.188M | 1566 µL |

The final pH is adjusted to 7.4±0.4. The clear solution is filtered through a 0.22 µm membrane and stored at 4° C.

B119. Preparation of a Solution of Human Insulin at 200 IU/mL in the Presence of the Substituted Anionic Compound A7 and of the Polyanionic Compound 1

For a final volume of 100 mL of formulation with a [substituted anionic compound A7]/[polyanionic compound 1]/[human insulin] mass ratio of 2/2/1, the various reagents are mixed in the amounts specified below:

| | |
|---|---|
| Human insulin at 200 IU/mL | 100 mL |
| Lyophilizate of substituted anionic compound A7 | 1460 mg |
| Lyophilizate of polyanionic compound 1 | 1460 mg |

The final pH is adjusted to 7.4±0.4. The clear solution is filtered through a 0.22 µm membrane and stored at 4° C.

B120. Preparation of a Solution of Human Insulin at 200 IU/mL in the Presence of the Substituted Anionic Compound A7 and of the Polyanionic Compound 1

For a final volume of 100 mL of formulation with a [substituted anionic compound A7]/[polyanionic compound 1]/[human insulin] mass ratio of 2/4/1, the various reagents are mixed in the amounts specified below:

| | |
|---|---|
| Human insulin at 200 IU/mL | 100 mL |
| Lyophilizate of substituted anionic compound A7 | 1460 mg |
| Lyophilizate of polyanionic compound 1 | 2920 mg |

The polyanionic compound 1 may be used in the acid form or in the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B121. Preparation of a Solution of Aspart Insulin at 200 IU/mL in the Presence of the Substituted Anionic Compound A7 and Citrate For a final volume of 100 mL of formulation, with a [substituted anionic compound A7]/[aspart insulin] mass ratio of 2.0, the various reagents are mixed in the amounts specified below and in the following order:

| | |
|---|---|
| Lyophilizate of substituted anionic compound A7 | 1460 mg |
| Aspart insulin at 200 IU/mL | 100 mL |
| Sodium citrate solution at 1.188M | 1566 µL |

The final pH is adjusted to 7.4±0.4. The clear solution is filtered through a 0.22 µm membrane and stored at 4° C.

B122. Preparation of a Solution of Glulisine Insulin at 200 IU/mL in the Presence of the Substituted Anionic Compound A7 and Citrate For a final volume of 100 mL of formulation, with a [substituted anionic compound A7]/[glulisine insulin] mass ratio of 2, the various reagents are mixed in the amounts specified below and in the following order:

| | |
|---|---|
| Lyophilizate of substituted anionic compound A7 | 1460 mg |
| Glulisine insulin at 200 IU/mL | 100 mL |
| Sodium citrate solution at 1.188M | 1566 µL |

The final pH is adjusted to 7.4±0.4. The clear solution is filtered through a 0.22 µm membrane and stored at 4° C.

B123. Preparation of a Solution of Lispro Insulin at 300 IU/mL in the Presence of the Substituted Anionic Compound A1 and Citrate For a final volume of 100 mL of formulation, with a [substituted anionic compound A1]/[lispro insulin] mass ratio of 2.0, the various reagents are mixed in the amounts specified below:

| Lispro insulin at 300 IU/mL | 100 mL |
|---|---|
| Lyophilizate of substituted anionic compound A1 | 2190 mg |
| Sodium citrate | 720 mg |

The final pH is adjusted to 7.4±0.4. The clear solution is filtered through a 0.22 µm membrane and stored at 4° C.

B124. Preparation of a Solution of Human Insulin at 300 IU/mL in the Presence of the Substituted Anionic Compound A1 and Citrate For a final volume of 100 mL of formulation, with a [substituted anionic compound A1]/[human insulin] mass ratio of 2.0, the various reagents are mixed in the amounts specified below:

| Human insulin at 300 IU/mL | 100 mL |
|---|---|
| Lyophilizate of substituted anionic compound A1 | 2190 mg |
| Sodium citrate | 720 mg |

The final pH is adjusted to 7.4±0.4. The clear solution is filtered through a 0.22 µm membrane and stored at 4° C.

B125. Preparation of a Solution of Glulisine Insulin at 300 IU/mL in the Presence of the Substituted Anionic Compound A1 and Citrate For a final volume of 100 mL of formulation, with a [substituted anionic compound A1]/[glulisine insulin] mass ratio of 2.0, the various reagents are mixed in the amounts specified below:

| Glulisine insulin at 300 IU/mL | 100 mL |
|---|---|
| Lyophilizate of substituted anionic compound A1 | 2190 mg |
| Sodium citrate | 720 mg |

The final pH is adjusted to 7.4±0.4. The clear solution is filtered through a 0.22 µm membrane and stored at 4° C.

B126. Preparation of a Solution of Aspart Insulin at 300 IU/mL in the Presence of the Substituted Anionic Compound A1 and Citrate For a final volume of 100 mL of formulation, with a [substituted anionic compound A1]/[aspart insulin] mass ratio of 2.0, the various reagents are mixed in the amounts specified below:

| Aspart insulin at 300 IU/mL | 100 mL |
|---|---|
| Lyophilizate of substituted anionic compound A1 | 2190 mg |
| Sodium citrate | 720 mg |

The final pH is adjusted to 7.4±0.4. The clear solution is filtered through a 0.22 µm membrane and stored at 4° C.

B127. Preparation of a Solution of Lispro Insulin at 400 IU/mL in the Presence of the Substituted Anionic Compound A1 and Citrate For a final volume of 100 mL of formulation, with a [substituted anionic compound A1]/[lispro insulin] mass ratio of 2.0, the various reagents are mixed in the amounts specified below:

| Lispro insulin at 400 IU/mL | 100 mL |
|---|---|
| Lyophilizate of substituted anionic compound A1 | 2920 mg |
| Sodium citrate | 960 mg |

The final pH is adjusted to 7.4±0.4. The clear solution is filtered through a 0.22 µm membrane and stored at 4° C.

B128. Preparation of a Solution of Human Insulin at 400 IU/mL in the Presence of the Substituted Anionic Compound A1 and Citrate For a final volume of 100 mL of formulation, with a [substituted anionic compound A1]/[human insulin] mass ratio of 2.0, the various reagents are mixed in the amounts specified below:

| Human insulin at 400 IU/mL | 100 mL |
|---|---|
| Lyophilizate of substituted anionic compound A1 | 2920 mg |
| Sodium citrate | 960 mg |

The final pH is adjusted to 7.4±0.4. The clear solution is filtered through a 0.22 µm membrane and stored at 4° C.

B129. Preparation of a Solution of Glulisine Insulin at 400 IU/mL in the Presence of the Substituted Anionic Compound A1 and Citrate For a final volume of 100 mL of formulation, with a [substituted anionic compound A1]/[glulisine insulin] mass ratio of 2.0, the various reagents are mixed in the amounts specified below:

| Glulisine insulin at 400 IU/mL | 100 mL |
|---|---|
| Lyophilizate of substituted anionic compound A1 | 2920 mg |
| Sodium citrate | 960 mg |

The final pH is adjusted to 7.4±0.4. The clear solution is filtered through a 0.22 µm membrane and stored at 4° C.

B130. Preparation of a Solution of Aspart Insulin at 400 IU/mL in the Presence of the Substituted Anionic Compound A1 and Citrate For a final volume of 100 mL of formulation, with a [substituted anionic compound A1]/[aspart insulin] mass ratio of 2, the various reagents are mixed in the amounts specified below:

| Aspart insulin at 400 IU/mL | 100 mL |
|---|---|
| Lyophilizate of substituted anionic compound A1 | 2920 mg |
| Sodium citrate | 960 mg |

The final pH is adjusted to 7.4±0.4. The clear solution is filtered through a 0.22 µm membrane and stored at 4° C.

B131. Preparation of a Solution of Lispro Insulin at 500 IU/mL in the Presence of the Substituted Anionic Compound A1 and Citrate For a final volume of 100 mL of formulation, with a [substituted anionic compound A1]/[lispro insulin] mass ratio of 2.0, the various reagents are mixed in the amounts specified below:

| Lispro insulin at 500 IU/mL | 100 mL |
|---|---|
| Lyophilizate of substituted anionic compound A1 | 3650 mg |
| Sodium citrate | 1200 mg |

The final pH is adjusted to 7.4±0.4. The clear solution is filtered through a 0.22 µm membrane and stored at 4° C.

B132. Preparation of a Solution of Human Insulin at 500 IU/mL in the Presence of the Substituted Anionic Compound A1 and Citrate For a final volume of 100 mL of formulation, with a [substituted anionic compound A1]/[human insulin] mass ratio of 2.0, the various reagents are mixed in the amounts specified below:

| Human insulin at 500 IU/mL | 100 mL |
|---|---|
| Lyophilizate of substituted anionic compound A1 | 3650 mg |
| Sodium citrate | 1200 mg |

The final pH is adjusted to 7.4±0.4. The clear solution is filtered through a 0.22 μm membrane and stored at 4° C.

B133. Preparation of a Solution of Glulisine Insulin at 500 IU/mL in the Presence of the Substituted Anionic Compound A1 and Citrate For a final volume of 100 mL of formulation, with a [substituted anionic compound A1]/[glulisine insulin] mass ratio of 2.0, the various reagents are mixed in the amounts specified below:

| Glulisine insulin at 500 IU/mL | 100 mL |
|---|---|
| Lyophilizate of substituted anionic compound A1 | 3650 mg |
| Sodium citrate | 1200 mg |

The final pH is adjusted to 7.4±0.4. The clear solution is filtered through a 0.22 μm membrane and stored at 4° C.

B134. Preparation of a Solution of Aspart Insulin at 500 IU/mL in the Presence of the Substituted Anionic Compound A1 and Citrate For a final volume of 100 mL of formulation, with a [substituted anionic compound A1]/[aspart insulin] mass ratio of 2.0, the various reagents are mixed in the amounts specified below:

| Aspart insulin at 500 IU/mL | 100 mL |
|---|---|
| Lyophilizate of substituted anionic compound A1 | 3650 mg |
| Sodium citrate | 1200 mg |

The final pH is adjusted to 7.4±0.4. The clear solution is filtered through a 0.22 μm membrane and stored at 4° C.

B135. Preparation of a Solution of Lispro Insulin at 300 IU/mL in the Presence of the Substituted Anionic Compound A2 and Citrate For a final volume of 100 mL of formulation, with a [substituted anionic compound A2]/[lispro insulin] mass ratio of 2.0, the various reagents are mixed in the amounts specified below:

| Lispro insulin at 300 IU/mL | 100 mL |
|---|---|
| Lyophilizate of substituted anionic compound A2 | 2190 mg |
| Sodium citrate | 720 mg |

The final pH is adjusted to 7.4±0.4. The clear solution is filtered through a 0.22 μm membrane and stored at 4° C.

B136. Preparation of a Solution of Human Insulin at 300 IU/mL in the Presence of the Substituted Anionic Compound A2 and Citrate For a final volume of 100 mL of formulation, with a [substituted anionic compound A2]/[human insulin] mass ratio of 2.0, the various reagents are mixed in the amounts specified below:

| Human insulin at 300 IU/mL | 100 mL |
|---|---|
| Lyophilizate of substituted anionic compound A2 | 2190 mg |
| Sodium citrate | 720 mg |

The final pH is adjusted to 7.4±0.4. The clear solution is filtered through a 0.22 μm membrane and stored at 4° C.

B137. Preparation of a Solution of Glulisine Insulin at 300 IU/mL in the Presence of the Substituted Anionic Compound A2 and Citrate For a final volume of 100 mL of formulation, with a [substituted anionic compound A2]/[glulisine insulin] mass ratio of 2.0, the various reagents are mixed in the amounts specified below:

| Glulisine insulin at 300 IU/mL | 100 mL |
|---|---|
| Lyophilizate of substituted anionic compound A2 | 2190 mg |
| Sodium citrate | 720 mg |

The final pH is adjusted to 7.4±0.4. The clear solution is filtered through a 0.22 μm membrane and stored at 4° C.

B138. Preparation of a Solution of Aspart Insulin at 300 IU/mL in the Presence of the Substituted Anionic Compound A2 and Citrate For a final volume of 100 mL of formulation, with a [substituted anionic compound A2]/[aspart insulin] mass ratio of 2.0, the various reagents are mixed in the amounts specified below:

| Aspart insulin at 300 IU/mL | 100 mL |
|---|---|
| Lyophilizate of substituted anionic compound A2 | 2190 mg |
| Sodium citrate | 720 mg |

The final pH is adjusted to 7.4±0.4. The clear solution is filtered through a 0.22 μm membrane and stored at 4° C.

B139. Preparation of a Solution of Lispro Insulin at 400 IU/mL in the Presence of the Substituted Anionic Compound A2 and Citrate For a final volume of 100 mL of formulation, with a [substituted anionic compound A2]/[lispro insulin] mass ratio of 2.0, the various reagents are mixed in the amounts specified below:

| Lispro insulin at 400 IU/mL | 100 mL |
|---|---|
| Lyophilizate of substituted anionic compound A2 | 2920 mg |
| Sodium citrate | 960 mg |

The final pH is adjusted to 7.4±0.4. The clear solution is filtered through a 0.22 μm membrane and stored at 4° C.

B140. Preparation of a Solution of Human Insulin at 400 IU/mL in the Presence of the Substituted Anionic Compound A2 and Citrate For a final volume of 100 mL of formulation, with a [substituted anionic compound A2]/[human insulin] mass ratio of 2.0, the various reagents are mixed in the amounts specified below:

| Human insulin at 400 IU/mL | 100 mL |
|---|---|
| Lyophilizate of substituted anionic compound A2 | 2920 mg |
| Sodium citrate | 960 mg |

The final pH is adjusted to 7.4±0.4. The clear solution is filtered through a 0.22 μm membrane and stored at 4° C.

B141. Preparation of a Solution of Glulisine Insulin at 400 IU/mL in the Presence of the Substituted Anionic Compound A2 and Citrate For a final volume of 100 mL of formulation, with a [substituted anionic compound A2]/[glulisine insulin] mass ratio of 2.0, the various reagents are mixed in the amounts specified below:

| Glulisine insulin at 400 IU/mL | 100 mL |
| --- | --- |
| Lyophilizate of substituted anionic compound A2 | 2920 mg |
| Sodium citrate | 960 mg |

The final pH is adjusted to 7.4±0.4. The clear solution is filtered through a 0.22 μm membrane and stored at 4° C.

B142. Preparation of a Solution of Aspart Insulin at 400 IU/mL in the Presence of the Substituted Anionic Compound A2 and Citrate For a final volume of 100 mL of formulation, with a [substituted anionic compound A2]/[aspart insulin] mass ratio of 2, the various reagents are mixed in the amounts specified below:

| Aspart insulin at 400 IU/mL | 100 mL |
| --- | --- |
| Lyophilizate of substituted anionic compound A2 | 2920 mg |
| Sodium citrate | 960 mg |

The final pH is adjusted to 7.4±0.4. The clear solution is filtered through a 0.22 μm membrane and stored at 4° C.

B143. Preparation of a Solution of Lispro Insulin at 500 IU/mL in the Presence of the Substituted Anionic Compound A2 and Citrate For a final volume of 100 mL of formulation, with a [substituted anionic compound A2]/[lispro insulin] mass ratio of 2.0, the various reagents are mixed in the amounts specified below:

| Lispro insulin at 500 IU/mL | 100 mL |
| --- | --- |
| Lyophilizate of substituted anionic compound A2 | 3650 mg |
| Sodium citrate | 1200 mg |

The final pH is adjusted to 7.4±0.4. The clear solution is filtered through a 0.22 μm membrane and stored at 4° C.

B144. Preparation of a Solution of Human Insulin at 500 IU/mL in the Presence of the Substituted Anionic Compound A2 and Citrate For a final volume of 100 mL of formulation, with a [substituted anionic compound A2]/[human insulin] mass ratio of 2.0, the various reagents are mixed in the amounts specified below:

| Human insulin at 500 IU/mL | 100 mL |
| --- | --- |
| Lyophilizate of substituted anionic compound A2 | 3650 mg |
| Sodium citrate | 1200 mg |

The final pH is adjusted to 7.4±0.4. The clear solution is filtered through a 0.22 μm membrane and stored at 4° C.

B145. Preparation of a Solution of Glulisine Insulin at 500 IU/mL in the Presence of the Substituted Anionic Compound A2 and Citrate For a final volume of 100 mL of formulation, with a [substituted anionic compound A2]/[glulisine insulin] mass ratio of 2.0, the various reagents are mixed in the amounts specified below:

| Glulisine insulin at 500 IU/mL | 100 mL |
| --- | --- |
| Lyophilizate of substituted anionic compound A2 | 3650 mg |
| Sodium citrate | 1200 mg |

The final pH is adjusted to 7.4±0.4. The clear solution is filtered through a 0.22 μm membrane and stored at 4° C.

B146. Preparation of a Solution of Aspart Insulin at 500 IU/mL in the Presence of the Substituted Anionic Compound A2 and Citrate For a final volume of 100 mL of formulation, with a [substituted anionic compound A2]/[aspart insulin] mass ratio of 2.0, the various reagents are mixed in the amounts specified below:

| Aspart insulin at 500 IU/mL | 100 mL |
| --- | --- |
| Lyophilizate of substituted anionic compound A2 | 3650 mg |
| Sodium citrate | 1200 mg |

The final pH is adjusted to 7.4±0.4. The clear solution is filtered through a 0.22 μm membrane and stored at 4° C.

B147. Preparation of a Solution of Lispro Insulin at 300 IU/mL in the Presence of the Substituted Anionic Compound A3 and Citrate For a final volume of 100 mL of formulation, with a [substituted anionic compound A3]/[lispro insulin] mass ratio of 2.0, the various reagents are mixed in the amounts specified below:

| Lispro insulin at 300 IU/mL | 100 mL |
| --- | --- |
| Lyophilizate of substituted anionic compound A3 | 2190 mg |
| Sodium citrate | 720 mg |

The final pH is adjusted to 7.4±0.4. The clear solution is filtered through a 0.22 μm membrane and stored at 4° C.

B148. Preparation of a Solution of Human Insulin at 300 IU/mL in the Presence of the Substituted Anionic Compound A3 and Citrate For a final volume of 100 mL of formulation, with a [substituted anionic compound A3]/[human insulin] mass ratio of 2.0, the various reagents are mixed in the amounts specified below:

| Human insulin at 300 IU/mL | 100 mL |
| --- | --- |
| Lyophilizate of substituted anionic compound A3 | 2190 mg |
| Sodium citrate | 720 mg |

The final pH is adjusted to 7.4±0.4. The clear solution is filtered through a 0.22 μm membrane and stored at 4° C.

B149. Preparation of a Solution of Glulisine Insulin at 300 IU/mL in the Presence of the Substituted Anionic Compound A3 and Citrate For a final volume of 100 mL of formulation, with a [substituted anionic compound A3]/[glulisine insulin] mass ratio of 2.0, the various reagents are mixed in the amounts specified below:

| Glulisine insulin at 300 IU/mL | 100 mL |
| --- | --- |
| Lyophilizate of substituted anionic compound A3 | 2190 mg |
| Sodium citrate | 720 mg |

The final pH is adjusted to 7.4±0.4. The clear solution is filtered through a 0.22 μm membrane and stored at 4° C.

B150. Preparation of a Solution of Aspart Insulin at 300 IU/mL in the Presence of the Substituted Anionic Compound A3 and Citrate For a final volume of 100 mL of formulation, with a [substituted anionic compound A3]/[aspart insulin] mass ratio of 2.0, the various reagents are mixed in the amounts specified below:

| Aspart insulin at 300 IU/mL | 100 mL |
| --- | --- |
| Lyophilizate of substituted anionic compound A3 | 2190 mg |
| Sodium citrate | 720 mg |

The final pH is adjusted to 7.4±0.4. The clear solution is filtered through a 0.22 μm membrane and stored at 4° C.

B151. Preparation of a Solution of Lispro Insulin at 400 IU/mL in the Presence of the Substituted Anionic Compound A3 and Citrate For a final volume of 100 mL of formulation, with a [substituted anionic compound A3]/[lispro insulin] mass ratio of 2.0, the various reagents are mixed in the amounts specified below:

| Lispro insulin at 400 IU/mL | 100 mL |
| --- | --- |
| Lyophilizate of substituted anionic compound A3 | 2920 mg |
| Sodium citrate | 960 mg |

The final pH is adjusted to 7.4±0.4. The clear solution is filtered through a 0.22 μm membrane and stored at 4° C.

B152. Preparation of a Solution of Human Insulin at 400 IU/mL in the Presence of the Substituted Anionic Compound A3 and Citrate For a final volume of 100 mL of formulation, with a [substituted anionic compound A3]/[human insulin] mass ratio of 2.0, the various reagents are mixed in the amounts specified below:

| Human insulin at 400 IU/mL | 100 mL |
| --- | --- |
| Lyophilizate of substituted anionic compound A3 | 2920 mg |
| Sodium citrate | 960 mg |

The final pH is adjusted to 7.4±0.4. The clear solution is filtered through a 0.22 μm membrane and stored at 4° C.

B153. Preparation of a Solution of Glulisine Insulin at 400 IU/mL in the Presence of the Substituted Anionic Compound A3 and Citrate For a final volume of 100 mL of formulation, with a [substituted anionic compound A3]/[glulisine insulin] mass ratio of 2.0, the various reagents are mixed in the amounts specified below:

| Glulisine insulin at 400 IU/mL | 100 mL |
| --- | --- |
| Lyophilizate of substituted anionic compound A3 | 2920 mg |
| Sodium citrate | 960 mg |

The final pH is adjusted to 7.4±0.4. The clear solution is filtered through a 0.22 μm membrane and stored at 4° C.

B154. Preparation of a Solution of Aspart Insulin at 400 IU/mL in the Presence of the Substituted Anionic Compound A3 and Citrate For a final volume of 100 mL of formulation, with a [substituted anionic compound A3]/[aspart insulin] mass ratio of 2, the various reagents are mixed in the amounts specified below:

| Aspart insulin at 400 IU/mL | 100 mL |
| --- | --- |
| Lyophilizate of substituted anionic compound A3 | 2920 mg |
| Sodium citrate | 960 mg |

The final pH is adjusted to 7.4±0.4. The clear solution is filtered through a 0.22 μm membrane and stored at 4° C.

B155. Preparation of a Solution of Lispro Insulin at 500 IU/mL in the Presence of the Substituted Anionic Compound A3 and Citrate For a final volume of 100 mL of formulation, with a [substituted anionic compound A3]/[lispro insulin] mass ratio of 2.0, the various reagents are mixed in the amounts specified below:

| Lispro insulin at 500 IU/mL | 100 mL |
| --- | --- |
| Lyophilizate of substituted anionic compound A3 | 3650 mg |
| Sodium citrate | 1200 mg |

The final pH is adjusted to 7.4±0.4. The clear solution is filtered through a 0.22 μm membrane and stored at 4° C.

B156. Preparation of a Solution of Human Insulin at 500 IU/mL in the Presence of the Substituted Anionic Compound A3 and Citrate For a final volume of 100 mL of formulation, with a [substituted anionic compound A3]/[human insulin] mass ratio of 2.0, the various reagents are mixed in the amounts specified below:

| Human insulin at 500 IU/mL | 100 mL |
| --- | --- |
| Lyophilizate of substituted anionic compound A3 | 3650 mg |
| Sodium citrate | 1200 mg |

The final pH is adjusted to 7.4±0.4. The clear solution is filtered through a 0.22 μm membrane and stored at 4° C.

B157. Preparation of a Solution of Glulisine Insulin at 500 IU/mL in the Presence of the Substituted Anionic Compound A3 and Citrate For a final volume of 100 mL of formulation, with a [substituted anionic compound A3]/[glulisine insulin] mass ratio of 2.0, the various reagents are mixed in the amounts specified below:

| Glulisine insulin at 500 IU/mL | 100 mL |
| --- | --- |
| Lyophilizate of substituted anionic compound A3 | 3650 mg |
| Sodium citrate | 1200 mg |

The final pH is adjusted to 7.4±0.4. The clear solution is filtered through a 0.22 μm membrane and stored at 4° C.

B158. Preparation of a Solution of Aspart Insulin at 500 IU/mL in the Presence of the Substituted Anionic Compound A3 and Citrate For a final volume of 100 mL of formulation, with a [substituted anionic compound A3]/[aspart insulin] mass ratio of 2.0, the various reagents are mixed in the amounts specified below:

| Aspart insulin at 500 IU/mL | 100 mL |
| --- | --- |
| Lyophilizate of substituted anionic compound A3 | 3650 mg |
| Sodium citrate | 1200 mg |

The final pH is adjusted to 7.4±0.4. The clear solution is filtered through a 0.22 μm membrane and stored at 4° C.

B159. Preparation of a Solution of Lispro Insulin at 300 IU/mL in the Presence of the Substituted Anionic Compound A4 and Citrate For a final volume of 100 mL of formulation, with a [substituted anionic compound A4]/[lispro insulin] mass ratio of 2.0, the various reagents are mixed in the amounts specified below:

| Lispro insulin at 300 IU/mL | 100 mL |
| Lyophilizate of substituted anionic compound A4 | 2190 mg |
| Sodium citrate | 720 mg |

The final pH is adjusted to 7.4±0.4. The clear solution is filtered through a 0.22 µm membrane and stored at 4° C.

B160. Preparation of a Solution of Human Insulin at 300 IU/mL in the Presence of the Substituted Anionic Compound A4 and Citrate For a final volume of 100 mL of formulation, with a [substituted anionic compound A4]/[human insulin] mass ratio of 2.0, the various reagents are mixed in the amounts specified below:

| Human insulin at 300 IU/mL | 100 mL |
| Lyophilizate of substituted anionic compound A4 | 2190 mg |
| Sodium citrate | 720 mg |

The final pH is adjusted to 7.4±0.4. The clear solution is filtered through a 0.22 µm membrane and stored at 4° C.

B161. Preparation of a Solution of Glulisine Insulin at 300 IU/mL in the Presence of the Substituted Anionic Compound A4 and Citrate For a final volume of 100 mL of formulation, with a [substituted anionic compound A4]/[glulisine insulin] mass ratio of 2.0, the various reagents are mixed in the amounts specified below:

| Glulisine insulin at 300 IU/mL | 100 mL |
| Lyophilizate of substituted anionic compound A4 | 2190 mg |
| Sodium citrate | 720 mg |

The final pH is adjusted to 7.4±0.4. The clear solution is filtered through a 0.22 µm membrane and stored at 4° C.

B162. Preparation of a Solution of Aspart Insulin at 300 IU/mL in the Presence of the Substituted Anionic Compound A4 and Citrate For a final volume of 100 mL of formulation, with a [substituted anionic compound A4]/[aspart insulin] mass ratio of 2.0, the various reagents are mixed in the amounts specified below:

| Aspart insulin at 300 IU/mL | 100 mL |
| Lyophilizate of substituted anionic compound A4 | 2190 mg |
| Sodium citrate | 720 mg |

The final pH is adjusted to 7.4±0.4. The clear solution is filtered through a 0.22 µm membrane and stored at 4° C.

B163. Preparation of a Solution of Lispro Insulin at 400 IU/mL in the Presence of the Substituted Anionic Compound A4 and Citrate For a final volume of 100 mL of formulation, with a [substituted anionic compound A4]/[lispro insulin] mass ratio of 2.0, the various reagents are mixed in the amounts specified below:

| Lispro insulin at 400 IU/mL | 100 mL |
| Lyophilizate of substituted anionic compound A4 | 2920 mg |
| Sodium citrate | 960 mg |

The final pH is adjusted to 7.4±0.4. The clear solution is filtered through a 0.22 µm membrane and stored at 4° C.

B164. Preparation of a Solution of Human Insulin at 400 IU/mL in the Presence of the Substituted Anionic Compound A4 and Citrate For a final volume of 100 mL of formulation, with a [substituted anionic compound A4]/[human insulin] mass ratio of 2.0, the various reagents are mixed in the amounts specified below:

| Human insulin at 400 IU/mL | 100 mL |
| Lyophilizate of substituted anionic compound A4 | 2920 mg |
| Sodium citrate | 960 mg |

The final pH is adjusted to 7.4±0.4. The clear solution is filtered through a 0.22 µm membrane and stored at 4° C.

B165. Preparation of a Solution of Glulisine Insulin at 400 IU/mL in the Presence of the Substituted Anionic Compound A4 and Citrate For a final volume of 100 mL of formulation, with a [substituted anionic compound A4]/[glulisine insulin] mass ratio of 2.0, the various reagents are mixed in the amounts specified below:

| Glulisine insulin at 400 IU/mL | 100 mL |
| Lyophilizate of substituted anionic compound A4 | 2920 mg |
| Sodium citrate | 960 mg |

The final pH is adjusted to 7.4±0.4. The clear solution is filtered through a 0.22 µm membrane and stored at 4° C.

B166. Preparation of a Solution of Aspart Insulin at 400 IU/mL in the Presence of the Substituted Anionic Compound A4 and Citrate For a final volume of 100 mL of formulation, with a [substituted anionic compound A4]/[aspart insulin] mass ratio of 2, the various reagents are mixed in the amounts specified below:

| Aspart insulin at 400 IU/mL | 100 mL |
| Lyophilizate of substituted anionic compound A4 | 2920 mg |
| Sodium citrate | 960 mg |

The final pH is adjusted to 7.4±0.4. The clear solution is filtered through a 0.22 µm membrane and stored at 4° C.

B167. Preparation of a Solution of Lispro Insulin at 500 IU/mL in the Presence of the Substituted Anionic Compound A4 and Citrate For a final volume of 100 mL of formulation, with a [substituted anionic compound A4]/[lispro insulin] mass ratio of 2.0, the various reagents are mixed in the amounts specified below:

| Lispro insulin at 500 IU/mL | 100 mL |
| Lyophilizate of substituted anionic compound A4 | 3650 mg |
| Sodium citrate | 1200 mg |

The final pH is adjusted to 7.4±0.4. The clear solution is filtered through a 0.22 µm membrane and stored at 4° C.

B168. Preparation of a Solution of Human Insulin at 500 IU/mL in the Presence of the Substituted Anionic Compound A4 and Citrate For a final volume of 100 mL of formulation, with a [substituted anionic compound A4]/[human insulin] mass ratio of 2.0, the various reagents are mixed in the amounts specified below:

| Human insulin at 500 IU/mL | 100 mL |
|---|---|
| Lyophilizate of substituted anionic compound A4 | 3650 mg |
| Sodium citrate | 1200 mg |

The final pH is adjusted to 7.4±0.4. The clear solution is filtered through a 0.22 μm membrane and stored at 4° C.

B169. Preparation of a Solution of Glulisine Insulin at 500 IU/mL in the Presence of the Substituted Anionic Compound A4 and Citrate For a final volume of 100 mL of formulation, with a [substituted anionic compound A4]/[glulisine insulin] mass ratio of 2.0, the various reagents are mixed in the amounts specified below:

| Glulisine insulin at 500 IU/mL | 100 mL |
|---|---|
| Lyophilizate of substituted anionic compound A4 | 3650 mg |
| Sodium citrate | 1200 mg |

The final pH is adjusted to 7.4±0.4. The clear solution is filtered through a 0.22 μm membrane and stored at 4° C.

B170. Preparation of a solution of aspart insulin at 500 IU/mL in the Presence of the Substituted Anionic Compound A4 and Citrate For a final volume of 100 mL of formulation, with a [substituted anionic compound A4]/[aspart insulin] mass ratio of 2.0, the various reagents are mixed in the amounts specified below:

| Aspart insulin at 500 IU/mL | 100 mL |
|---|---|
| Lyophilizate of substituted anionic compound A3 | 3650 mg |
| Sodium citrate | 1200 mg |

The final pH is adjusted to 7.4±0.4. The clear solution is filtered through a 0.22 μm membrane and stored at 4° C.

B171. Preparation of a Solution of Lispro Insulin at 300 IU/mL in the Presence of the Substituted Anionic Compound A5 and Citrate For a final volume of 100 mL of formulation, with a [substituted anionic compound A5]/[lispro insulin] mass ratio of 2.0, the various reagents are mixed in the amounts specified below:

| Lispro insulin at 300 IU/mL | 100 mL |
|---|---|
| Lyophilizate of substituted anionic compound A5 | 2190 mg |
| Sodium citrate | 720 mg |

The final pH is adjusted to 7.4±0.4. The clear solution is filtered through a 0.22 μm membrane and stored at 4° C.

B172. Preparation of a Solution of Human Insulin at 300 IU/mL in the Presence of the Substituted Anionic Compound A5 and Citrate For a final volume of 100 mL of formulation, with a [substituted anionic compound A5]/[human insulin] mass ratio of 2.0, the various reagents are mixed in the amounts specified below:

| Human insulin at 300 IU/mL | 100 mL |
|---|---|
| Lyophilizate of substituted anionic compound A5 | 2190 mg |
| Sodium citrate | 720 mg |

The final pH is adjusted to 7.4±0.4. The clear solution is filtered through a 0.22 μm membrane and stored at 4° C.

B173. Preparation of a Solution of Glulisine Insulin at 300 IU/mL in the Presence of the Substituted Anionic Compound A5 and Citrate For a final volume of 100 mL of formulation, with a [substituted anionic compound A5]/[glulisine insulin] mass ratio of 2.0, the various reagents are mixed in the amounts specified below:

| Glulisine insulin at 300 IU/mL | 100 mL |
|---|---|
| Lyophilizate of substituted anionic compound A5 | 2190 mg |
| Sodium citrate | 720 mg |

The final pH is adjusted to 7.4±0.4. The clear solution is filtered through a 0.22 μm membrane and stored at 4° C.

B174. Preparation of a Solution of Aspart Insulin at 300 IU/mL in the Presence of the Substituted Anionic Compound A5 and Citrate For a final volume of 100 mL of formulation, with a [substituted anionic compound A5]/[aspart insulin] mass ratio of 2.0, the various reagents are mixed in the amounts specified below:

| Aspart insulin at 300 IU/mL | 100 mL |
|---|---|
| Lyophilizate of substituted anionic compound A5 | 2190 mg |
| Sodium citrate | 720 mg |

The final pH is adjusted to 7.4±0.4. The clear solution is filtered through a 0.22 μm membrane and stored at 4° C.

B175. Preparation of a Solution of Lispro Insulin at 400 IU/mL in the Presence of the Substituted Anionic Compound A5 and Citrate For a final volume of 100 mL of formulation, with a [substituted anionic compound A5]/[lispro insulin] mass ratio of 2.0, the various reagents are mixed in the amounts specified below:

| Lispro insulin at 400 IU/mL | 100 mL |
|---|---|
| Lyophilizate of substituted anionic compound A5 | 2920 mg |
| Sodium citrate | 960 mg |

The final pH is adjusted to 7.4±0.4. The clear solution is filtered through a 0.22 μm membrane and stored at 4° C.

B176. Preparation of a Solution of Human Insulin at 400 IU/mL in the Presence of the Substituted Anionic Compound A5 and Citrate For a final volume of 100 mL of formulation, with a [substituted anionic compound A5]/[human insulin] mass ratio of 2.0, the various reagents are mixed in the amounts specified below:

| Human insulin at 400 IU/mL | 100 mL |
|---|---|
| Lyophilizate of substituted anionic compound A5 | 2920 mg |
| Sodium citrate | 960 mg |

The final pH is adjusted to 7.4±0.4. The clear solution is filtered through a 0.22 μm membrane and stored at 4° C.

B177. Preparation of a Solution of Glulisine Insulin at 400 IU/mL in the Presence of the Substituted Anionic Compound A5 and Citrate For a final volume of 100 mL of formulation, with a [substituted anionic compound A5]/[glulisine insulin] mass ratio of 2.0, the various reagents are mixed in the amounts specified below:

| Glulisine insulin at 400 IU/mL | 100 mL |
| --- | --- |
| Lyophilizate of substituted anionic compound A5 | 2920 mg |
| Sodium citrate | 960 mg |

The final pH is adjusted to 7.4±0.4. The clear solution is filtered through a 0.22 μm membrane and stored at 4° C.

B178. Preparation of a Solution of Aspart Insulin at 400 IU/mL in the Presence of the Substituted Anionic Compound A5 and Citrate For a final volume of 100 mL of formulation, with a [substituted anionic compound A5]/[aspart insulin] mass ratio of 2, the various reagents are mixed in the amounts specified below:

| Aspart insulin at 400 IU/mL | 100 mL |
| --- | --- |
| Lyophilizate of substituted anionic compound A5 | 2920 mg |
| Sodium citrate | 960 mg |

The final pH is adjusted to 7.4±0.4. The clear solution is filtered through a 0.22 μm membrane and stored at 4° C.

B179. Preparation of a Solution of Lispro Insulin at 500 IU/mL in the Presence of the Substituted Anionic Compound A5 and Citrate For a final volume of 100 mL of formulation, with a [substituted anionic compound A5]/[lispro insulin] mass ratio of 2.0, the various reagents are mixed in the amounts specified below:

| Lispro insulin at 500 IU/mL | 100 mL |
| --- | --- |
| Lyophilizate of substituted anionic compound A5 | 3650 mg |
| Sodium citrate | 1200 mg |

The final pH is adjusted to 7.4±0.4. The clear solution is filtered through a 0.22 μm membrane and stored at 4° C.

B180. Preparation of a Solution of Human Insulin at 500 IU/mL in the Presence of the Substituted Anionic Compound A5 and Citrate For a final volume of 100 mL of formulation, with a [substituted anionic compound A5]/[human insulin] mass ratio of 2.0, the various reagents are mixed in the amounts specified below:

| Human insulin at 500 IU/mL | 100 mL |
| --- | --- |
| Lyophilizate of substituted anionic compound A5 | 3650 mg |
| Sodium citrate | 1200 mg |

The final pH is adjusted to 7.4±0.4. The clear solution is filtered through a 0.22 μm membrane and stored at 4° C.

B181. Preparation of a Solution of Glulisine Insulin at 500 IU/mL in the Presence of the Substituted Anionic Compound A5 and Citrate For a final volume of 100 mL of formulation, with a [substituted anionic compound A5]/[glulisine insulin] mass ratio of 2.0, the various reagents are mixed in the amounts specified below:

| Glulisine insulin at 500 IU/mL | 100 mL |
| --- | --- |
| Lyophilizate of substituted anionic compound A5 | 3650 mg |
| Sodium citrate | 1200 mg |

The final pH is adjusted to 7.4±0.4. The clear solution is filtered through a 0.22 μm membrane and stored at 4° C.

B182. Preparation of a Solution of Aspart Insulin at 500 IU/mL in the Presence of the Substituted Anionic Compound A5 and Citrate For a final volume of 100 mL of formulation, with a [substituted anionic compound A5]/[aspart insulin] mass ratio of 2.0, the various reagents are mixed in the amounts specified below:

| Aspart insulin at 500 IU/mL | 100 mL |
| --- | --- |
| Lyophilizate of substituted anionic compound A3 | 3650 mg |
| Sodium citrate | 1200 mg |

The final pH is adjusted to 7.4±0.4. The clear solution is filtered through a 0.22 μm membrane and stored at 4° C.

B183. Preparation of a Solution of Lispro Insulin at 300 IU/mL in the Presence of the Substituted Anionic Compound A6 and Citrate For a final volume of 100 mL of formulation, with a [substituted anionic compound A6]/[lispro insulin] mass ratio of 2.0, the various reagents are mixed in the amounts specified below:

| Lispro insulin at 300 IU/mL | 100 mL |
| --- | --- |
| Lyophilizate of substituted anionic compound A3 | 2190 mg |
| Sodium citrate | 720 mg |

The final pH is adjusted to 7.4±0.4. The clear solution is filtered through a 0.22 μm membrane and stored at 4° C.

B184. Preparation of a Solution of Human Insulin at 300 IU/mL in the Presence of the Substituted Anionic Compound A6 and Citrate For a final volume of 100 mL of formulation, with a [substituted anionic compound A6]/[human insulin] mass ratio of 2.0, the various reagents are mixed in the amounts specified below:

| Human insulin at 300 IU/mL | 100 mL |
| --- | --- |
| Lyophilizate of substituted anionic compound A6 | 2190 mg |
| Sodium citrate | 720 mg |

The final pH is adjusted to 7.4±0.4. The clear solution is filtered through a 0.22 μm membrane and stored at 4° C.

B185. Preparation of a Solution of Glulisine Insulin at 300 IU/mL in the Presence of the Substituted Anionic Compound A6 and Citrate For a final volume of 100 mL of formulation, with a [substituted anionic compound A6]/[glulisine insulin] mass ratio of 2.0, the various reagents are mixed in the amounts specified below:

| Glulisine insulin at 300 IU/mL | 100 mL |
| --- | --- |
| Lyophilizate of substituted anionic compound A6 | 2190 mg |
| Sodium citrate | 720 mg |

The final pH is adjusted to 7.4±0.4. The clear solution is filtered through a 0.22 μm membrane and stored at 4° C.

B186. Preparation of a Solution of Aspart Insulin at 300 IU/mL in the Presence of the Substituted Anionic Compound A6 and Citrate For a final volume of 100 mL of formulation, with a [substituted anionic compound A6]/[aspart insulin] mass ratio of 2.0, the various reagents are mixed in the amounts specified below:

| Aspart insulin at 300 IU/mL | 100 mL |
| --- | --- |
| Lyophilizate of substituted anionic compound A6 | 2190 mg |
| Sodium citrate | 720 mg |

The final pH is adjusted to 7.4±0.4. The clear solution is filtered through a 0.22 μm membrane and stored at 4° C.

B187. Preparation of a Solution of Lispro Insulin at 400 IU/mL in the Presence of the Substituted Anionic Compound A6 and Citrate For a final volume of 100 mL of formulation, with a [substituted anionic compound A6]/[lispro insulin] mass ratio of 2.0, the various reagents are mixed in the amounts specified below:

| Lispro insulin at 400 IU/mL | 100 mL |
| --- | --- |
| Lyophilizate of substituted anionic compound A6 | 2920 mg |
| Sodium citrate | 960 mg |

The final pH is adjusted to 7.4±0.4. The clear solution is filtered through a 0.22 μm membrane and stored at 4° C.

B188. Preparation of a Solution of Human Insulin at 400 IU/mL in the Presence of the Substituted Anionic Compound A6 and Citrate For a final volume of 100 mL of formulation, with a [substituted anionic compound A6]/[human insulin] mass ratio of 2.0, the various reagents are mixed in the amounts specified below:

| Human insulin at 400 IU/mL | 100 mL |
| --- | --- |
| Lyophilizate of substituted anionic compound A6 | 2920 mg |
| Sodium citrate | 960 mg |

The final pH is adjusted to 7.4±0.4. The clear solution is filtered through a 0.22 μm membrane and stored at 4° C.

B189. Preparation of a Solution of Glulisine Insulin at 400 IU/mL in the Presence of the Substituted Anionic Compound A6 and Citrate For a final volume of 100 mL of formulation, with a [substituted anionic compound A6]/[glulisine insulin] mass ratio of 2.0, the various reagents are mixed in the amounts specified below:

| Glulisine insulin at 400 IU/mL | 100 mL |
| --- | --- |
| Lyophilizate of substituted anionic compound A6 | 2920 mg |
| Sodium citrate | 960 mg |

The final pH is adjusted to 7.4±0.4. The clear solution is filtered through a 0.22 μm membrane and stored at 4° C.

B190. Preparation of a Solution of Aspart Insulin at 400 IU/mL in the Presence of the Substituted Anionic Compound A6 and Citrate For a final volume of 100 mL of formulation, with a [substituted anionic compound A6]/[aspart insulin] mass ratio of 2, the various reagents are mixed in the amounts specified below:

| Aspart insulin at 400 IU/mL | 100 mL |
| --- | --- |
| Lyophilizate of substituted anionic compound A6 | 2920 mg |
| Sodium citrate | 960 mg |

The final pH is adjusted to 7.4±0.4. The clear solution is filtered through a 0.22 μm membrane and stored at 4° C.

B191. Preparation of a Solution of Lispro Insulin at 500 IU/mL in the Presence of the Substituted Anionic Compound A6 and Citrate For a final volume of 100 mL of formulation, with a [substituted anionic compound A6]/[lispro insulin] mass ratio of 2.0, the various reagents are mixed in the amounts specified below:

| Lispro insulin at 500 IU/mL | 100 mL |
| --- | --- |
| Lyophilizate of substituted anionic compound A6 | 3650 mg |
| Sodium citrate | 1200 mg |

The final pH is adjusted to 7.4±0.4. The clear solution is filtered through a 0.22 μm membrane and stored at 4° C.

B192. Preparation of a Solution of Human Insulin at 500 IU/mL in the Presence of the Substituted Anionic Compound A6 and Citrate For a final volume of 100 mL of formulation, with a [substituted anionic compound A6]/[human insulin] mass ratio of 2.0, the various reagents are mixed in the amounts specified below:

| Human insulin at 500 IU/mL | 100 mL |
| --- | --- |
| Lyophilizate of substituted anionic compound A6 | 3650 mg |
| Sodium citrate | 1200 mg |

The final pH is adjusted to 7.4±0.4. The clear solution is filtered through a 0.22 μm membrane and stored at 4° C.

B193. Preparation of a Solution of Glulisine Insulin at 500 IU/mL in the Presence of the Substituted Anionic Compound A6 and Citrate For a final volume of 100 mL of formulation, with a [substituted anionic compound A6]/[glulisine insulin] mass ratio of 2.0, the various reagents are mixed in the amounts specified below:

| Glulisine insulin at 500 IU/mL | 100 mL |
| --- | --- |
| Lyophilizate of substituted anionic compound A6 | 3650 mg |
| Sodium citrate | 1200 mg |

The final pH is adjusted to 7.4±0.4. The clear solution is filtered through a 0.22 μm membrane and stored at 4° C.

B194. Preparation of a Solution of Aspart Insulin at 500 IU/mL in the Presence of the Substituted Anionic Compound A6 and Citrate For a final volume of 100 mL of formulation, with a [substituted anionic compound A6]/[aspart insulin] mass ratio of 2.0, the various reagents are mixed in the amounts specified below:

| Aspart insulin at 500 IU/mL | 100 mL |
| --- | --- |
| Lyophilizate of substituted anionic compound A3 | 3650 mg |
| Sodium citrate | 1200 mg |

The final pH is adjusted to 7.4±0.4. The clear solution is filtered through a 0.22 μm membrane and stored at 4° C.

B195. Preparation of a Solution of Lispro Insulin at 300 IU/mL in the Presence of the Substituted Anionic Compound A7 and Citrate For a final volume of 100 mL of formulation, with a [substituted anionic compound A7]/[lispro insulin] mass ratio of 2.0, the various reagents are mixed in the amounts specified below:

| Lispro insulin at 300 IU/mL | 100 mL |
|---|---|
| Lyophilizate of substituted anionic compound A7 | 2190 mg |
| Sodium citrate | 720 mg |

The final pH is adjusted to 7.4±0.4. The clear solution is filtered through a 0.22 μm membrane and stored at 4° C.

B196. Preparation of a Solution of Human Insulin at 300 IU/mL in the Presence of the Substituted Anionic Compound A7 and Citrate For a final volume of 100 mL of formulation, with a [substituted anionic compound A7]/[human insulin] mass ratio of 2.0, the various reagents are mixed in the amounts specified below:

| Human insulin at 300 IU/mL | 100 mL |
|---|---|
| Lyophilizate of substituted anionic compound A7 | 2190 mg |
| Sodium citrate | 720 mg |

The final pH is adjusted to 7.4±0.4. The clear solution is filtered through a 0.22 μm membrane and stored at 4° C.

B197. Preparation of a Solution of Glulisine Insulin at 300 IU/mL in the Presence of the Substituted Anionic Compound A7 and Citrate For a final volume of 100 mL of formulation, with a [substituted anionic compound A7]/[glulisine insulin] mass ratio of 2.0, the various reagents are mixed in the amounts specified below:

| Glulisine insulin at 300 IU/mL | 100 mL |
|---|---|
| Lyophilizate of substituted anionic compound A7 | 2190 mg |
| Sodium citrate | 720 mg |

The final pH is adjusted to 7.4±0.4. The clear solution is filtered through a 0.22 μm membrane and stored at 4° C.

B198. Preparation of a Solution of Aspart Insulin at 300 IU/mL in the Presence of the Substituted Anionic Compound A7 and Citrate For a final volume of 100 mL of formulation, with a [substituted anionic compound A7]/[aspart insulin] mass ratio of 2.0, the various reagents are mixed in the amounts specified below:

| Aspart insulin at 300 IU/mL | 100 mL |
|---|---|
| Lyophilizate of substituted anionic compound A7 | 2190 mg |
| Sodium citrate | 720 mg |

The final pH is adjusted to 7.4±0.4. The clear solution is filtered through a 0.22 μm membrane and stored at 4° C.

B199. Preparation of a Solution of Lispro Insulin at 400 IU/mL in the Presence of the Substituted Anionic Compound A7 and Citrate For a final volume of 100 mL of formulation, with a [substituted anionic compound A7]/[lispro insulin] mass ratio of 2.0, the various reagents are mixed in the amounts specified below:

| Lispro insulin at 400 IU/mL | 100 mL |
|---|---|
| Lyophilizate of substituted anionic compound A7 | 2920 mg |
| Sodium citrate | 960 mg |

The final pH is adjusted to 7.4±0.4. The clear solution is filtered through a 0.22 μm membrane and stored at 4° C.

B200. Preparation of a Solution of Human Insulin at 400 IU/mL in the Presence of the Substituted Anionic Compound A7 and Citrate For a final volume of 100 mL of formulation, with a [substituted anionic compound A7]/[human insulin] mass ratio of 2.0, the various reagents are mixed in the amounts specified below:

| Human insulin at 400 IU/mL | 100 mL |
|---|---|
| Lyophilizate of substituted anionic compound A7 | 2920 mg |
| Sodium citrate | 960 mg |

The final pH is adjusted to 7.4±0.4. The clear solution is filtered through a 0.22 μm membrane and stored at 4° C.

B201. Preparation of a Solution of Glulisine Insulin at 400 IU/mL in the Presence of the Substituted Anionic Compound A7 and Citrate For a final volume of 100 mL of formulation, with a [substituted anionic compound A7]/[glulisine insulin] mass ratio of 2.0, the various reagents are mixed in the amounts specified below:

| Glulisine insulin at 400 IU/mL | 100 mL |
|---|---|
| Lyophilizate of substituted anionic compound A7 | 2920 mg |
| Sodium citrate | 960 mg |

The final pH is adjusted to 7.4±0.4. The clear solution is filtered through a 0.22 μm membrane and stored at 4° C.

B202. Preparation of a Solution of Aspart Insulin at 400 IU/mL in the Presence of the Substituted Anionic Compound A7 and Citrate For a final volume of 100 mL of formulation, with a [substituted anionic compound A7]/[aspart insulin] mass ratio of 2, the various reagents are mixed in the amounts specified below:

| Aspart insulin at 400 IU/mL | 100 mL |
|---|---|
| Lyophilizate of substituted anionic compound A7 | 2920 mg |
| Sodium citrate | 960 mg |

The final pH is adjusted to 7.4±0.4. The clear solution is filtered through a 0.22 μm membrane and stored at 4° C.

B203. Preparation of a Solution of Lispro Insulin at 500 IU/mL in the Presence of the Substituted Anionic Compound A7 and Citrate For a final volume of 100 mL of formulation, with a [substituted anionic compound A7]/[lispro insulin] mass ratio of 2.0, the various reagents are mixed in the amounts specified below:

| Lispro insulin at 500 IU/mL | 100 mL |
|---|---|
| Lyophilizate of substituted anionic compound A7 | 3650 mg |
| Sodium citrate | 1200 mg |

The final pH is adjusted to 7.4±0.4. The clear solution is filtered through a 0.22 µm membrane and stored at 4° C.

B204. Preparation of a Solution of Human Insulin at 500 IU/mL in the Presence of the Substituted Anionic Compound A7 and Citrate For a final volume of 100 mL of formulation, with a [substituted anionic compound A7]/[human insulin] mass ratio of 2.0, the various reagents are mixed in the amounts specified below:

| | |
|---|---|
| Human insulin at 500 IU/mL | 100 mL |
| Lyophilizate of substituted anionic compound A7 | 3650 mg |
| Sodium citrate | 1200 mg |

The final pH is adjusted to 7.4±0.4. The clear solution is filtered through a 0.22 µm membrane and stored at 4° C.

B205. Preparation of a Solution of Glulisine Insulin at 500 IU/mL in the Presence of the Substituted Anionic Compound A7 and Citrate For a final volume of 100 mL of formulation, with a [substituted anionic compound A7]/[glulisine insulin] mass ratio of 2.0, the various reagents are mixed in the amounts specified below:

| | |
|---|---|
| Glulisine insulin at 500 IU/mL | 100 mL |
| Lyophilizate of substituted anionic compound A7 | 3650 mg |
| Sodium citrate | 1200 mg |

The final pH is adjusted to 7.4±0.4. The clear solution is filtered through a 0.22 µm membrane and stored at 4° C.

B206. Preparation of a Solution of Aspart Insulin at 500 IU/mL in the Presence of the Substituted Anionic Compound A7 and Citrate For a final volume of 100 mL of formulation, with a [substituted anionic compound A7]/[aspart insulin] mass ratio of 2.0, the various reagents are mixed in the amounts specified below:

| | |
|---|---|
| Aspart insulin at 500 IU/mL | 100 mL |
| Lyophilizate of substituted anionic compound A3 | 3650 mg |
| Sodium citrate | 1200 mg |

The final pH is adjusted to 7.4±0.4. The clear solution is filtered through a 0.22 µm membrane and stored at 4° C.

B207. Preparation of a Solution of Lispro Insulin at 200 IU/mL in the Presence of the Substituted Anionic Compound A1 and Citrate For a final volume of 100 mL of formulation, with a [substituted anionic compound A1]/[lispro insulin] mass ratio of 1, the various reagents are mixed in the amounts specified below:

| | |
|---|---|
| Lispro insulin at 200 IU/mL | 100 mL |
| Lyophilizate of substituted anionic compound A1 | 730 mg |
| Sodium citrate solution at 1.188M | 783 µL |

The final pH is adjusted to 7.4±0.4. The clear solution is filtered through a 0.22 µm membrane and stored at 4° C.

B208. Preparation of a Solution of Lispro Insulin at 200 IU/mL in the Presence of the Substituted Anionic Compound A2 and Citrate For a final volume of 100 mL of formulation, with a [substituted anionic compound A2]/[lispro insulin] mass ratio of 1, the various reagents are mixed in the amounts specified below:

| | |
|---|---|
| Lispro insulin at 200 IU/mL | 100 mL |
| Lyophilizate of substituted anionic compound A2 | 730 mg |
| Sodium citrate solution at 1.188M | 783 µL |

The final pH is adjusted to 7.4±0.4. The clear solution is filtered through a 0.22 µm membrane and stored at 4° C.

B209. Preparation of a Solution of Lispro Insulin at 200 IU/mL in the Presence of the Substituted Anionic Compound A3 and Citrate For a final volume of 100 mL of formulation, with a [substituted anionic compound A3]/[lispro insulin] mass ratio of 1, the various reagents are mixed in the amounts specified below:

| | |
|---|---|
| Lispro insulin at 200 IU/mL | 100 mL |
| Lyophilizate of substituted anionic compound A3 | 730 mg |
| Sodium citrate solution at 1.188M | 783 µL |

The final pH is adjusted to 7.4±0.4. The clear solution is filtered through a 0.22 µm membrane and stored at 4° C.

B210. Preparation of a Solution of Lispro Insulin at 200 IU/mL in the Presence of the Substituted Anionic Compound A4 and Citrate For a final volume of 100 mL of formulation, with a [substituted anionic compound A4]/[lispro insulin] mass ratio of 1, the various reagents are mixed in the amounts specified below:

| | |
|---|---|
| Lispro insulin at 200 IU/mL | 100 mL |
| Lyophilizate of substituted anionic compound A4 | 730 mg |
| Sodium citrate solution at 1.188M | 783 µL |

The final pH is adjusted to 7.4±0.4. The clear solution is filtered through a 0.22 µm membrane and stored at 4° C.

B211. Preparation of a Solution of Lispro Insulin at 200 IU/mL in the Presence of the Substituted Anionic Compound A5 and Citrate For a final volume of 100 mL of formulation, with a [substituted anionic compound A5]/[lispro insulin] mass ratio of 1, the various reagents are mixed in the amounts specified below:

| | |
|---|---|
| Lispro insulin at 200 IU/mL | 100 mL |
| Lyophilizate of substituted anionic compound A5 | 730 mg |
| Sodium citrate solution at 1.188M | 783 µL |

The final pH is adjusted to 7.4±0.4. The clear solution is filtered through a 0.22 µm membrane and stored at 4° C.

B212. Preparation of a Solution of Lispro Insulin at 200 IU/mL in the Presence of the Substituted Anionic Compound A6 and Citrate For a final volume of 100 mL of formulation, with a [substituted anionic compound A6]/[lispro insulin] mass ratio of 1, the various reagents are mixed in the amounts specified below:

| Lispro insulin at 200 IU/mL | 100 mL |
| --- | --- |
| Lyophilizate of substituted anionic compound A6 | 730 mg |
| Sodium citrate solution at 1.188M | 783 μL |

The final pH is adjusted to 7.4±0.4. The clear solution is filtered through a 0.22 μm membrane and stored at 4° C.

B213. Preparation of a Solution of Lispro Insulin at 200 IU/mL in the Presence of the Substituted Anionic Compound A7 and Citrate For a final volume of 100 mL of formulation, with a [substituted anionic compound A7]/[lispro insulin] mass ratio of 1, the various reagents are mixed in the amounts specified below:

| Lispro insulin at 200 IU/mL | 100 mL |
| --- | --- |
| Lyophilizate of substituted anionic compound A7 | 730 mg |
| Sodium citrate solution at 1.188M | 783 μL |

The final pH is adjusted to 7.4±0.4. The clear solution is filtered through a 0.22 μm membrane and stored at 4° C.

C Pharmacodynamics and Pharmacokinetics

Protocol for Measuring the Pharmacodynamics of the Insulin Solutions

Domestic pigs weighing about 50 kg, precatheterized in the jugular vein, are fasted for 2.5 hours before the start of the experiment. Within the hour prior to the injection of insulin, three blood samples are collected so as to determine the basal level of glucose and insulin.

The injection of insulin at a dose of 0.09 IU/kg for lispro insulin is performed subcutaneously in the neck, under the animal's ear, using an insulin pen (Novo, Sanofi or Lilly) equipped with a 31 G needle.

Blood samples are then collected every 4 minutes for 20 minutes and then every 10 minutes up to 3 hours. After each sample collection, the catheter is rinsed with a dilute heparin solution.

A drop of blood is collected to determine the glycemia using a glucometer.

The pharmacodynamic curves for glucose expressed as a percentage of the basal level are then plotted. The time required to reach the minimum glucose level in the blood and 50% of the minimum glucose level in the blood for each pig are determined and reported as Tmin glucose and T50% Rmin glucose, respectively. The mean values of the Tmin glucose and of the T50% Rmin glucose are then calculated.

The remaining blood is collected in a dry tube and is centrifuged to isolate the serum. The insulin levels in the serum samples are measured via the sandwich ELISA immunoenzymatic method for each pig.

The pharmacokinetic curves expressed as the delta of the basal level are then plotted. The time required to reach the maximum concentration and the time required to reach 50% of the maximum insulin concentration in the serum for each pig are determined and reported as Tmax insulin and T50% Cmax insulin, respectively. The mean values of the Tmax insulin and of the T50% Cmax insulin are then calculated.

C2: Pharmacodynamic and Pharmacokinetic Results for the Insulin Solutions of Examples B2 and B12

| Example | Insulin | Substituted anionic compound | Excipient | Number of pigs |
| --- | --- | --- | --- | --- |
| B2 | lispro | — | — | 10 |
| B12 | lispro | A2 | Citrate 9.3 mM | 11 |

The pharmacodynamic results obtained with the compositions described in examples B2 and B12 are presented in FIG. 1. Analysis of these curves shows that the composition of example B12 comprising the substituted anionic compound A2 and citrate as excipient (curve plotted with the squares corresponding to Example B12, Tmin glucose=42±12 min and T50% Rmin glucose=18±4 min) makes it possible to obtain faster action than that of the Humalog® commercial composition of example B2 (curve plotted with the triangles corresponding to example B2, Tmin glucose=47±11 min and T50% Rmin glucose=26±8 min).

Figure 2:
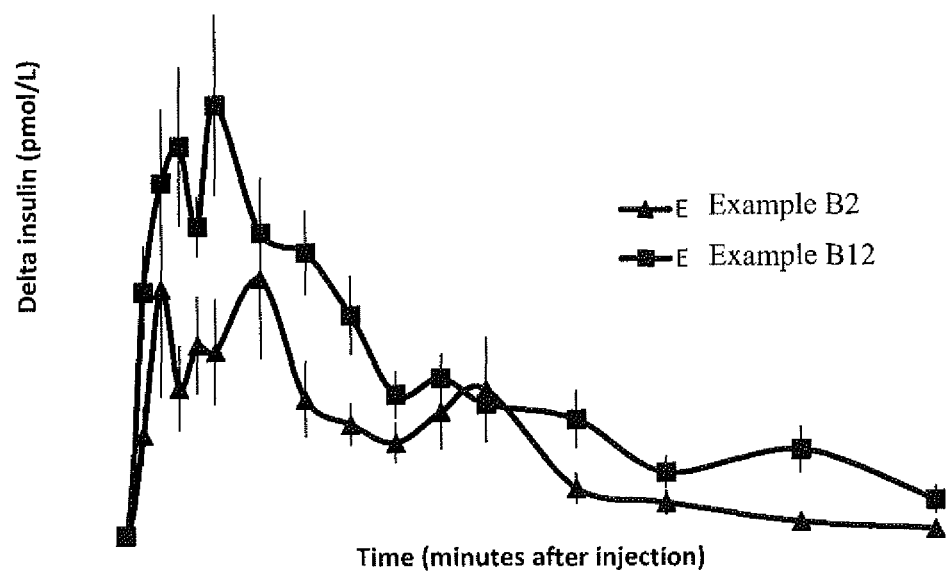
FIG. 2 describes the pharmacokinetic results obtained with the compositions described in examples B2 and B12.

The pharmacokinetic results obtained with the compositions described in examples B2 and B12 are presented in FIG. 2. Analysis of these curves shows that the composition of example B12 comprising the substituted anionic compound A2 and citrate as excipient (curve plotted with the squares corresponding to Example B12, Tmax insulin=24±18 min and T50% Cmax insulin=6±3 min) induces more rapid absorption of the lispro insulin than the Humalog® commercial composition of example B2 (curve plotted with the triangles corresponding to example B2, Tmax insulin=23±23 min and T50% Cmax insulin=17±22 min).

C3: Pharmacodynamic and Pharmacokinetic Results for the Insulin Solutions of Examples B2 and B7

| Example | Insulin | Substituted anionic compound | Excipient | Number of pigs |
| --- | --- | --- | --- | --- |
| B2 | lispro | — | — | 10 |
| B7 | lispro | A1 | Citrate 9.3 mM | 12 |

Figure 3:
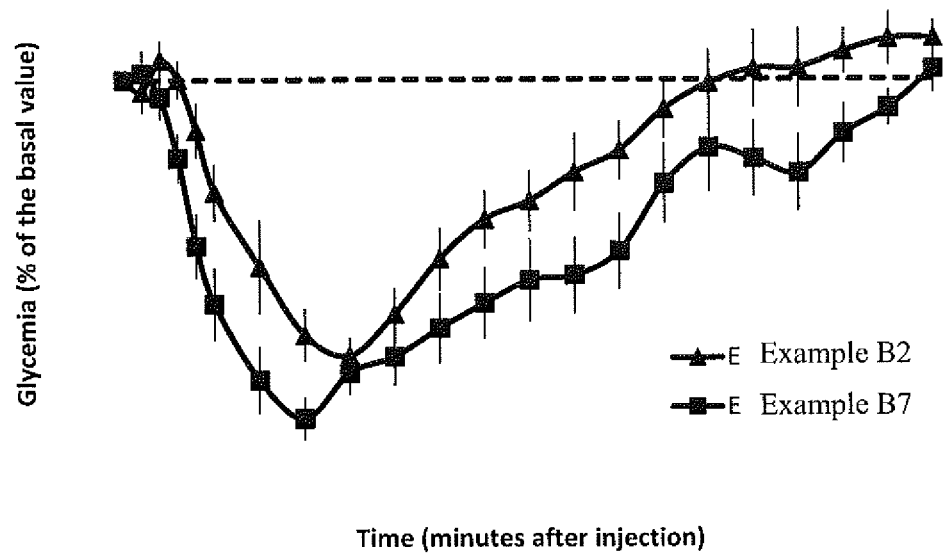
FIG. 3 describes the pharmacodynamic results obtained with the compositions described in examples B2 and B7.

The pharmacodynamic results obtained with the compositions described in examples B2 and B7 are presented in FIG. 3. Analysis of these curves shows that the composition of example B7 comprising the substituted anionic compound A1 and citrate as excipient (curve plotted with the squares corresponding to Example B7, Tmin glucose=48±22 min and T50% Rmin glucose=17±7 min) makes it possible to obtain faster action than that of the Humalog® commercial composition of example B2 (curve plotted with the triangles corresponding to example B2, Tmin glucose=47±11 min and T50% Rmin glucose=26±8 min).

Figure 4:
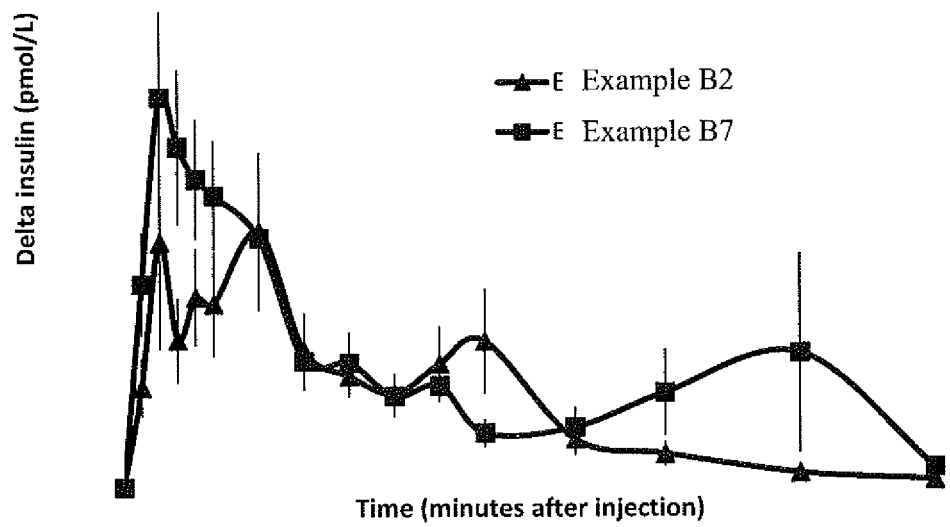
FIG. 4 describes the pharmacokinetic results obtained with the compositions described in examples B2 and B7.

The pharmacokinetic results obtained with the compositions described in examples B2 and B7 are presented in FIG. 4. Analysis of these curves shows that the composition of example B7 comprising the substituted anionic compound A1 and citrate as excipient (curve plotted with the squares corresponding to Example B7, Tmax insulin=20±14 min and T50% Cmax insulin=6±3 min) induces more rapid absorption of the lispro insulin than the Humalog® commercial composition of example B2 (curve plotted with the triangles corresponding to example B2, Tmax insulin=23±23 min and T50% Cmax insulin=17±22 min).

C3': Pharmacodynamic and Pharmacokinetic Results for the Insulin Solutions of Examples B2 and B7

| Example | Insulin | Substituted anionic compound | Excipient | Number of pigs |
|---|---|---|---|---|
| B2 | lispro | — | — | 9 |
| B7 | lispro | A1 | Citrate 9.3 mM | 11 |

Figure 14:
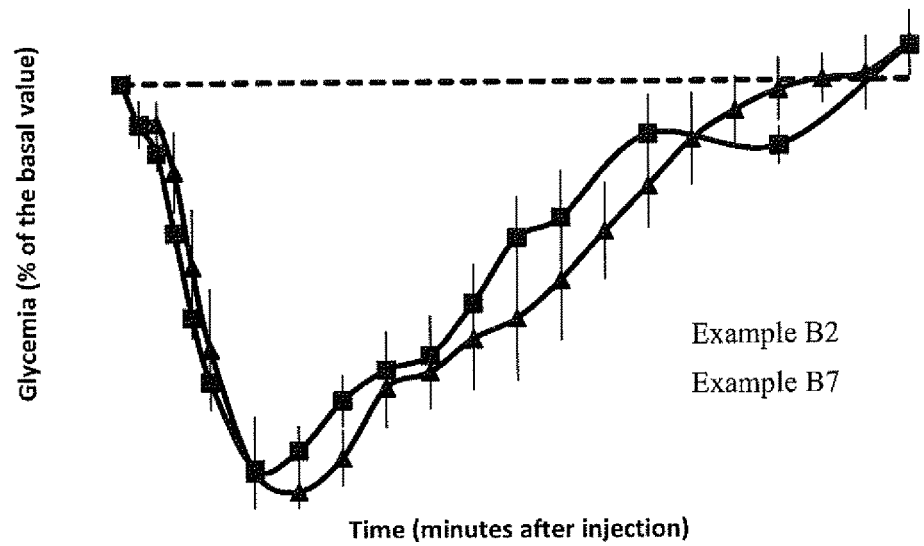

The pharmacodynamic results obtained with the compositions described in examples B2 and B7 are presented in FIG. 14. Analysis of these curves shows that the composition of example B7 comprising the substituted anionic compound A1 and citrate as excipient (curve plotted with the squares corresponding to Example B7, Tmin glucose=35±10 min and T50% Rmin glucose=14±4 min) makes it possible to obtain faster action than that of the Humalog® commercial composition of example B2 (curve plotted with the triangles corresponding to example B2, Tmin glucose=38±8 min and T50% Rmin glucose=18±10 min).

Figure 15:
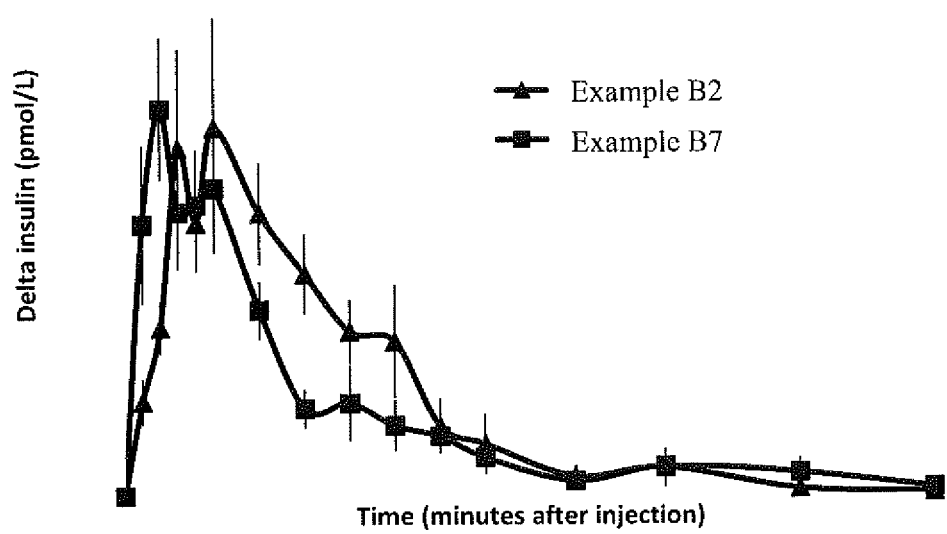
FIG. 15 describes the pharmacokinetic results obtained with the compositions described in examples B2 and B7.

The pharmacokinetic results obtained with the compositions described in examples B2 and B7 are presented in FIG. 15. Analysis of these curves shows that the composition of example B7 comprising the substituted anionic compound A1 and citrate as excipient (curve plotted with the squares corresponding to Example B7, Tmax insulin=13±6 min and T50% Cmax insulin=5±4 min) induces more rapid absorption of the lispro insulin than the Humalog® commercial composition of example B2 (curve plotted with the triangles corresponding to example B2, Tmax insulin=19±8 min and T50% Cmax insulin=8±4 min).

C4: Pharmacodynamic and Pharmacokinetic Results for the Insulin Solutions of Examples B2 and B39

| Example | Insulin | Substituted anionic compound | Excipient | Number of pigs |
|---|---|---|---|---|
| B2 | lispro | — | — | 13 |
| B39 | lispro | A5 | Citrate 9.3 mM | 8 |

Figure 7:
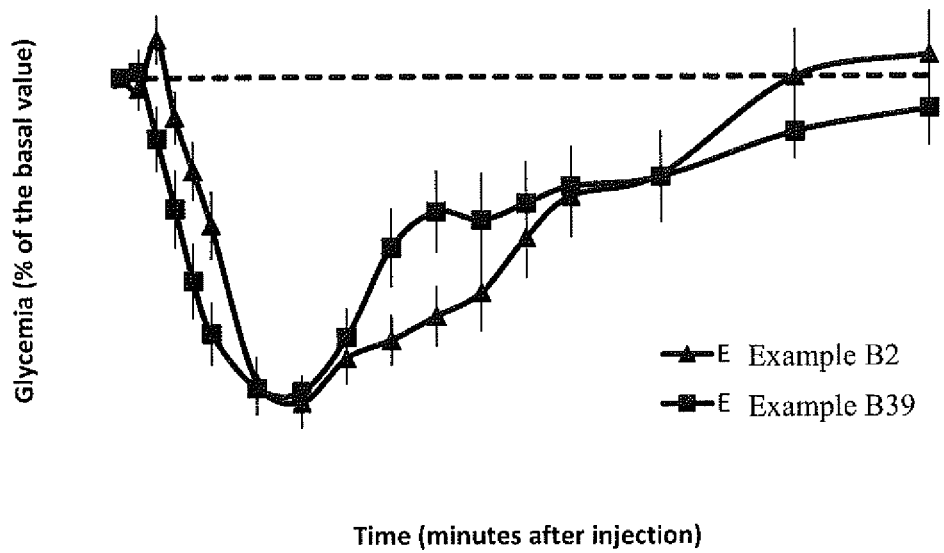
FIG. 7 describes the pharmacodynamic results obtained with the compositions described in examples B2 and B39.

The pharmacodynamic results obtained with the compositions described in examples B2 and B39 are presented in FIG. 7. Analysis of these curves shows that the composition of example B39 comprising the substituted anionic compound A5 and citrate as excipient (curve plotted with the squares corresponding to Example B39, Tmin glucose=51±25 min and T50% Rmin glucose=15±7 min) makes it possible to obtain faster action than that of the Humalog® commercial composition of example B2 (curve plotted with the triangles corresponding to example B2, Tmin glucose=46±18 min and T50% Rmin glucose=21±6 min).

Figure 8:
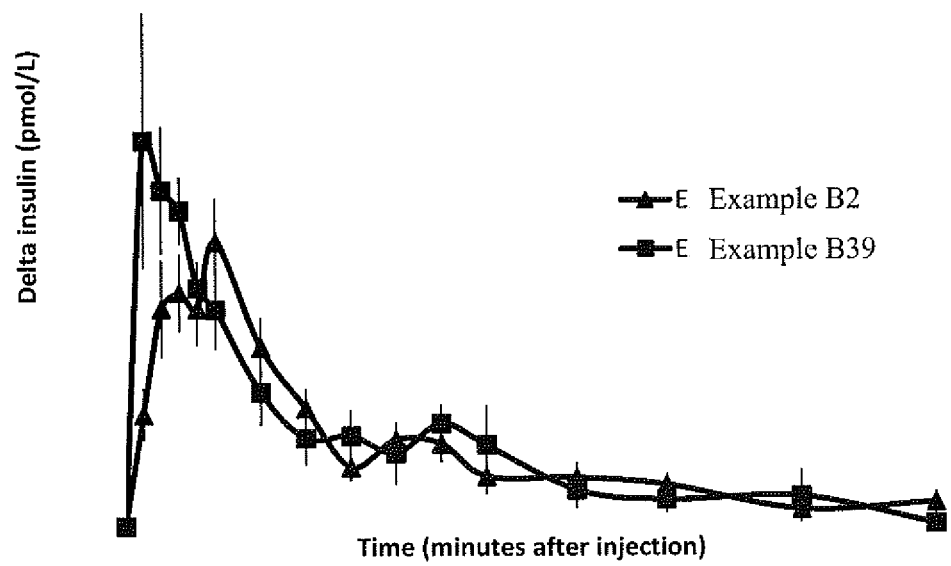
FIG. 8 describes the pharmacokinetic results obtained with the compositions described in examples B2 and B39.

The pharmacokinetic results obtained with the compositions described in examples B2 and B39 are presented in FIG. 8. Analysis of these curves shows that the composition of example B39 comprising the substituted anionic compound A5 and citrate as excipient (curve plotted with the squares corresponding to Example B39, Tmax insulin=13±12 min and T50% Cmax insulin=4±3 min) induces more rapid absorption of the lispro insulin than the Humalog® commercial composition of example B2 (curve plotted with the triangles corresponding to example B2, Tmax insulin=22±20 min and T50% Cmax insulin=7±4 min).

C5: Pharmacodynamic and Pharmacokinetic Results for the Insulin Solutions of Examples B2 and B47

| Example | Insulin | Substituted anionic compound | Excipient | Number of pigs |
|---|---|---|---|---|
| B2 | lispro | — | — | 13 |
| B47 | lispro | A6 | Citrate 9.3 mM | 11 |

Figure 9:
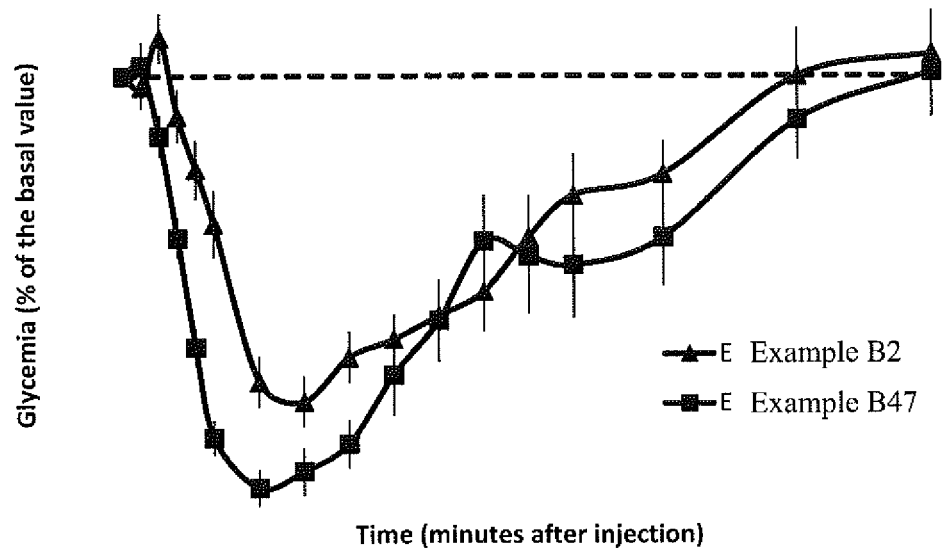
FIG. 9 describes the pharmacodynamic results obtained with the compositions described in examples B2 and B47.

The pharmacodynamic results obtained with the compositions described in examples B2 and B47 are presented in FIG. 9. Analysis of these curves shows that the composition of example B47 comprising the substituted anionic compound A6 and citrate as excipient (curve plotted with the squares corresponding to Example B47, Tmin glucose=34±10 min and T50% Rmin glucose=13±3 min) makes it possible to obtain faster action than that of the Humalog® commercial composition of example B2 (curve plotted with the triangles corresponding to example B2, Tmin glucose=46±18 min and T50% Rmin glucose=21±6 min).

Figure 10:
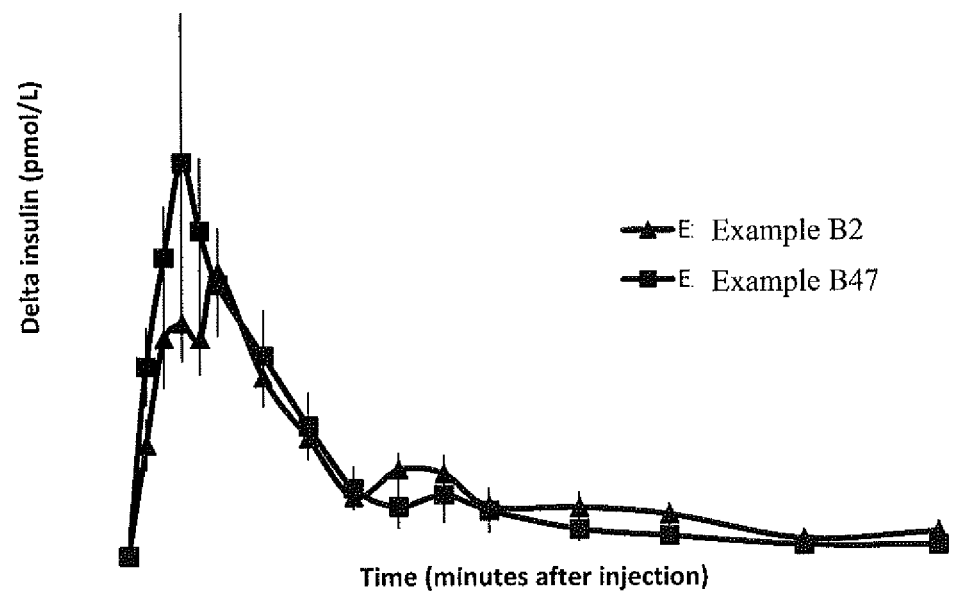
FIG. 10 FIG. 10 describes the pharmacokinetic results obtained with the compositions described in examples B2 and B47.

The pharmacokinetic results obtained with the compositions described in examples B2 and B47 are presented in FIG. 10. Analysis of these curves shows that the composition of example B47 comprising the substituted anionic compound A6 and citrate as excipient (curve plotted with the squares corresponding to Example B47, Tmax insulin=11±5 min and T50% Cmax insulin=5±3 min) induces more rapid absorption of the lispro insulin than the Humalog® commercial composition of example B2 (curve plotted with the triangles corresponding to example B2, Tmax insulin=22±20 min and T50% Cmax insulin=7±4 min).

C6: Pharmacodynamic and Pharmacokinetic Results for the Insulin Solutions of Examples B2 and B55

| Example | Insulin | Substituted anionic compound | Excipient | Number of pigs |
|---|---|---|---|---|
| B2 | lispro | — | — | 13 |
| B55 | lispro | A7 | Citrate 9.3 mM | 12 |

Figure 11:
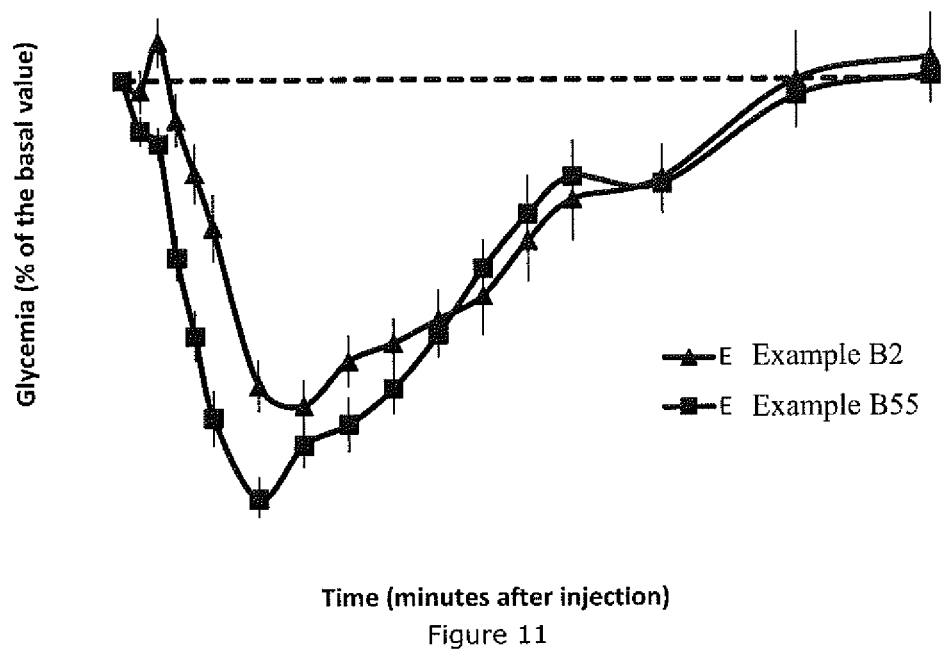
FIG. 11 describes the pharmacodynamic results obtained with the compositions described in examples B2 and B55.

The pharmacodynamic results obtained with the compositions described in examples B2 and B55 are presented in FIG. 11. Analysis of these curves shows that the composition of example B55 comprising the substituted anionic compound A7 and citrate as excipient (curve plotted with the squares corresponding to Example B55, Tmin glucose=34±15 min and T50% Rmin glucose=15±4 min) makes it possible to obtain faster action than that of the Humalog® commercial composition of example B2 (curve plotted with the triangles corresponding to example B2, Tmin glucose=46±18 min and T50% Rmin glucose=21±6 min).

Figure 12:
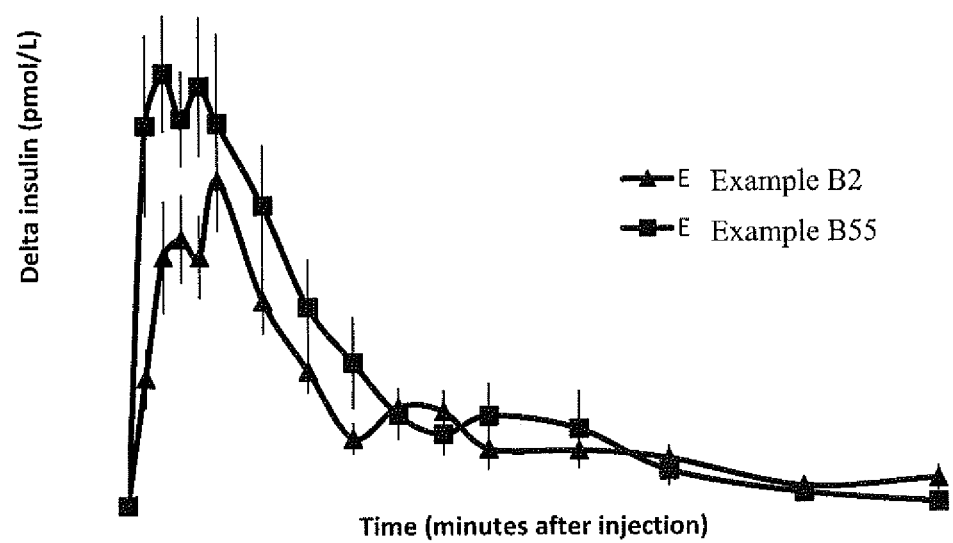
FIG. 12 describes the pharmacokinetic results obtained with the compositions described in examples B2 and B55.

The pharmacokinetic results obtained with the compositions described in examples B2 and B55 are presented in FIG. 12. Analysis of these curves shows that the composition of example B55 comprising the substituted anionic compound A7 and citrate as excipient (curve plotted with the squares corresponding to Example B55, Tmax insulin=13±9 min and T50% Cmax insulin=4±3 min) induces more rapid absorption of the lispro insulin than the Humalog® commercial composition of example B2 (curve plotted with the triangles corresponding to example B2, Tmax insulin=22±20 min and T50% Cmax insulin=7±4 min).

D Circular Dichroism (CD)

Circular dichroism makes it possible to study the secondary and quaternary structure of insulin. Insulin monomers become organized as dimers and as hexamers. The hexamer is the physically and chemically most stable form of insulin. The CD signal at 276 nm is characteristic of the hexameric form of insulin (hexamer signal at about −300°, dimer signal between −200° and −250° and monomer signal below −200°). Loss of the CD signal at 276 nm is thus characteristic of a destabilization of the hexamer into dimers or monomers.

Figure 5:
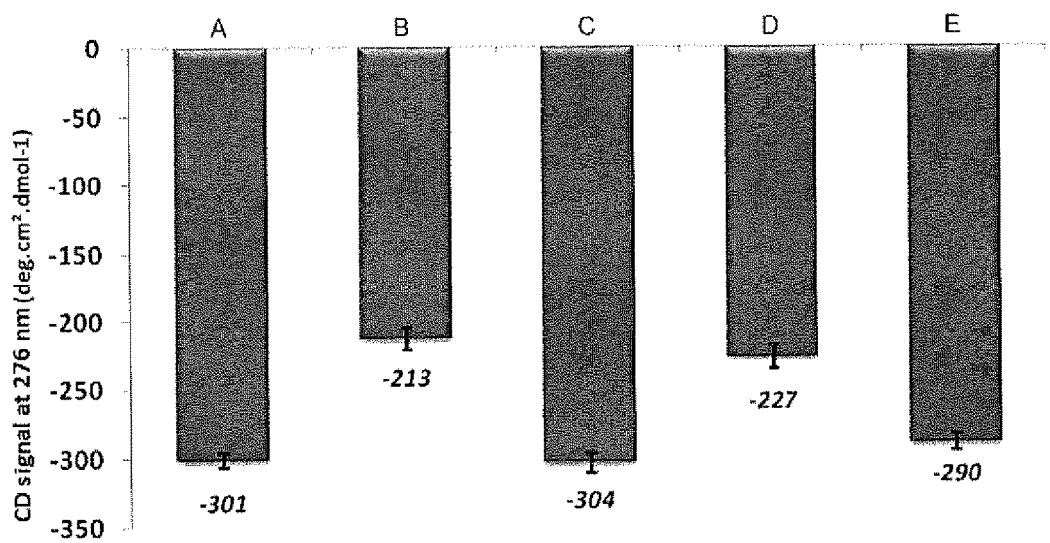
FIG. 5 describes on the y-axis the CD signal at 276 nm (deg·cm$^2$·dmol$^{-1}$) and, on the x-axis:
A: rhINS (human insulin) (100 IU/ml)
B: rhINS/EDTA
C: rhINS/Citrate
D: rhINS/EDTA/Citrate
E: rhINS/Compound A1 (100 IU/ml/7.3 mg/mL)

D1. Impact of the Substituted Anionic Compound A1 on the CD Signal of Human Insulin at 276 nm The results obtained are presented in FIG. 5. This figure describes on the y-axis the CD signal at 276 nm (deg·cm²·dmol⁻¹) and, on the x-axis:

A: rhINS (human insulin) (100 IU/ml)
B: rhINS/EDTA
C: rhINS/Citrate
D: rhINS/EDTA/Citrate
E: rhINS/Compound A1 (100 IU/ml/7.3 mg/mL)

EDTA and the EDTA/citrate combination have a very pronounced impact on the hexameric structure of human insulin (total association of the hexamer into dimers). In contrast, citrate and the substituted anionic compound A1 have no impact on the hexameric structure of human insulin. In contrast with EDTA, the compositions based on the substituted anionic compound A1 do not dissociate the hexamer of human insulin.

Figure 6:
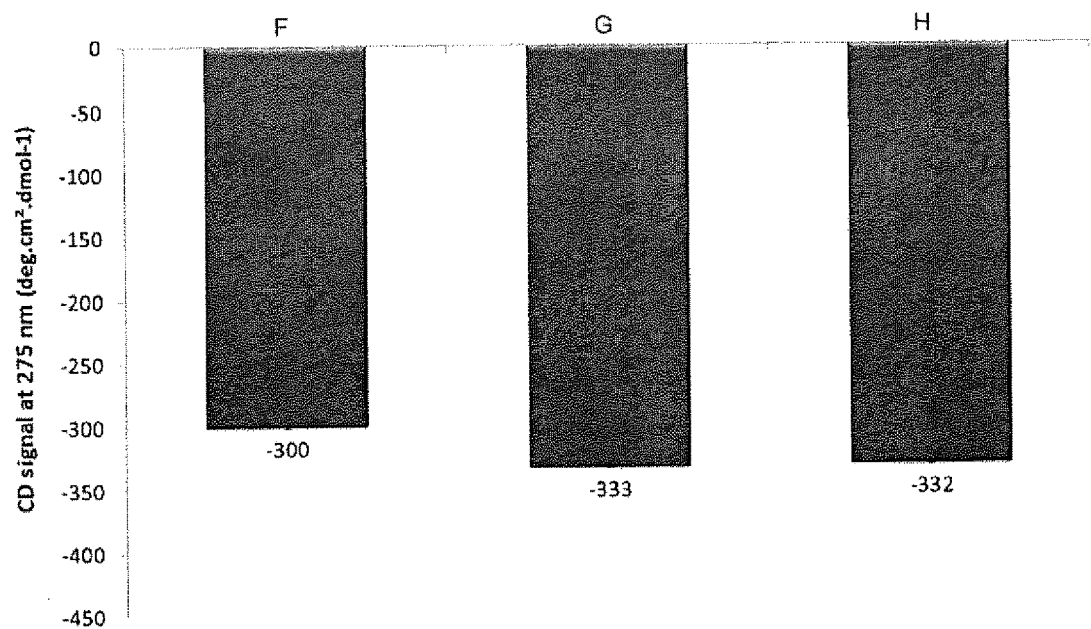
FIG. 6 describes on the y-axis the CD signal at 276 nm (deg·cm$^2$·dmol$^{-1}$) and, on the x-axis:
F: rhINS (100 IU/ml)
G: rhINS/Compound A2 (100 IU/ml/7.3 mg/mL)
H: rhINS/Compound A3 (100 IU/ml/7.3 mg/mL)

D2. Impact of the Substituted Anionic Compounds A2 and A3 on the CD Signal of Human Insulin at 276 nm The results obtained are presented in FIG. 6. This figure describes on the y-axis the CD signal at 276 nm (deg·cm²·dmol⁻¹) and, on the x-axis:

F: rhINS (100 IU/ml)
G: rhINS/Compound A2 (100 IU/ml/7.3 mg/mL)
H: rhINS/Compound A3 (100 IU/ml/7.3 mg/mL)

The substituted anionic compounds A2 and A3 have no impact on the hexameric structure of human insulin. In contrast with EDTA, the compositions based on the substituted anionic compounds A2 and A3 do not dissociate the hexamer of human insulin.

D3 State of Association of Lispro Insulin Evaluated by Circular Dichroism in the Presence of Various Substituted Anionic Compounds and Citrate Circular dichroism makes it possible to study the secondary and quaternary structure of insulin. Insulin monomers become organized as dimers and as hexamers. The hexamer is the physically and chemically most stable form of insulin. Two hexameric forms exist, the form R6 and the form T6. Lispro insulin has a strong signal at 240 nm characteristic of the hexameric form R6 (the most stable form). Loss of the signal at 240 nm is linked to a destabilization of the hexamer R6.

Preparation of a 1.010 M Sodium Citrate Solution

A sodium citrate solution is obtained by dissolving 14.9077 g of sodium citrate (50.69 mmol) in 50 mL of water in a graduated flask. The pH is adjusted to 7.4 by adding 0.21 mL of 1 M HCl.

Preparation of Solutions of Lispro Insulin at 100 IU/mL in the Presence of the Substituted Anionic Compound and Citrate For a final volume of 100 mL of formulation, with a concentration of substituted anionic compound of 7.3 mg/mL and a concentration of 9.3 mM of citrate, the various reagents are added in the amounts specified below and in the following order:

| | |
|---|---|
| Lyophilized substituted anionic compound | 730 mg |
| Commercial solution of Humalog ® at 100 IU/mL | 100 mL |
| Sodium citrate solution at 1.010M | 921 μL |

Citrate may be used in the acid form or in the basic form as the sodium salt, the potassium salt or another salt that is compatible with an injectable formulation.

The final pH is adjusted to 7.4±0.4.

The clear solution is filtered through a 0.22 μm membrane and stored at 4° C.

Preparation of the Solution of Lispro Insulin at 100 IU/mL in the Presence of Citrate For a final volume of 100 mL of formulation, with a concentration of 9.3 mM of citrate, the various compounds are added in the amounts specified below and in the following order:

| | |
|---|---|
| Commercial solution of Humalog ® at 100 IU/mL | 100 mL |
| Sodium citrate solution at 1.010M | 921 μL |

Citrate may be used in the acid form or in the basic form as the sodium salt, the potassium salt or another salt that is compatible with an injectable formulation.

The final pH is adjusted to 7.4±0.4.

The clear solution is filtered through a 0.22 μm membrane and stored at 4° C.

Preparation of the Solution of Lispro Insulin at 100 IU/mL in the Presence of EDTA For a final volume of 100 mL of formulation, with a concentration of 0.3 mM of EDTA, the various compounds are added in the amounts specified below and in the following order:

| | |
|---|---|
| Commercial solution of Humalog ® at 100 IU/mL | 100 mL |
| Commercial solution of EDTA at 0.5M | 60 μL |

The final pH is adjusted to 7.4±0.4.

The clear solution is filtered through a 0.22 μm membrane and stored at 4° C.

Figure 13:
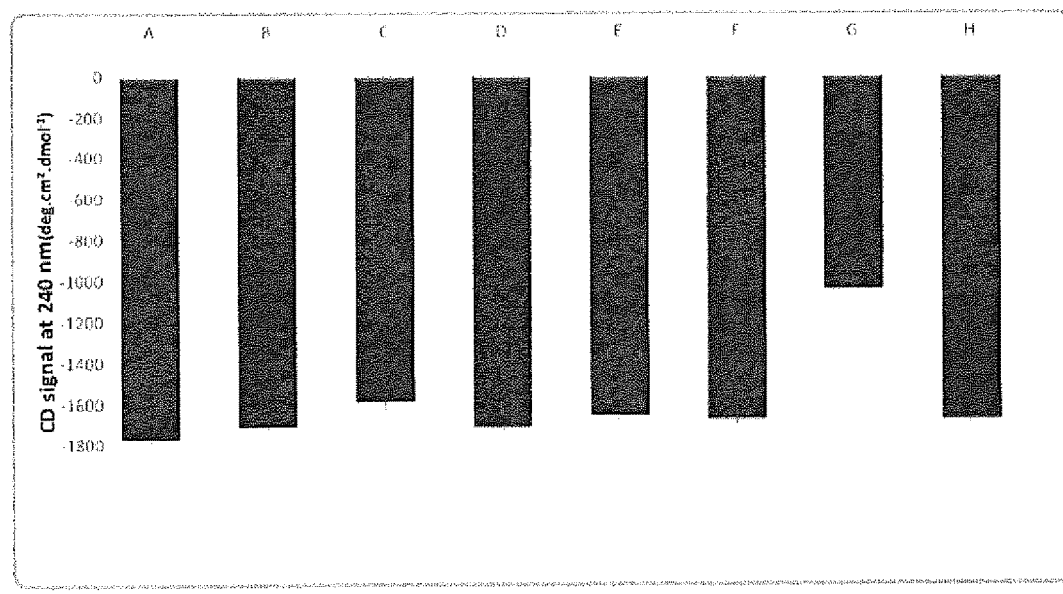
FIG. 13 describes on the y-axis the CD signal at 240 nm (deg·cm$^2$·dmol$^{-1}$) and, on the x-axis:
A: lispro insulin 100 IU/mL
B: lispro insulin+7.3 mg/mL of substituted anionic compound A1+citrate at 9.3 mM
C: lispro insulin+7.3 mg/mL of substituted anionic compound A2+citrate at 9.3 mM
D: lispro insulin+7.3 mg/mL of substituted anionic compound A5+citrate at 9.3 mM
E: lispro insulin+7.3 mg/mL of substituted anionic compound A6+citrate at 9.3 mM
F: lispro insulin+7.3 mg/mL of substituted anionic compound A7+citrate at 9.3 mM
G: lispro insulin+EDTA 300 µM
H: lispro insulin+citrate at 9.3 mM FIG. 14 describes the pharmacodynamic results obtained with the compositions described in examples B2 and B7.

The results obtained are presented in FIG. 13. This figure describes on the y-axis the CD signal at 240 nm (deg·cm²·dmol⁻¹) and, on the x-axis:

A: lispro insulin 100 IU/mL
B: lispro insulin+7.3 mg/mL of substituted anionic compound A1+citrate at 9.3 mM
C: lispro insulin+7.3 mg/mL of substituted anionic compound A2+citrate at 9.3 mM
D: lispro insulin+7.3 mg/mL of substituted anionic compound A5+citrate at 9.3 mM
E: lispro insulin+7.3 mg/mL of substituted anionic compound A6+citrate at 9.3 mM
F: lispro insulin+7.3 mg/mL of substituted anionic compound A7+citrate at 9.3 mM
G: lispro insulin+EDTA 300 μM
H: lispro insulin+citrate at 9.3 mM EDTA completely destructures the R6 form of lispro insulin. EDTA thus has a pronounced effect on the hexamer. In contrast, citrate alone and the mixture of substituted anionic compound/citrate have no impact on the CD signal at 240 nm. These compounds thus have no impact on the R6 structure of the hexamer and, all the less so, on the hexameric structure.

The invention claimed is:

1. A composition, in the form of an aqueous solution, comprising insulin in hexameric form, at least one substituted anionic compound of non-saccharide structure and at least one polyanionic compound other than said substituted anionic compound, wherein the substituted anionic compound corresponds to formula I below:

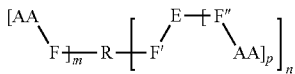

Formula I wherein
R represents a saturated or unsaturated, linear, branched or cyclic hydrocarbon-based radical comprising from 1 to 12 carbon atoms, optionally comprising at least one function chosen from ether, alcohol and carboxylic acid functions, AA is a radical resulting from an aromatic amino acid comprising a phenyl group or an indole group, which is substituted or not substituted, or an aromatic amino acid derivative comprising a phenyl group or an indole group, which is substituted or not substituted, said radical AA bearing at least one free acid function, E represents an at least divalent radical, comprising from 2 to 6 carbon atoms, F, F' and F" represent, independently of each other, a function chosen from amide, carbamate and urea functions, F and F" being functions resulting from a reaction involving the amine of the aromatic amino acid, the precursor of the radical AA, F' being a function involving a reactive function of the precursor of R and a reactive function of the precursor of E, p being an integer between 1 and 3,
m is an integer between 0 and 6; n is an integer between 0 and 6; m+n is an integer between 1 and 6;

said compound comprising at least two carboxylic acid functions in the form of a salt of an alkali metal chosen from $Na^+$ and $K^+$.

2. The composition as claimed in claim 1, wherein the substituted anionic compound is chosen from the compounds of formula I wherein the radical —R— is chosen from radicals comprising 1 to 12 carbon atoms, of formula IV:

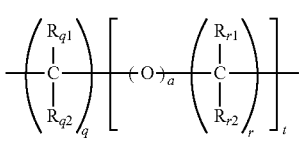

Formula IV wherein q and r are integers between 0 and 12, r is an integer between 0 and 3 and 1≤q+r*t≤12, a is equal to 0 or 1, the groups $R_{q1}$, $R_{q2}$, $R_{r1}$ and $R_{r2}$ are, independently of each other, chosen from H, —OH and —COOH, if a=0, then t=0 and when q≥1 and/or t≥1, then the radicals $R_{q1}$ and $R_{q2}$ and the radicals $R_{r1}$ and $R_{r2}$ are identical or different from one carbon to another.

3. The composition as claimed in claim 1, wherein the substituted anionic compound is chosen from the compounds of formula I wherein the radical AA is resulting from an aromatic amino acid comprising a phenyl or an indole, which is substituted or not substituted, or from an aromatic amino acid derivative comprising a phenyl or an indole, which is substituted or not substituted, most particularly, the radical AA is resulting from an aromatic amino acid comprising a phenyl or an indole, which is substituted or not substituted.

4. The composition as claimed in claim 1, wherein the substituted anionic compound is chosen from the compounds of formula I wherein the radical E is resulting from a linear or branched alkyl compound comprising at least two functions chosen from the group consisting of OH, —COOH and —NH$_2$.

5. The composition as claimed in claim 1, wherein the substituted anionic compound is chosen from the compounds of formula I wherein n=0 and corresponds to formula II:

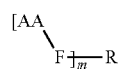

Formula II wherein:
AA, F and R have the definitions given above,
1≤m≤6.

6. The composition as claimed in claim 1, wherein the substituted anionic compound is chosen from the compounds of formula I wherein m=0 and corresponds to formula III:

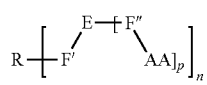

Formula III wherein:
AA, E, F', F", p and R have the definitions given above,
1≤n≤6.

7. The composition as claimed in claim 1, wherein the mole ratios of substituted anionic compound/insulin are between 0.6 and 120.

8. The composition as claimed in claim 1, wherein the mass ratios of substituted anionic compound/insulin are between 0.5 and 10.

9. The composition as claimed in claim 1, wherein the concentration of substituted anionic compound is between 1.8 and 36 mg/mL.

10. The composition as claimed in claim 1, wherein the insulin is human insulin chosen from recombinant human insulins.

11. The composition as claimed in claim 1, wherein insulin is an insulin analogue chosen from the group consisting of lispro insulin (Humalog®), aspart insulin (Novolog®, Novorapid®) and glulisine insulin (Apidra®).

12. A composition comprising a composition as claimed in claim 1, wherein the insulin concentration is between 240 and 3000 μM (40 to 500 IU/mL).

13. The composition as claimed in claim 1, wherein the polyanionic compound is chosen from the group consisting of polycarboxylic acids and the $Na^+$, $K^+$, $Ca^{2+}$ or $Mg^{2+}$ salts thereof.

14. The composition as claimed in claim 1, wherein the polyanionic compound is an anionic molecule chosen from the group consisting of citric acid, aspartic acid, glutamic acid, malic acid, tartaric acid, succinic acid, adipic acid, oxalic acid, phosphate, polyphosphoric acids and the $Na^+$, $K^+$, $Ca^{2+}$ or $Mg^{2+}$ salts thereof.

15. The composition as claimed in claim 1, wherein the concentration of polyanionic compound is between 2 and 150 mM.

16. The composition as claimed in claim 1, wherein the substituted anionic compound corresponds to formula I wherein the radical AA is resulting from phenylalanine and the radical R is resulting from tartaric acid, succinic acid or an amino acid chosen from aspartic acid and glutamic acid, the radical R is especially resulting from tartaric acid or succinic acid and in particular n=0 and m=1.

17. The composition as claimed in claim 1, wherein the substituted anionic compound corresponds to formula I wherein the radical AA is resulting from phenylalanine and the radical R is resulting from succinic acid, tartaric acid or an amino acid chosen from aspartic acid and glutamic acid, n=0 and m=1.

18. The composition as claimed in claim 1, wherein the substituted anionic compound corresponds to formula I wherein the radical AA is resulting from phenylalanine, n=0, m=1, the radical R is resulting from tartaric acid or succinic acid, in particular from tartaric acid, and bears an acid function.

19. The composition as claimed in claim 1, wherein the substituted anionic compound corresponds to formula I wherein the radical AA is resulting from phenylalanine, m=0, n=1 or 2, especially n=1, p=3 and E is resulting from TRIS.

20. The composition as claimed in claim 1, wherein the substituted anionic compound corresponds to formula I wherein the radical AA is resulting from phenylalanine, m=0, n=1 or 2, especially n=1, p=2 and E is resulting from aspartic acid or glutamic acid.

21. The composition as claimed in claim 1, wherein the substituted anionic compound corresponds to formula I wherein the radical AA is resulting from phenylalanine, m=0, n=1, 2 or 3, especially n=3, p=2 and E is resulting from aspartic acid or glutamic acid.

22. The composition as claimed in claim 1, wherein the substituted anionic compound corresponds to formula I wherein the radical R is resulting from succinic acid and comprises a carboxylic acid, m=0, n=1, p=3, E is resulting from TRIS, F' is an amide function, the radical AA is resulting from phenylalanine, and F" is a carbamate function.

23. The composition as claimed in claim 1, wherein the substituted anionic compound corresponds to formula I wherein the radical R is resulting from succinic acid and comprises a carboxylic acid, m=0, n=1, p=3, E is resulting from TRIS, F' is an amide function, the radical AA is resulting from phenylalanine, and F" is a urea function.

24. The composition as claimed in claim 1, wherein the substituted anionic compound corresponds to formula I wherein the radical R is resulting from tartaric acid and comprises a carboxylic acid, m=1, n=0, F is an amide function and the radical AA is resulting from phenylalanine.

25. The composition as claimed in claim 1, wherein the substituted anionic compound corresponds to formula I wherein the radical R is resulting from succinic acid and comprises a carboxylic acid, m=1, n=0, F is an amide function and the radical AA is resulting from phenylalanine.

26. The composition as claimed in claim 1, wherein the substituted anionic compound corresponds to formula I wherein the radical R is resulting from tartaric acid and comprises a carboxylic acid, m=0, n=1, p=3, E is resulting from TRIS, F' is an amide function, the radical AA is resulting from phenylalanine, and F" is a carbamate function.

27. The composition as claimed in claim 1, wherein the substituted anionic compound corresponds to formula I wherein the radical R is resulting from tartaric acid and comprises a carboxylic acid, m=0, n=1, p=2, E is resulting from aspartic acid, F' is an amide function, the radical AA is resulting from phenylalanine, and F" is an amide function.

\* \* \* \* \*